United States Patent [19]

Kehr et al.

[11] Patent Number: 5,752,235
[45] Date of Patent: May 12, 1998

[54] ELECTRONIC MEDICATION MONITORING AND DISPENSING METHOD

[75] Inventors: Bruce A. Kehr, Potomac, Md.; David Lerner, New York, N.Y.; Richard D. Demenus, New York, N.Y.; Michael J. Edl, New York, N.Y.

[73] Assignee: InforMedix, Inc., Rockville, Md.

[21] Appl. No.: 556,626

[22] Filed: Jul. 23, 1990

Related U.S. Application Data

[63] Continuation-in-part of Ser. No. 464,877, Jan. 17, 1990, Pat. No. 5,200,891.

[51] Int. Cl.$^6$ ............................................. G06F 15/02
[52] U.S. Cl. ............................................. 705/3
[58] Field of Search ............................. 364/400, 401, 364/413.01, 413.02, 479; 368/10, 41; 221/2, 15

[56] References Cited

U.S. PATENT DOCUMENTS

| | | |
|---|---|---|
| 3,966,086 | 6/1976 | Kelso . |
| 4,223,801 | 9/1980 | Carlson . |
| 4,258,354 | 3/1981 | Carmon et al. . |
| 4,275,384 | 6/1981 | Hicks et al. . |
| 4,293,845 | 10/1981 | Villa-Real . |
| 4,360,125 | 11/1982 | Martindale et al. . |
| 4,361,408 | 11/1982 | Wirtschafter . |
| 4,382,688 | 5/1983 | Machamer . |
| 4,473,884 | 9/1984 | Behl . |
| 4,483,626 | 11/1984 | Noble . |
| 4,490,711 | 12/1984 | Johnston . |
| 4,588,303 | 5/1986 | Wirtschafter . |
| 4,626,105 | 12/1986 | Miller . |
| 4,682,299 | 7/1987 | McIntosh et al. . |
| 4,695,954 | 9/1987 | Rose et al. . |
| 4,717,042 | 1/1988 | McLaughlin . |
| 4,725,997 | 2/1988 | Urquhart et al. . |
| 4,725,999 | 2/1988 | Tate . |
| 4,768,176 | 8/1988 | Kehr et al. . |
| 4,768,177 | 8/1988 | Kehr et al. . |
| 4,837,719 | 6/1989 | McIntosh et al. . |
| 4,879,699 | 11/1989 | Sakamoto . |
| 4,926,572 | 5/1990 | Holmes . |
| 5,020,037 | 5/1991 | Raven . |
| 5,200,891 | 4/1993 | Kehr et al. ............ 364/413.01 |

*Primary Examiner*—Robert A. Weinhardt
*Assistant Examiner*—Junghoon Kenneth Oh
*Attorney, Agent, or Firm*—William D. Hall

[57] ABSTRACT

A device for monitoring medication of a patient and for prompting the patient into certain medication taking schedule and/or certain programming steps and routines. The device has a plurality of compartments, each of which may store medication, and an electrical signaling system to emit medication alert signals from time-to-time, each of which said signals indicates (a) that medication should be taken, (b) from which compartment the medication should be taken, (c) and the quantity of medication to be taken. If a designated compartment is not opened and closed within a predetermined period of time, the electrical signaling system will display an alarm and the event will be recorded as a missed medication event, unless the patient then opens the designated compartment. If each designated compartment is opened and closed, the take-medication signal and the alarm (if operating) are turned off and the event is recorded for later review. The device may be constructed in one piece with hinged doors for each pill compartment, or each pill compartment may be a separate "drawer" sliding into a main unit.

6 Claims, 12 Drawing Sheets

ELECTRONIC MEDICATION MONITORING AND DISPENSING METHOD

RELATED APPLICATION

This application is a continuation-in-part of my prior application Ser. No. 464,877, filed Jan. 17, 1990, now U.S. Pat. No. 5,200,891.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND OF THE INVENTION

The prior art discloses a number of devices that use electronic systems for assisting a person who takes medication. Kehr U.S. Pat. No. 4,768,177 discloses a device for alerting a person when medication should be taken which medication should be taken, as well as how much medication should be taken. The Kehr et al. apparatus also has a night cut-off control which permits the device to be turned off at night. Several patents teach the use of a microprocessor to alert a person to take medication and to also supply information for a display of, or a printout of, information about the patient and/or his or her medication; see for example, McIntosh, et al. U.S. Pat. No. 4,682,299, Villa-Real U.S. Pat. No. 4,293,845 and Behl U.S. Pat. No. 4,473,884.

SUMMARY OF THE INVENTION

The prior art lacks certain features embodied in the present invention, including, but not limited to: an ability to accommodate multiple medications, each with its own prescribed regimen; a high degree of inter-action between the patient and the messages that the device displays, alerting the patient how to program the device and how to take medications; giving patient extensive commands in writing; ease of programming and ease of use in a design that is resistant to wear and tear; specific displays to increase the accuracy of programming and pill taking; means to translate routine doctor's orders into standard alarm prompting sequences; first prompting, then recording the patient's behaviors relative to pill taking; and other means, herein specified, that enhance accurate medication taking (or compliance) in accordance with research studies such as "Patient Adherence to Prescribed Therapies," Marshall H. Becker, Ph.D., Medical Care, Ma. 1985, Vol. 23, No. 5.

The present invention is a medication monitoring device which provides a number of functions for facilitating patient adherence to prescribed therapies. The device is capable of accepting, storing and displaying a medication signal as well as physician's instructions, and is capable of monitoring the presumed adherence to the schedule and the instructions.

The device of the present invention provides for ease of entry of a medication schedule, ease of review of that schedule, both prospectively and retrospectively, and allows the patient and/or the physician to readily and accurately review the compliance with that schedule. The monitoring device of the present invention, while providing visually readable instructions, insures that the patient has a correct understanding of the medication regime. Through regular interaction with the patient by its series of medication alert signals, the monitoring device of the present invention reduces the complexity of the medication regime for the patient. The monitor also requires the interaction of the patient through its series of prompts, ques, queries and requests for acknowledgement, thereby engaging the patient as an active participant in the treatment process, enhancing the efficacy of the medication regime.

The device has a plurality of medication compartments in which are inserted a plurality of drawers which may each be used to store a different medication, a microprocessor with associated circuitry for providing timing and signaling, and a display and push buttons for programming and operating the device. The device provides visual signals to prompt the user during input of a medication schedule or schedules. The device then relies upon that schedule(s) to indicate to the user when medication is to be taken by providing audible and/or visual medication alert signals. The device indicates the compartment of the device from which the medication is to be taken and the quantity of medication. The compartment indication is provided by illuminating a light closely associated with the desired compartment. A liquid crystal or other type of display indicates the quantity to take; i.e. if three pills are to be taken, the number "3" will be displayed adjacent to the appropriate compartment.

If the patient obeys the commands of the system and opens the designated compartment, the signals and lights will be turned off until the next medication alert time arrives. The unit can optionally be designed to turn off the alert after the drawer is closed. The drawers, as well as the sides or bottoms of the compartments, may be made transparent in order to allow the user to visually check if any pills are in the compartment and to determine the type of medication, if any is present. The drawers, when opened, reveal the majority of their entire length, and have a sloped front, allowing easy access for the patient who may have tremor, arthritis or other difficulties.

If the patient fails to obey the commands of the system and does not open and close each designated compartment within a predetermined interval of time, the audible signal will continue at predetermined periodic intervals, and a visual indication will be provided (e.g. "MISSED MEDICATION"), informing the patient that he forgot to access the appropriate compartment(s), which compartment(s) he forgot to access, and how much medication he forgot to take. The visual alarm and the lights will then be shut off when the designated compartment is opened (or, optionally, opened and closed). The patient may also indicate to the unit that he will be skipping that medication, and the alarm will be cleared.

Generally, any single medication is to be taken periodically throughout the day. The most common schedules will be available within the unit for display, and then selection by the user (e.g. once every other day, once per day, twice per day, three times per day, four times per day). The user must also provide a first dose time. If, for example, the user selects "four times per day", the first alarm will sound at the user selected first dose time, and three subsequent alarms will sound at each four hour interval thereafter. This is in accord with standard prescription labeling and standard or conventional dispensing routines. The user may change the first dose time at will, and all alarms scheduled in this manner will be shifted to match the new first dose time, the following day.

Each compartment may be independently set for one of these standard disposing routines or schedules, or the patient may enter a "special" schedule of up to 12 specific clock times per day that pills should be taken from a given compartment. In this manner, the most common schedules may be set very simply, but the unit is flexible enough to accommodate patients with more complex requirements.

By providing built-in programming which understands the multiple times per day format, the device automatically displays doctor's instructions and translates these into specific pill-taking times and quantity indications for each compartment in sequence. This is accomplished in that the user only needs to bring up onto the display of the device the instructions as written by the doctor, e.g. "three pills four times per day," and confirm the display of this information for the given compartment. The device then automatically, in conformance with its built-in program, translates this into a set of medication alarms such as 8:00 AM, 12:00 PM, 4:00 PM and 8:00 PM. The device also allows for specific programming of pills which need to be taken with meals or at bedtime by allowing the user to program in the patient's usual mealtimes or bedtime, the device can then be instructed to alert for a desired medication at those programmed meal and/or bedtimes. The device also provides for labels for each compartment specifying the doctors instructions so that the display for a specific compartment can be compared to the information on the respective label. Each compartment also instructs the patient as to the purpose of the pill (eg. "heart pill").

The use of a LCD screen allows the patient to be visually prompted during both the programming operation and the medication alert operation of the device. The built-in programming of the device also accommodates a number of confirmation steps, allowing the patient or user to doublecheck the entries before they are stored into the device which provides for more accurate medication monitoring. The many programmable schedule options of the device allow for instructions for "every other day" medication in addition to multiple medications on a given day.

The prompt-then-record system, is taught by the monitor of the present invention. Here the device displays an instruction, and does not record an instruction until it is confirmed; it requires a response or acknowledgement to a prompt, (such as a medication alert) prior to recordation that the event took place, so that the event may be recorded as an "acknowledged" event to indicate pills taken. If the patient does not acknowledge the prompt, the event is recorded as unacknowledged or "missed", which is then displayed to the patient, thereby increasing the accuracy of the medication monitoring. The prompt-then-record can also be utilized to record and indicate other normal or abnormal patient behavior with respect to the medication schedule.

The device has a number of manually operable switches or buttons that are used to set proper operating conditions, and to interact with the device during it's operation. The user is prompted by words and phrases, on the built-in display, to simplify setting of the device. The embodiment of the invention illustrated and described herein includes user-input buttons on the front panel of the device adjacent the display. The first two buttons of the display are the "Next" and "Last" buttons, described in more detail below, which allow prospective and retrospective review of the medication schedule, respectively. These buttons also allow cycling forward or backward through the different options within the various programs available within the device, such as the time of day options described above. The buttons are arranged closely adjacent one another so that the user can readily identify their similar functionality and can readily switch forward and backward between the options of the given programming mode. Providing the "Next" and "Last" buttons allows ease of programming over devices which simply provide for a common mode cycling button, while allowing for simplified design over devices which require multiple buttons, each for a specific task. The patient can readily master the next/last sequencing logic which carries throughout the various programming modes where these buttons are utilized in a common manner.

The next set of buttons is the "YES/OKAY" and "No" buttons. These buttons are utilized by the patient to answer queries or provide acknowledgements. As these buttons are similar in their functioning and there is interplay between their applicability, they have been grouped together to provide easier user mastering of the utilization of the device. Use of the "no" button also allows the patient to suspend the audible tone for predetermined time periods by holding the "no" button down for 1 second or more.

The last group of buttons is the "Check and Set" buttons. These buttons can be grouped by placing them in close proximity to each other, however in the exemplary embodiment described herein, these buttons are associated by color not proximity. The "Check" button allows cycling between the different modes of the apparatus, e.g., time of day, first dose time, compartment scheduling, etc. The "Set" button allows the patient or user to enter one of these programming modes and then alter the programming within the mode. By closely associating these two buttons, the patient or user readily becomes familiar with their interaction and therefore, the programming is made more easily accessible.

As stated above, the visual and audible medication alert signals, are turned off when the patient opens the compartment. This operation is carried out by having a separate closure (for example a lid) for opening and closing each compartment or by providing drawers within each compartment which slide out for access. When the lid or drawer is moved to open the compartment, a switch operating through the electrical circuitry of the signaling system, turns off the visual medication alert signal and/or the audible alarm. The drawers may be removed for easy cleaning.

The electronic circuitry of the unit may be realized in many ways. One embodiment using a 4-bit microcontroller integrated circuit, the Hitachi HD407L4808, and some associated components, such as light emitting diodes (LEDs), a liquid crystal display (LCD), resistors, capacitors, batteries, etc., is illustrated herein.

The microcontroller continually operates in a low power mode with a 32 kHz clock crystal, and each half second an interrupt is generated to change the state of the colon (such that the colon is continually blinking, on for one half second and then off for one half second), incrementing the time keeping circuitry and keeping track of the time of day. The time of day may be shown on the unit's display. The time of day is continually compared against the scheduled medication times, and, when a match is found, an output of the microcontroller is enabled to turn on the light associated with the appropriate compartment, and other outputs are set to enable the audible signal and to show the number of pills on the display associated with that compartment.

The opening and closing of the various compartments is sensed by the microprocessor through the actuation of individual switches associated with each compartment. Each medication alert and associated taking or skipping of medication is stored in the microcontroller's random access memory (RAM), so that the patient can later review when and if pills were presumably taken or skipped.

If desired, the audible signal may include the use of a transducer which emits speech giving special instructions to the patient relating to the taking of the medication.

By pushing a single button, the patient may, at any time, examine the schedule of medications to be taken over the next period (e.g., 24 hours). By pressing another button, the patient may review the actual times that doors were opened (and medication presumably taken) over the previous period (e.g. 24 hours). The memory storing the prospective and retrospective information may be extended, by use of additional RAM, to provide a longer time period for review, and an electronic output may be provided so this information can be directly transferred to a computer or to a printer for analysis by a pharmacist, physician, family member or other interested party.

If a compartment is opened when no pill is scheduled, the unit "chirps", and displays a question to the patient to determine if he is taking an unscheduled pill, in order to prevent the unit from recording that a pill was taken when a patient merely opens a door to check the pills or to refill a compartment. If the patient responds negatively (pushes "No") or does not respond at all, the compartment opening is not recorded and the device assumes that the compartment was opened for checking or refill. The unscheduled pill taking is recorded in the unit's memory only if the patient responds positively (pushes "Yes/OK").

The unit can also include a plurality of other user input buttons arranged so that buttons are grouped according to common function. This allows the user to readily identify related buttons for desired sequencing.

During programming, the unit can also display specific doctors orders on the LCD and query the patient as to whether the patient is programming in conformance with those orders.

The unit can also display a specified medication identification on the LCD for the user to compare against the medication bottle, or label on the medication compartment, and indicate if it is the same by supplying a "YES/OKAY" or "NO" answer to the device. If the user selects "YES," the identification is stored. If "NO," the display is altered until the desired identification is displayed.

By pushing a button, the patient can suspend the audible alarm. Each push of the button suspends the audible alarm for a predetermined time period (e.g. one hour). The LCD displays a symbol that indicates that the audible tone has been suspended, while the visual alarms and prompts continue to operate as programmed. If the patient is going into a concert or meeting and does not want the device to interrupt, he can suspend the audible alarm. When he leaves the concert and references the device, it will indicate the type and quantity of medication missed and when it was to have been taken, via the visual means which was not suspended.

The volume of the audible tone can also be programmed in by the patient to suit their wishes.

One button, "Check" allows the patient to review and display what has been programmed into the device. With any display then showing, the push of a second button "set" allows the device to enter the "programming mode" wherein the particular program is displayed and flashing, and can be altered through the push of other buttons ("NEXT" and "LAST"). In this programming mode, the device queries the patient as to whether each new program displayed is "OKAY," and patient can indicate "YES/OKAY" or "NO". "YES/OKAY" enters the new program into the device. Pressing "no" allows the patient to push buttons to display yet a different program on the device, until the correct program is displayed, wherein the pressing of the "yes/okay" button then locks in the correct program into the device. This sequential pushing of buttons to reprogram the device helps to prevent inadvertent alteration of the programming (e.g. through buttons being pushed by a child or inadvertently pushed when the device is placed in a handbag).

At any time if the programming routine is interrupted for more than one minute, or if buttons are pushed inadvertently, the device will automatically return to "time of day," and the interrupted programming will not be entered, as the user did not press the "YES/OKAY" button.

A "low battery" prompt appears when it is time to change batteries. When batteries are removed for changing, the device retains its programming for several minutes.

To help extend battery life, the audible tone beeps only once at alarm time; if the patient does not access the appropriate drawer within one minute, the tone then beeps for an extended ten seconds as a longer reminder to the patient; if patient still doesn't access the appropriate compartment, the unit beeps once every five minutes. Until the appropriate compartment is accessed by the patient; or until the next alarm cycle for that compartment, the device will continue to instruct the patient by displaying the LCD quantity indicator and flashing the LED over the appropriate compartment(s).

BRIEF DESCRIPTION OF THE DRAWINGS

For a better understanding of the nature of the present invention, reference is had to the following figures and detailed description, wherein like elements are accorded like reference numerals, and wherein.

DETAILED DESCRIPTION OF AN EXEMPLARY EMBODIMENT

Figure 1:
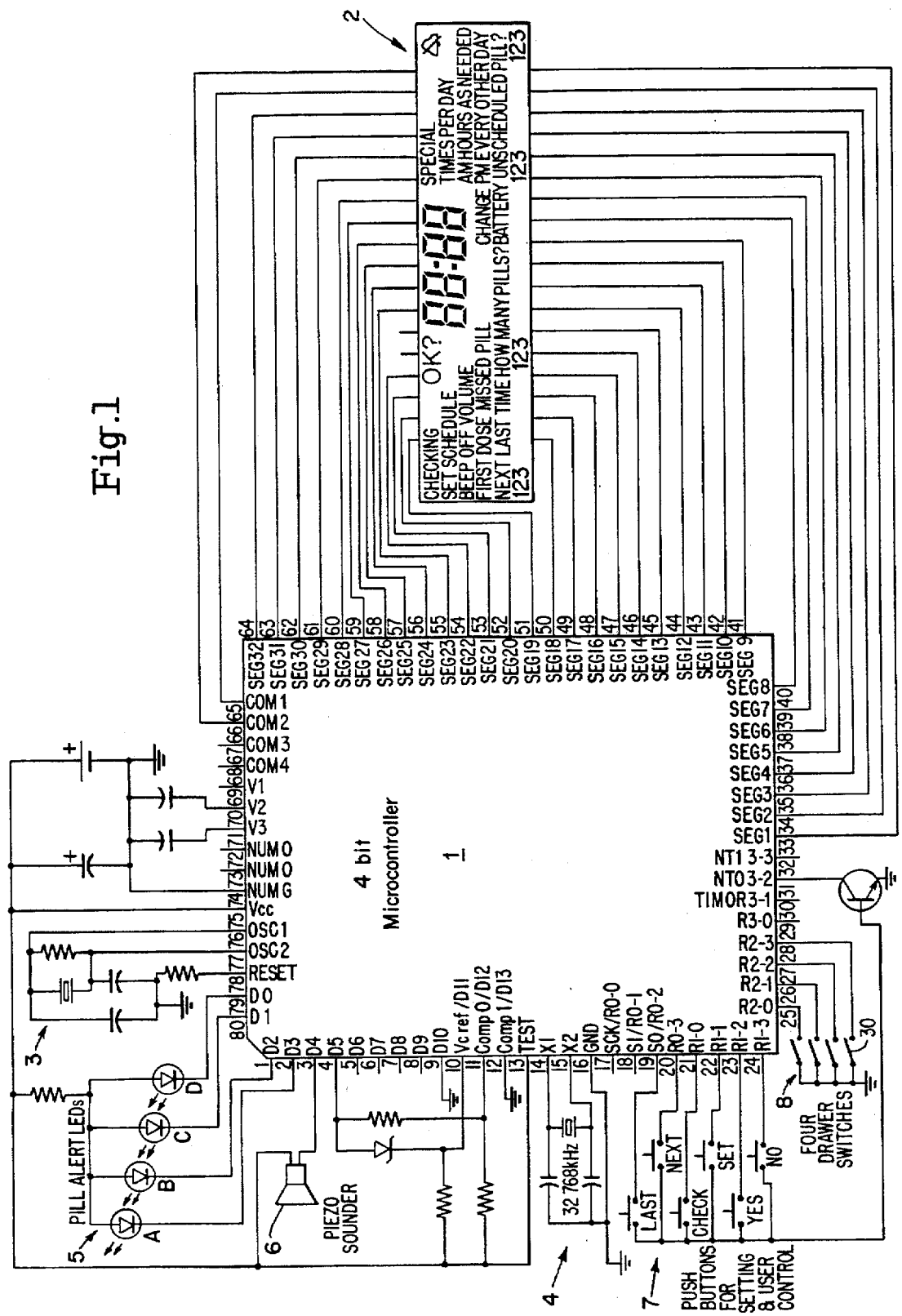
FIG. 1 is a circuit diagram of the medical monitoring device.

As illustrated in FIG. 1, the present invention utilizes an Hitachi Model HD4074808 microcontroller chip 1 for accepting user inputs and for performing the necessary logic for driving the liquid crystal display 2 and associated medication alert signals.

The microcontroller 1 is a MCU microcontroller utilizing a 4-bit architecture and having built-in ROM and RAM. The chip includes a 16 digit LCD driver and 30 Input/Output (I/O) ports. The ROM portion of the microcontroller 1 is programmed according to the program contained in the microfiche appendix of this application. The microcontroller 1 is also provided with a crystal oscillator circuit 3 for supplying the internal clock and timing circuits for proper operation of the microcontroller 1. The chip is also provided with a clock crystal circuit 4 to enable the chip to accurately track the time of day in order to display the necessary medication alerts at the appropriate times.

In addition to the liquid crystal display 2, a series of light-emitting diodes (LEDs) A–D are provided in circuit 5, which, along with Piezo buzzer 6 are, attached to. I/O ports of the microcontroller 1. A series of push buttons 7, as well as a series of drawer switches 8, are connected to the 4-bit I/O ports of microcontroller 1. The liquid crystal display 2 is attached to the common and segment driver pins of the microcontroller 1.

Figure 2A:
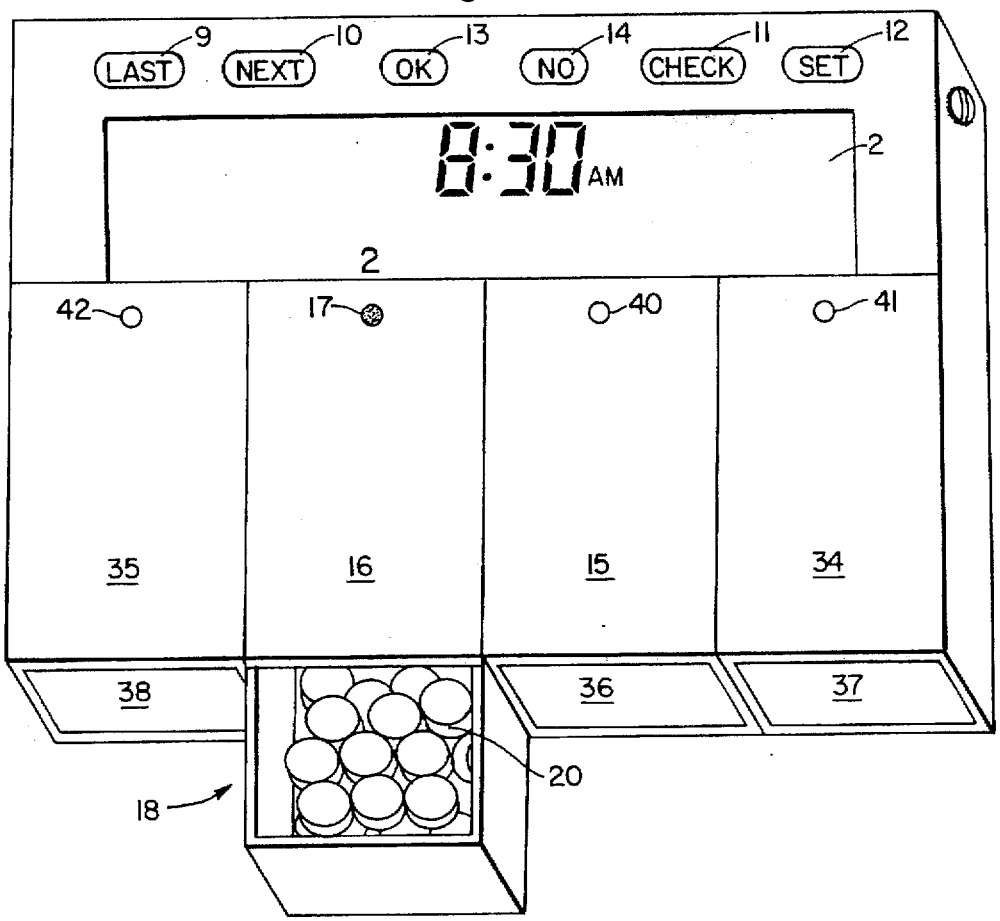
FIGS. 2A and B are perspective views of the monitoring device.
Figure 2B:
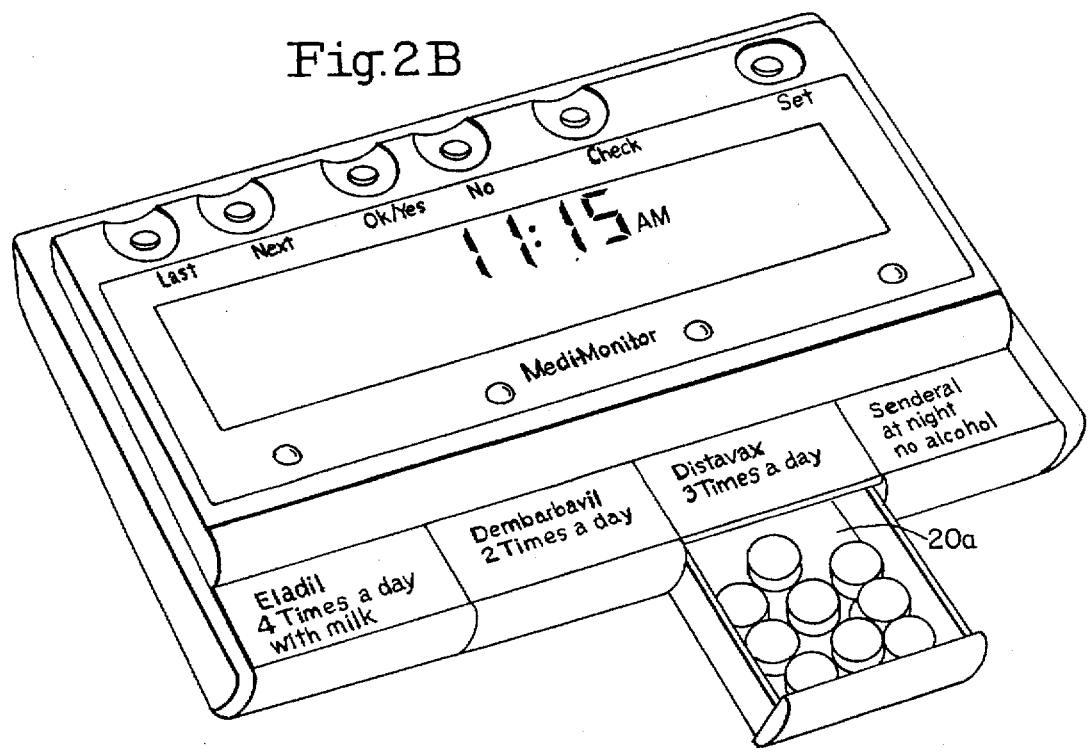

As illustrated in FIG. 2B, the buttons positioned above the display 2 are seated in recesses in the top panel of the housing. The recesses are shaped for accommodation of the operator's finger to ease actuation of the buttons and to help prevent pressing of the wrong button or more than one button simultaneously by recessing the actual buttons from the top surface itself, inadvertent actuation of the buttons is greatly reduced.

Figure 3:
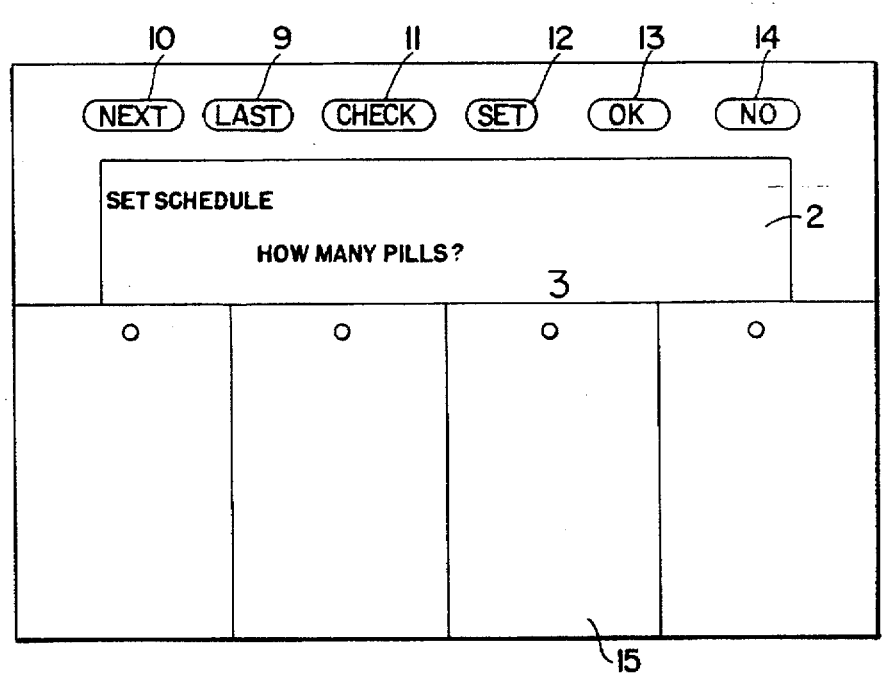
FIG. 3 is a top view of the device with the liquid crystal display illustrating one step of one of the programming modes of operation.
Figure 4:
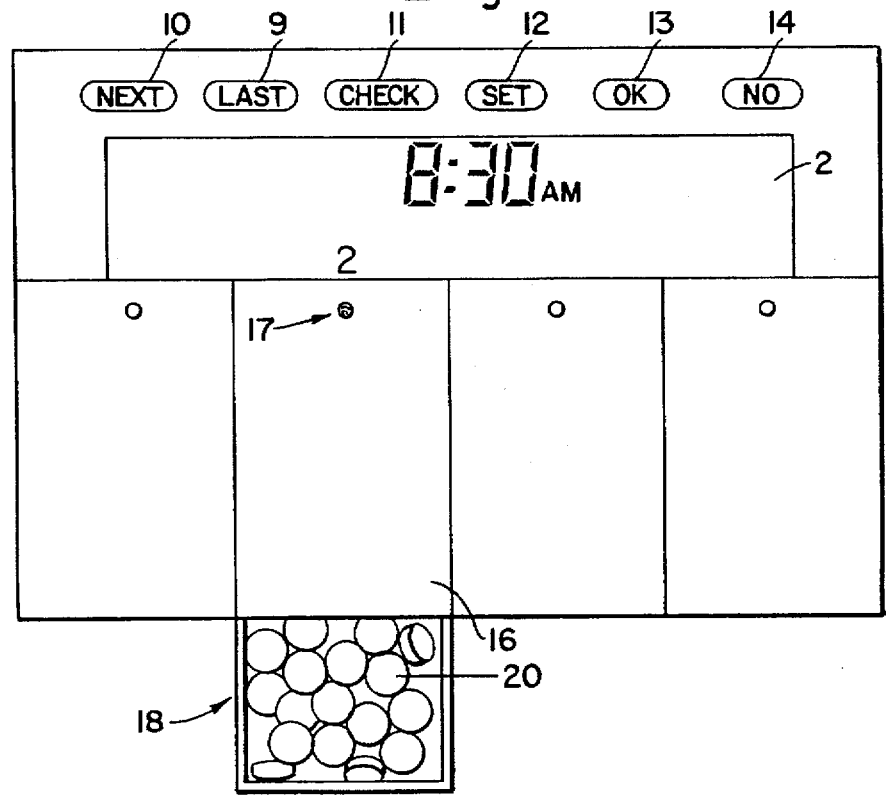
FIG. 4 is a top view of the device with the liquid crystal display indicating the time of day and displaying a pill-taking prompt.

The pill box itself, as illustrated in FIGS. 3 and 4, has a top face on which is positioned the LCD display 2 as well as push buttons 9, 10, 11, 12, 13 and 14. During programming, the LCD display will display a variety of messages. One set of messages is utilized to prompt the user into providing appropriate information to the microcontroller 1. This information is needed by the monitor to establish the appropriate medication schedule. FIG. 3 illustrates an example of the monitor displaying a request for user inputs in the "set schedule" mode displaying the prompt "How many pills?" to request a pill number input from the user.

The pill number "3" is also currently displayed above the third pill box compartment 15, indicating a response from the user. If this setting were accepted, that would instruct the monitor to remind the user to take three pills from compartment 15 at a designated time. As discussed in greater detail below, the number of pills, the medication alert time and the designated compartment can be selected through the operation of push buttons 9–14.

In FIG. 4, the time of day is displayed on the LCD display 2 as well as a digit "2" above compartment 16. Further, the LED 17 associated with compartment 16 is actuated. This combination of an actuated LED 17 and a display of a digit "2" is an indication to the user that two pills should be taken from the drawer 18 located within compartment 16. The drawer 18 is illustrated in the open position exposing pills 20 therein so that they may be taken by the user.

FIG. 2A illustrates an exemplary embodiment of the monitor with four compartments 16, 15, 34 and 35, each compartment having a drawer 20, 36, 37, 38 and an LED 17, 40, 41, 42 respectively. The user is prompted to open a designated drawer in a designated compartment by activation of the LED corresponding to the appropriate compartment. The lower face 20a of each compartment can be made of a transparent material, as better illustrated in FIG. 2B, so that the user may readily determine if any pills are stored in each drawer and to identify the medication by sight, simply by viewing from the lower side of the device without the necessity of opening each drawer.

Figure 5A:
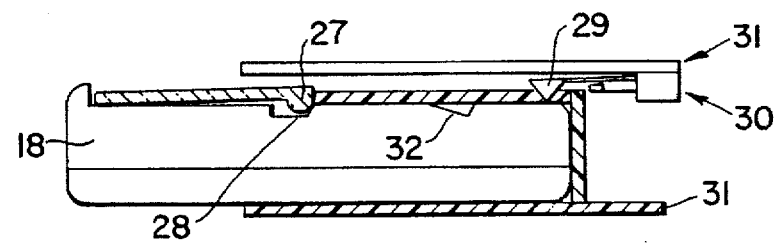
FIGS. 5A–5D are side cross sectional views illustrating one pill compartment of the device.
Figure 5B:
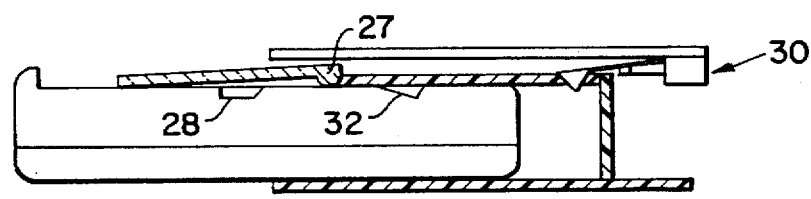

FIGS. 5A–5d illustrate the opening and switch actuation mechanism of the drawers. When drawer 18 is closed, as illustrated in FIG. 5A, a detent arm 27 attached to compartment 16 is engaged in the detent notch 28 in drawer 18. The detent restraint pressure is easily overcome by slight pulling force on the drawer 18. As drawer 18 is opened, plunger 29 of microswitch 30 mounted on the housing 31 drops thereby closing microswitch 30. Microswitch 30, illustrated in FIG. 1 as part of the drawer switch circuitry 8, when closed grounds terminal R2-1. The grounding of the particular terminal associated with a particular drawer provides a signal to the microcontroller to deactivate the current medication alert which is associated with that drawer.

Figure 5C:
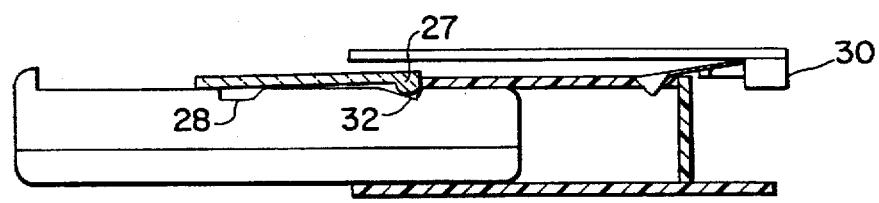
Figure 5D:
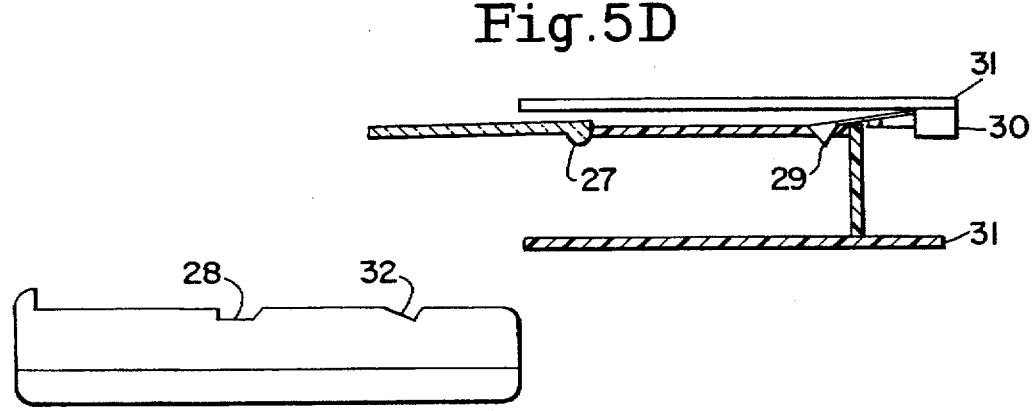

As the drawer is further slid open, as illustrated in FIG. 5C, the detent arm 27 lodges in second notch 32 of drawer 18. The lodging of detent 27 in second notch 32 holds the drawer in an open position in order to facilitate pill removal. The drawer 18 can be completely removed from the housing 31, as illustrated in FIG. 5D, for refill, cleaning or other purposes.

When drawer 18 is pushed back to its closed position, post 29 of microswitch 30 will be deflected thereby reopening microswitch 30. The reopening of microswitch 30 provides a signal to microcontroller 1, indicating that the drawer has been closed.

When the compartment 18 is open and switch 30 closed, the microcontroller 1 is instructed to discontinue the medication alert signal such as that illustrated in FIG. 4. The time at which the switch 30 was closed, indicating the opening of the compartment 18, is stored in the microcontroller's random access memory (RAM). Each time the drawer is opened, the time of opening and the particular drawer opened is recorded in the microcontroller's RAM. If a take medication signal is generated and the corresponding drawer is not opened at that time or within a predetermined time period thereafter, this is also stored in the microcontroller's RAM as a missed pill event, along with an indication of time and the number of pills that should have been taken, with an indication displayed on the LCD display 2 that the corresponding drawer was not opened at that time. All of this information is stored in the RAM so that it can later be accessed by the user to review the taking of medication and the missing of medication.

The microcontroller 1 keeps track of time and updates the time of day display on the LCD display unit 2. The current time of day of the microcontroller 1 is continually compared against the stored times for scheduled medication. When this comparison generates a match between the stored scheduled medication times and the actual time of day, the microcontroller 1 enables one of the output terminals to the appropriate LED of the LED set 5. Simultaneously, the corresponding segment driver outputs are enabled to indicate the number of pills that should be taken from the designated compartment at that medication time. Further, if not disabled by the user, the audible alarm is also triggered.

Figure 6:
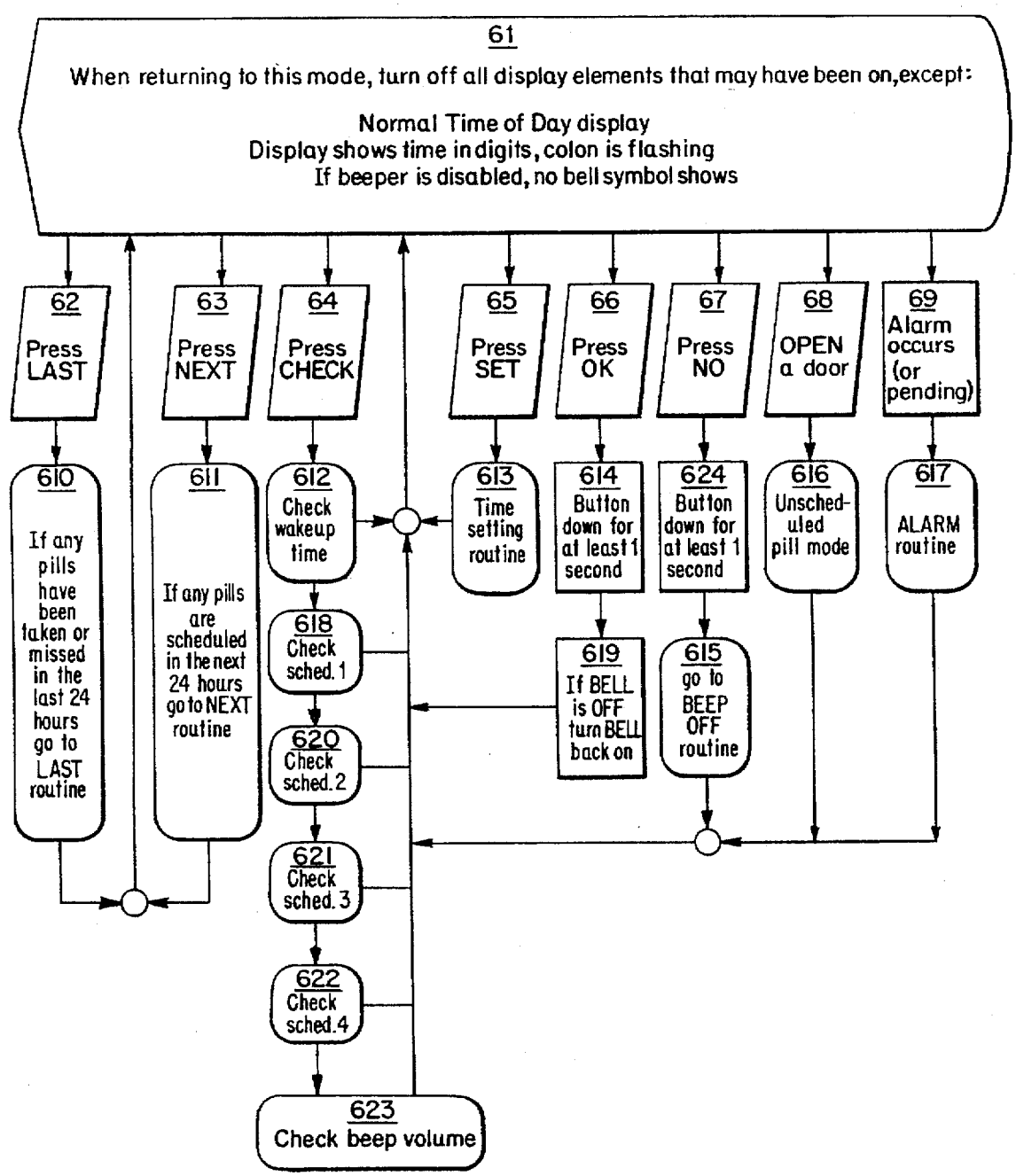
FIGS. 6–16 are logical flow diagrams illustrating the logical operation of the medication monitor device of the present invention.

The logical operation of the microcontroller will now be described with reference to FIGS. 6–16. FIG. 6 is an overview of the logical operation of the various monitoring routines of the monitor. Block 61 of FIG. 6 illustrates the standard resting or time-of-day mode for the microcontroller operation. This is the mode to which the microcontroller returns when no other function is being performed. In this mode, the liquid crystal display 2 displays the time of day and a flashing ":" to indicate that the monitor is operating. Blocks 62–68 illustrate the various user inputs which can be detected by the microcontroller. Blocks 62–67 correspond to the push buttons 9–14, respectively, which are illustrated in FIGS. 2, 3 and 4 on the top of the monitor housing. Blocks 68 and 69 correspond to the input received when a drawer is opened or when a scheduled time is reached, respectively.

Figure 11:
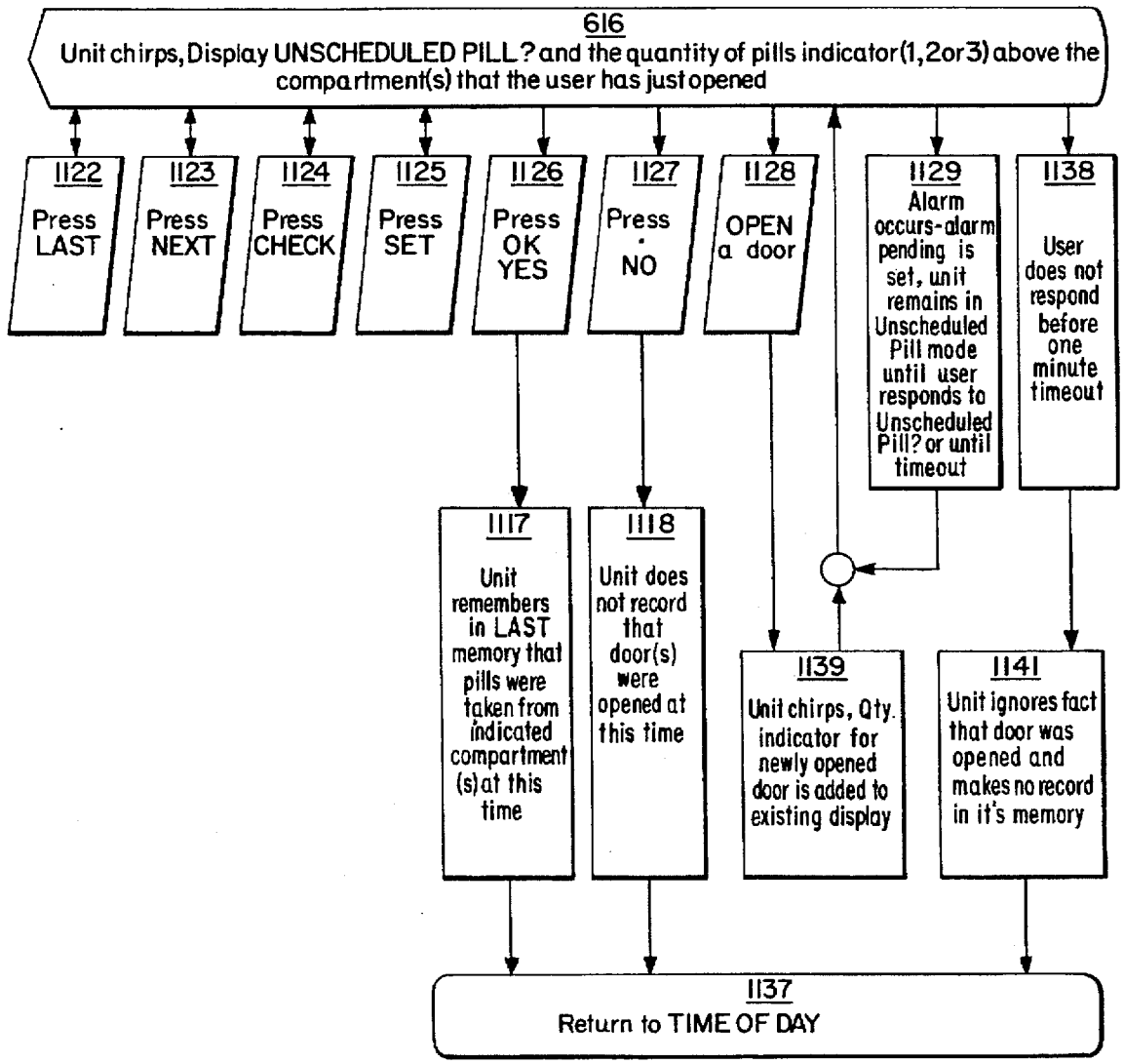

If a drawer is opened while the microcontroller 1 is in this mode, as illustrated by block 68, the microcontroller will jump to the unscheduled pill routine designated by block 616 and further detailed in FIG. 11.

Figure 12:
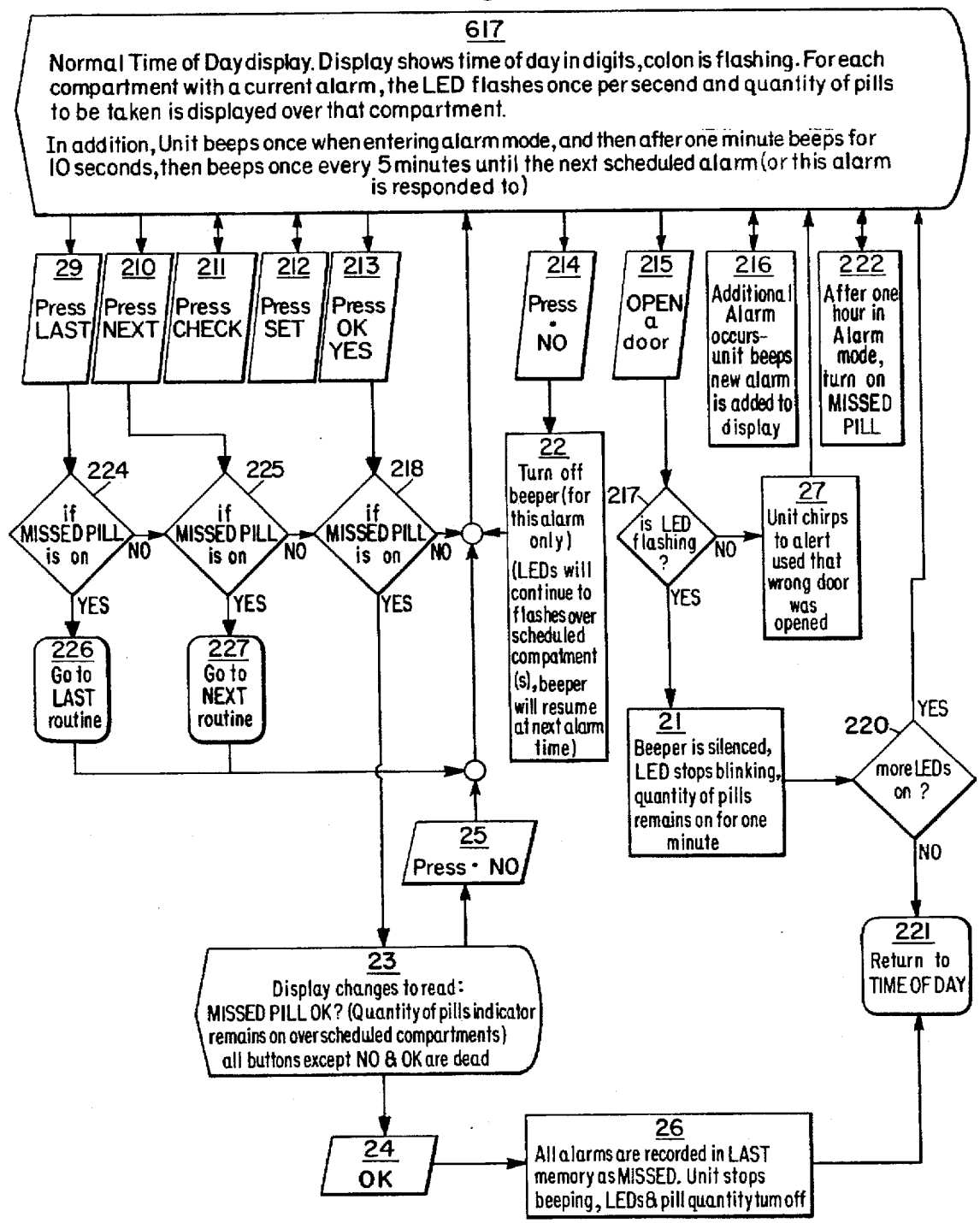

If an alarm occurs or is presently pending, as illustrated by block 69, the microcontroller 1 will jump to the routine illustrated by block 617 and further detailed in FIG. 12. The alarm routine is, therefore, entered through the internal generation of the correspondence between a scheduled medication time and the current time of day of the microcontroller 1. The unscheduled pill routine is entered through the enabling of one of the inputs connected to the drawer switch circuitry 8 as illustrated in FIG. 1. This occurs when a drawer is open and the corresponding switch is triggered without the user first being prompted by the occurrence of a scheduled medication alert through the running of the alarm routine.

Actuating one of the user input buttons 9–14, will cause the microcontroller 1 to enter the appropriate corresponding routine. Actuating the "YES/OKAY" button 13, as illustrated by 66, and maintaining the button actuated for at least one second will cause the audible alarm to be reactivated if it has been suspended. Maintained actuation of the "NO" button, as illustrated by blocks 67 and 624, will cause the audible alarm to be deactivated. Actuation of the "set" button 12, as illustrated by block 65, will cause the microcontroller 1 to enter the time setting routine better illustrated in FIG. 10. Once the time setting routine has been completed, the microcontroller 1 will return to the time of day display mode as described above.

Figure 7:
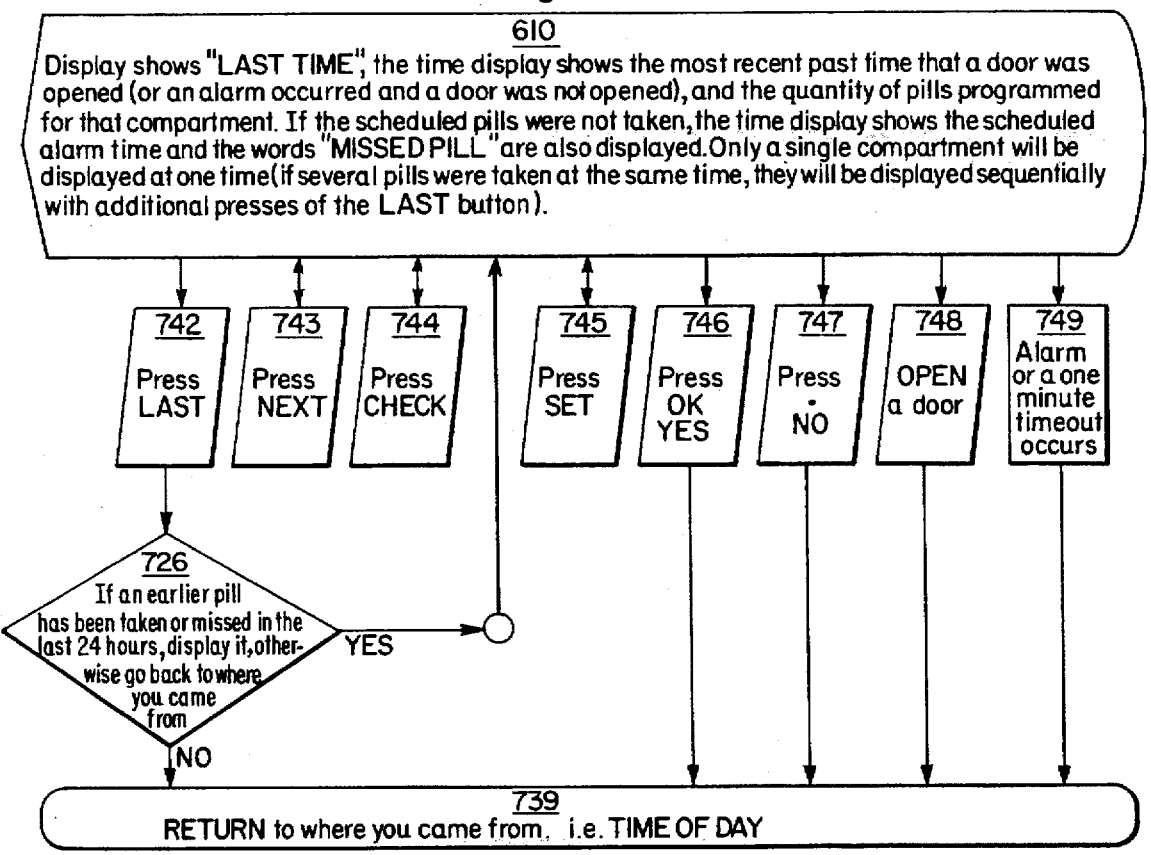
Figure 8:
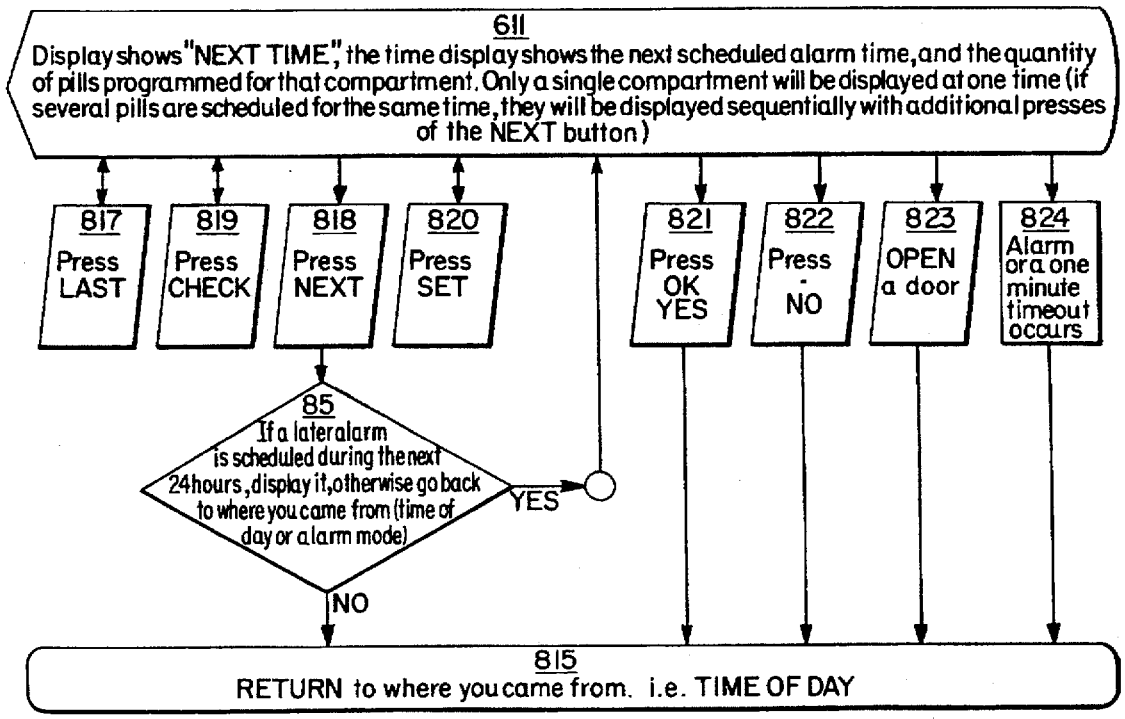

Actuating the "LAST" button 9 or the "NEXT" button 10 will cause the microcontroller to display the last 24 hours of access to the drawers including; medication taken on schedule, missed medication, and unscheduled compartment openings; or the next 24 hours of scheduled medication, respectively, by entering the last routine, FIG. 7, or the next routine, FIG. 8, respectively.

Figure 9:
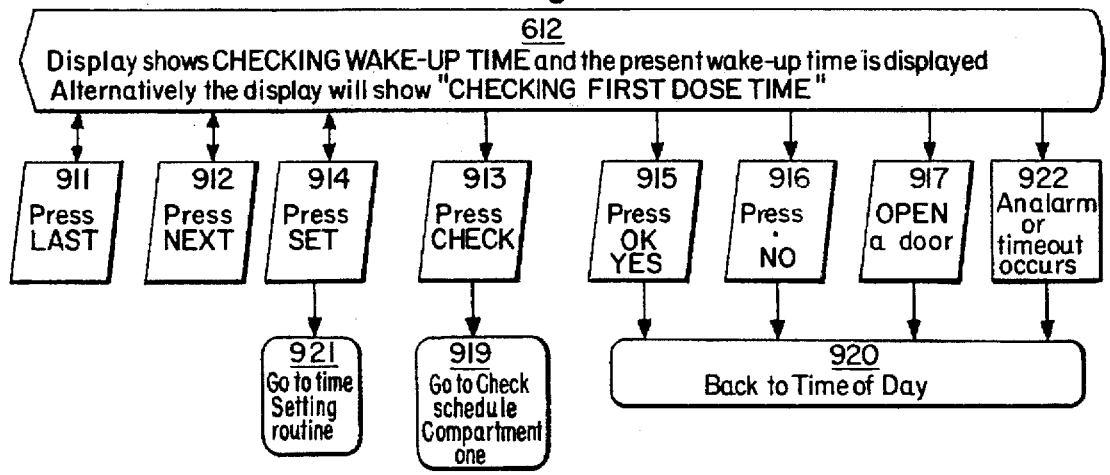

Actuation of the "CHECK" button 11 will cause the microcontroller 1 to go into the First-Dose-Time routine as illustrated by block 612 and in greater detail in FIG. 9. As illustrated in both FIGS. 6 and 9, the user can elect to go to the check schedule routine, block 618, or to return to the time of day display. The check schedule routine, illustrated in detail in FIG. 13, allows the user to check the scheduling stored in the microcontroller 1. It also enables user to cycle through checking "BEEP VOLUME" and "TIME OF DAY".

When in the "LAST" routine, as illustrated in FIG. 7, the display 2 initially indicates the most recent time that a compartment was opened, or a take medication alert was generated. The display also indicates the number of pills, and the compartment corresponding to the particular scheduled medication. If a medication signal was generated, and the appropriate compartment was not opened in a predetermined time period (e.g. 10 minutes or 1 hour), the LCD will also display a "missed pill" indication, corresponding to that scheduled medication alert. If a number of medication alerts or unscheduled openings of a drawer occurred simultaneously, each of the medication signals will be displayed sequentially, through sequential actuation of the "LAST" button 9, while the time indication of the time of each of these events remains the same.

Actuation of the "LAST" button 9 during this routine will continue to sequence through each of the last occurrences during the previous 24 hours, displaying each occurrence after each actuation of the "LAST" button 9, until the entire previous 24 hours of activity of the device has been replayed. Once the full 24 hours has been displayed, actuation of the "LAST" button 9 will take the flow of the microcontroller 1 back to that location in its operation prior to the initial selection of the last routine, or return to "TIME-OF-DAY".

During the "LAST" routine, actuation of the "NEXT" button 10, the "CHECK" button 11 or the "SET" button 12 will have no effect on the operation of the microcontroller 1 or the display 2. Actuation of the "YES/OKAY" button 13 or the "NO" button 14 or the opening of one of the compartments or the occurrence of a medication alert time will cause the last routine to terminate and the microcontroller to return to that location in its operation prior to the initial selection of the last routine, or return to "Time-of-Day".

FIG. 8 illustrates the "NEXT" routine, which is similar to the "LAST" routine above. In this mode, each designated medication time for each compartment, with each quantity of medication, over the next 24 hours is displayed through sequential actuation of the "NEXT" button 10. Once all of the scheduled times have been displayed for the next 24 hour time period, the microcontroller 1 is sequenced back to that location in its operation prior to the initial selection of the next routine, or returned to "Time-of-Day". The "LAST" 9, "CHECK" 11 and "SET" 12 buttons are rendered ineffective during the "NEXT" routine. Actuation of the "YES/OKAY" 13 or "NO" 14 button or the opening of one of the compartments or the occurrence of an medication alert time will cause the next routine to terminate and the microcontroller 1 to return to that location in its operation prior to the initial selection of the next routine, or return to "Time-of-Day".

The provision of these two routines allows the user or other monitoring personnel to prospectively view the programmed medication times for the next 24 hour period and to retrospectively view the medication administered or missed during the last 24 hours. The device is therefore not limited only to medication reminding but also allows for medication monitoring. Through the extension of the internal RAM storage of the microcontroller 1, information covering a time period greater than 24 hours can be stored. An optional data port 33 can be provided to supply this prospective and/or retrospective information to a external device such as a printer, a data storage medium, a computer or other device.

Figure 10:
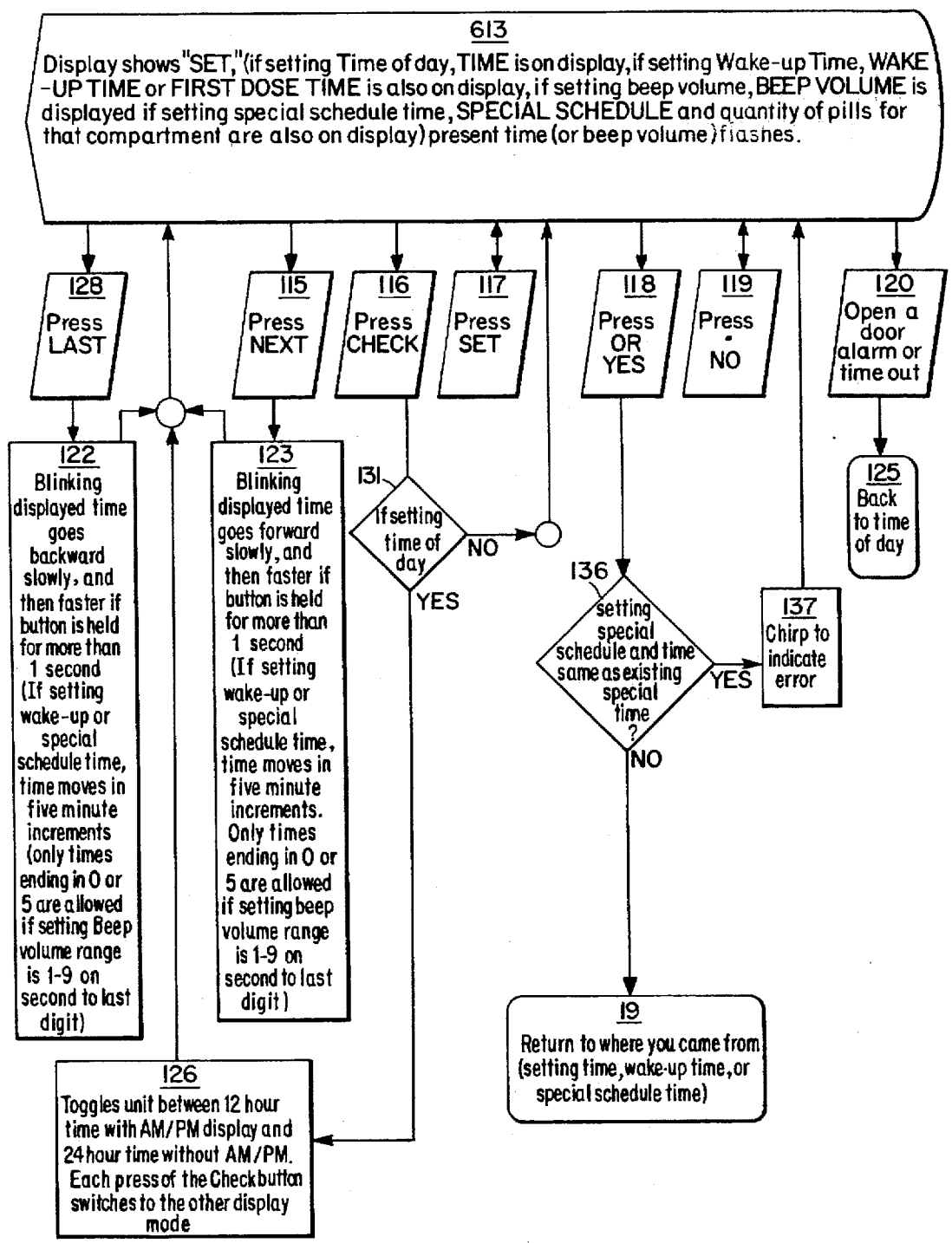

The Check First-Dose-Time routine, FIG. 9, displays the preset First-Dose-Time and allows it to be changed by entering the time setting routine block 921, FIG. 10, by actuation of the "SET" button 12. From this routine, the medication alert schedule can also be viewed by actuation of the "CHECK" button 11. The Processor will then proceed with the check schedule routine, FIG. 13.

FIG. 10 illustrates the time setting operation of the microcontroller 1. This routine is used to set the Time Of Day, to set the First Dose Time, and to set the Special Scheduled medication times. Special schedule medication times are those which must be set at a particular time, for which the built in time increments such as "every-four-hours" will not provide. Therefore these times need to be specifically input. This routine is entered from each of these functions as appropriate to the performance of that function. When in the time setting routine and Set First Dose Time routine, actuation of the "NEXT" button 10 increments the time and actuation of the "LAST" button decrements the time.

The Unscheduled Pill routine, FIG. 11, is entered when a drawer is opened at a time other than a scheduled medication time. This routine causes the display 2 to display the appropriate quantity of pills for the drawer that was opened. The user is prompted via an audible "chirp" and the query "UNSCHEDULED PILL?" to indicate whether or not an unscheduled medication is being taken. If the user actuates the "YES/OKAY" button 13 the microcontroller 1 will record that an unscheduled medication was taken. If the user does not respond within a predetermined period of time, or if the user actuates the "NO" button 14, the microcontroller will assume that no medication was taken. Each incidence of unscheduled medication is recorded for later review and display as described above in the "NEXT" and "LAST" review routines.

The alarm mode block 617 of FIG. 12 is entered when the scheduled time and the time of day correspond. If the drawer of the compartment containing the correct pills is opened, the alarm condition is satisfied. If more than one compartment needs to be accessed, all compartments must be opened in order to satisfy the alarm condition. The user is prompted as to which drawers must be opened by the activation of the LED corresponding to the compartment and the indication of pill quantity above the compartment. If a wrong drawer is opened, the unit chirps to help prevent improper medication taking at an alarm time.

The user is also prompted if medication has been missed and can then view this missed medication through actuation of the "LAST" button 9 and can view the next medication by actuation of the "NEXT" button 10. The user can then decide to take the missed medication or not and so inform the microcontroller 1 by actuation of the "YES/OKAY" button 13 or "NO" button 14.

Figure 13:
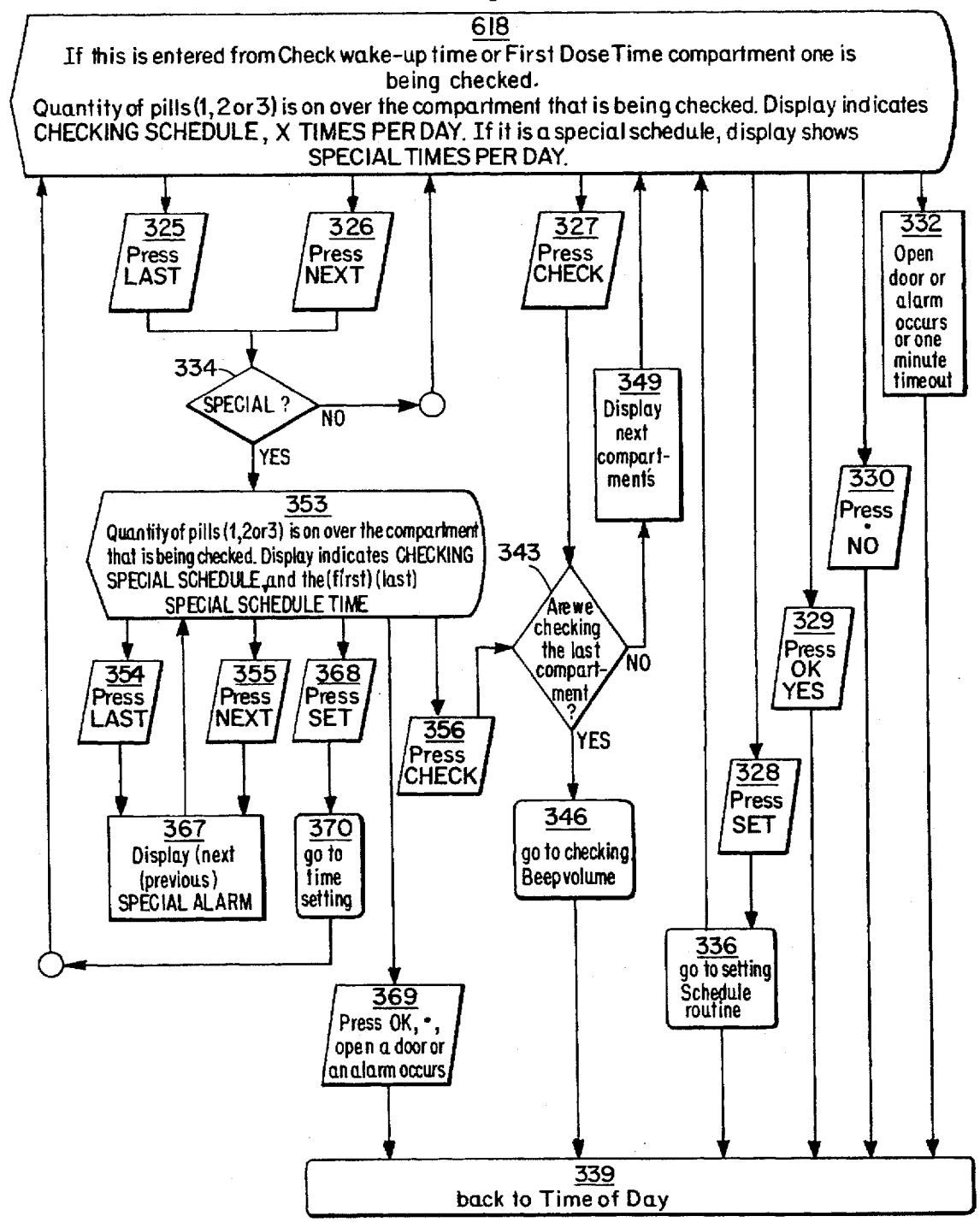

The Check Schedule Routine FIG. 13 allows the user to sequentially view the scheduled medication times by actuation of the "LAST" and "NEXT" keys. The schedule and quantity of medication is displayed in the same manner as the information was entered. For example, if the medication was entered as "2 pills 4 times per day" the display will reflect this scheduling. If specific special alarm times were entered, the display would indicate "2 pills 7 special times per day" and the "NEXT" and "LAST" buttons would allow display of those seven special times. Further, the LED of the appropriate compartment is activated.

Figure 14:
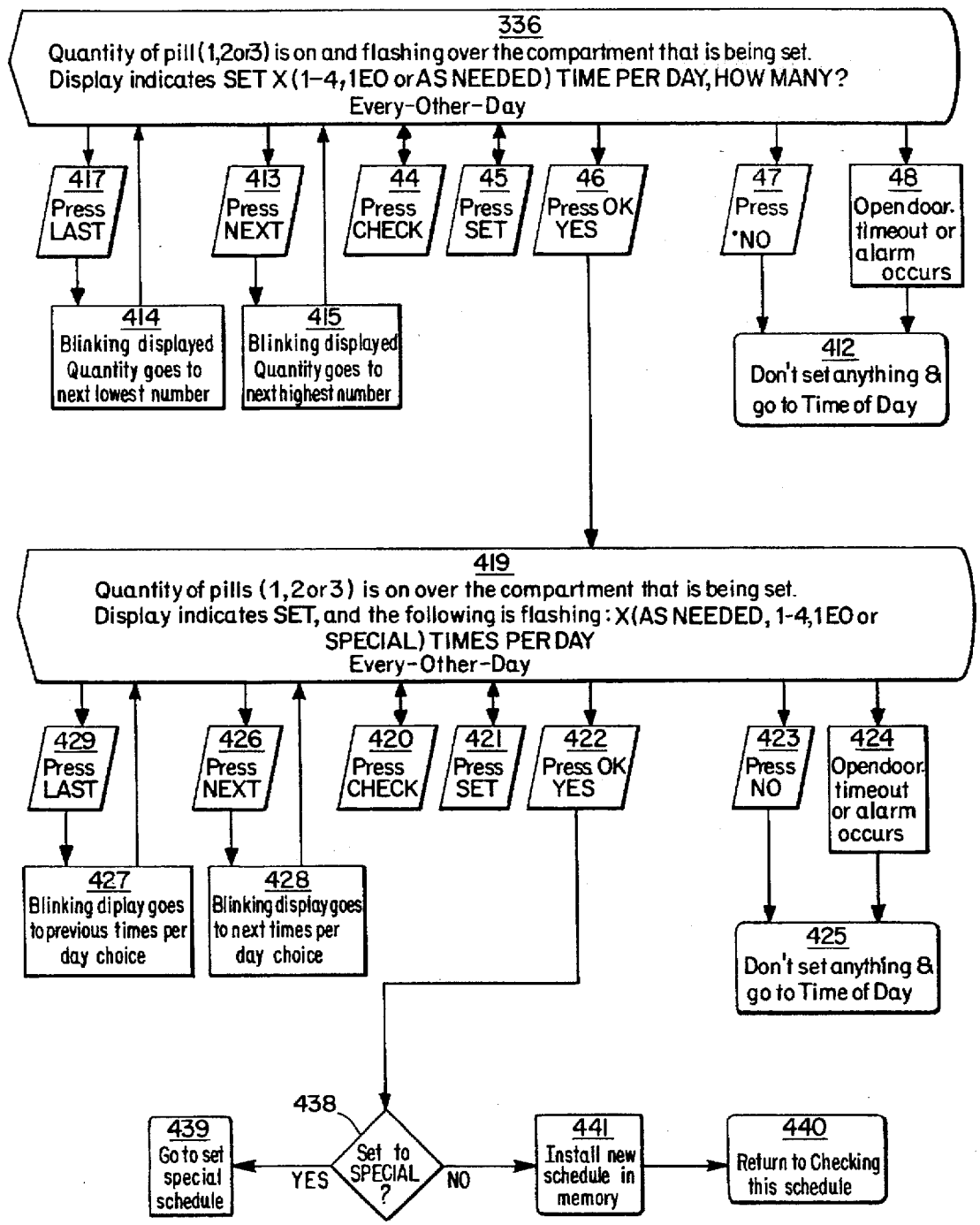

FIG. 14 illustrates the logical operation of selecting the quantity of pills to be taken and selecting one of the preset, i.e. non-special, times per day settings for medication alerts.

Figure 15:
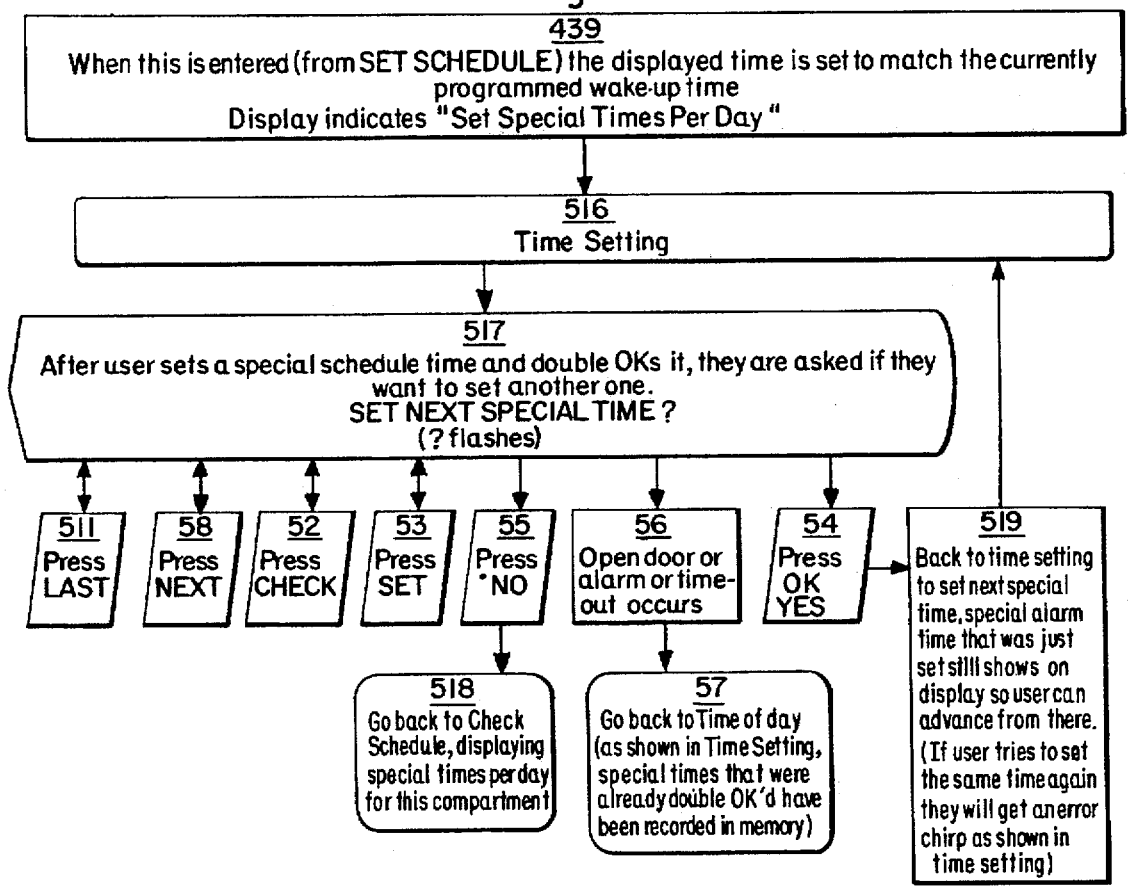
Figure 16:
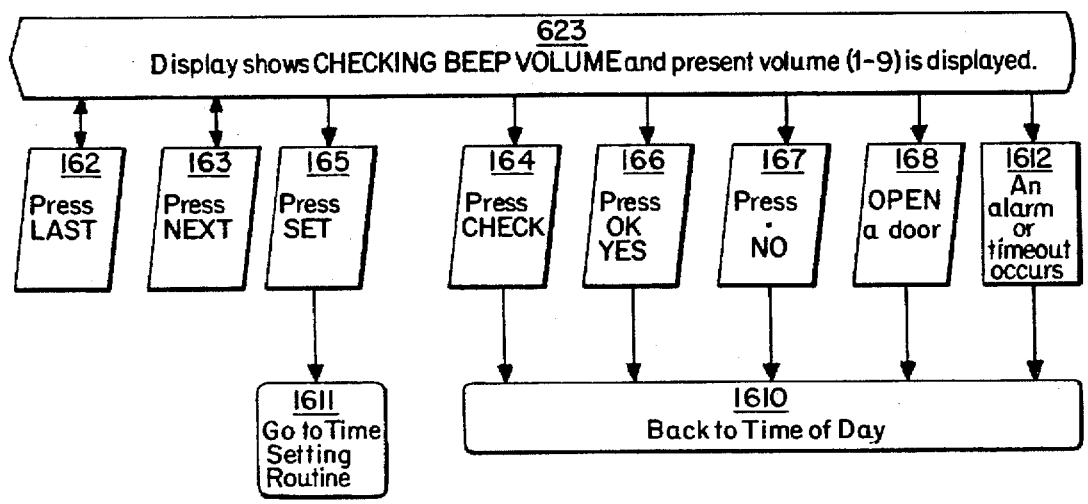

The set special schedule routine, FIG. 15 is a special case of the time setting routine, which, when entered allows the user to establish a non-standard medication alert time. Once this routine is entered, the patient or user can enter the specific times of day that medication should be taken allowing greater flexibility than simply choosing one of the preset standards of "three-times-daily" etc.

The "Set Beep Volume" Routine displays "SET BEEP VOLUME", the operator pushes set and uses the "Next" and "Last" buttons to adjust the volume from softest (1) to loudest (9).

It is to be understood that the above embodiment and description is exemplative of one preferred embodiment of a medication monitor according to the inventive concept of the present invention. The disclosure is to be interpreted in an illustrative and not a limiting sense. The scope of the invention is defined in the following claims.

APPENDIX A
Object code for the microcontroller
Title:
ELECTRONIC MEDICATION MONITORING AND DISPENSING METHOD
Inventors:
Bruce A. KEHR
Richard D. DEMENUS
David LERNER
Michael J. EDL MediMonitor program for Hitachi 4bit Microcontroller HD4074808 in Hex Format
Copyright ©1989, 1990 Current Designs Corporation, New York, NY
Medi-Monitor Corporation, New York, NY                                    page 1

```
S00B0000505348574150202OE1
S1230200F3F4F2F4F3F4E5ECE7E3F0FEE0E0E0E0E3EDF0E2F3F4F2F4E5ECF6E2F8FEE0E04F
S1230220F1F4F0F4F1F4E9ECE7E3F0FEE0E0E0E0E1EDF0E2F1F4F0F4E9ECF6E2F8FEE0E033
S1230240F2F4F1F4F3F4E5ECE7E3F0FEE0E0E0E0E2EDF0E2F3F4F1F4E5ECF6E2F8FEE0E013
S1230260F1F4F1F4F3F4E5ECE7E3F0FEE0E0E0E0E1EDF0E2F3F4F1F4E5ECF6E2F8FEE0E0F5
S1230280F1F4F3F4F1F4E9ECE7E3F0FEE0E0E0E0E1EDF0E2F1F4F3F4E9ECF6E2F8FEE0E0CD
S12302A0F1F4F3F4F2F4E5ECE7E3F0FEE0E0E0E0E1EDF0E2F2F4F3F4E5ECF6E2F8FEE0E0B3
S12302C0F3F4F3F4F2F4E5ECE7E3F0FEE0E0E0E0E3EDF0E2F2F4F3F4E5ECF6E2F8FEE0E08F
S12302E0F1F4F0F4F3F4E9ECE7E3F0FEE0E0E0E0E1EDF0E2F3F4F0F4E9ECF6E2F8FEE0E06F
S1230300F3F4F3F4F3F4E5ECE7E3F0FEE0E0E0E0E3EDF0E2F3F4F3F4E5ECF6E2F8FEE0E04C
S1230320F1F4F3F4F3F4E5ECE7E3F0FEE0E0E0E0E1EDF0E2F3F4F3F4E5ECF6E2F8FEE0E030
S1230340F0F4F0F4F0F4E9ECE7E3F0FEE0E0E0E0E0EDF0E2F0F4F0F4E9ECF6E2F8FEE0E016
S1210360E8ECE8E3E9ECE8E3FCF3F4ECEBE4FDF3F4ECECE4F9F5FFFDE8ECF6E2E6FE84
S123037EE4ECF6E2EFECF0E3E6FEF0EBF9F5F0E7E5F1F1F0FFF3F9F5E8E6F0F1EFFEEAF074
S123039EF1E5F4F0FEF3F9F5E8E6F8F1F7FEEAF0F1E5F7F0F0ECECE4F9F5E8E6F0F1E0FF37
S10703BEEAF0F2E586
S12303FEE0E0F3F4F2F4E5ECFDE2F0FDE0E0E0E0F3F4F2F4E5ECFCE2F0E0E0E0E0E07E
S123041EE0E0F1F4F1F4F0F4E9ECFDE2F0FDE0E0E0E0F3F4F0F4E9ECFCE2F0E0E0E0E0E05D
S123043EE0E0F2F4F3F4F1F4E5ECFDE2F0FDE0E0E0E0F1F4F3F4E9ECFCE2F0E0E0E0E0E03C
S123045EE0E0F1F4F3F4F1F4E5ECFDE2F0FDE0E0E0E0F0F4F3F4E5ECFCE2F0E0E0E0E0E022
S123047EE0E0F1F4F1F4F3F4E9ECFDE2F0FDE0E0E0E0F3F4F1F4E5ECFCE2F0E0E0E0E0E0FD
S123049EE0E0F1F4F2F4F3F4E5ECFDE2F0FDE0E0E0E0F0F4F1F4E9ECFCE2F0E0E0E0E0E0DF
S12304BEE0E0F3F4F2F4F3F4E5ECFDE2F0FDE0E0E0E0F2F4F3F4E5ECFCE2F0E0E0E0E0E0BD
S12304DEE0E0F1F4F3F4F0F4E9ECFDE2F0FDE0E0E0E0F1F4F1F4E5ECFCE2F0E0E0E0E0E0A0
S12304FEE0E0F3F4F3F4F3F4E5ECFDE2F0FDE0E0E0E0F3F4F3F4E5ECFCE2F0E0E0E0E0E07B
S123051EE0E0F1F4F3F4F3F4E5ECFDE2F0FDE0E0E0E0F1F4F0F4E9ECFCE2F0E0E0E0E0E05D
S123053EE0E0F0F4F0F4F0F4E9ECFDE2F0FDE0E0E0E0F0F4F0F4E9ECFCE2F0E0E0E0E0E041
S121055EE0E0FAF0F0ECEBE4F9F5E8E6F8F1F8FDEAF0F2E5FCF3F0F5FCFEF1F5ECFE3D
S123057CE5ECE8E3FDF3F1F5E9FEEEF4F4ECECE4E1EDEBE4E8FFE8F4FFF5F4FEFDF3F1F554
S123059CF9FEE5ECE8E3F2F5E8FFEEF4F4ECECE4EBFDEBE4E8FFE4ECE8E3E8FFEBEDEBE491
S11B05BCE4ECE8E3FDF3F0F5E4FFE8FFE1EDEBE4E2EDECE4F0EAE6EEFF
S9030000FC
S00B0000504D41494E502020EF
S1230000F4EAE6FCF4EAFDFFF4EAE6FCF4EAE0E0F4EAE6FCF4EAE6FCF4EAE6FCF4EAE6FCE4
S1170600F0ECF9E3F4ECEDE4EEEDF9E3E5EBE5EBF6EAF8EC5E
S10B061EFFFFE0E0F6EAF8EC4E
S10B063EFFFFE0E0F6EAF8EC2E
S11D065EFFFFE9ECEFE3E8ECE2E3E4ECE3E3E4ECE4E3E5EBE4F0F6EAF8ECAB
S121067EFFFFE1E9F8E3E5FAF5EAE5FFE2E9F8E3EAFAF5EAF3FFE3E9F8E3F6EBEBFE063
S11D069CF6EAE1E0F0ECE0E4E8E6EFE6E8E2F7FAF6F1F4ECE0E4F5EAFDE654
S10B06BEFFFFE0E0F6EAF8ECAE
S12106DEFFFFE3E9EEE4F6EBF8ECF0ECF9E3F4ECEDE4EEEDF9E3E5EBE5EBF6EAF8EC15
S10B06FEFFFFE0E0F6EAF8EC6E
S11F071EFFFFF0ECFFE3E8E6EFE6F6FCF9FCE8E2F4ECFFE3E6EBF9EEF6EAF8EC6D
S10B073EFFFFE0E0F6EAF8EC2D
S119075EFFFFF0ECEAE4EFF4F0F5F6EBE3E1F4ECEAE4F6EAE3E11A
S109077EFFFFF5EAE1E1D2
S10B079EFFFFE0E0F6EAF8ECCD
S11907BEFFFFE4EBFDF6E4ECE3E3E4ECE4E3E5EBF9ECF6EAF8ECBB
S10B07DEFFFFE0E0F6EAF8EC8D
S11907FEFFFFF0ECF9E3F4ECEDE4EDEDF9E3E5EBE1EEF6EAF8EC61
S10B081EFFFFE0E0F6EAF8EC4C
S10B083EFFFFE0E0F6EAF8EC2C
S11D085EFFFFE9ECEFE3E8ECE2E3E4ECE4E3E5EBECF0F6EAF8ECA1
S121087EFFFFE1E9F8E3E5FAF5EAF5FDE2E9F8E3EAFAF5EAE1FEE3E9F8E3F5EBF9FE3F
S11B089CF5EAEDFEF0ECE0E4E1F4F6F5F6FAF0F1F4ECE0E4F5EAFDE6DF
S10B08BEFFFFE0E0F6EAF8ECAC
S12108DEFFFFE3E9EEE4F6EBF8ECF0ECF9E3F4ECEDE4EDEDF9E3E5EBE1EEF6EAF8EC15
S10B08FEFFFFE0E0F6EAF8EC6C
S11D091EFFFFF0ECFFE3E1F4F9F5F6FCF8FCF4ECFFE3E6EBF9EEF6EAF8EC18
```

MediMonitor program for Hitachi 4bit Microcontroller HD4074808 in Hex Format
Copyright ©1989, 1990 Current Designs Corporation, New York, NY
Medi-Monitor Corporation, New York, NY                                    page 2

```
S10B093EFFFFE0E0F6EAF8EC2B
S11B095EFFFFF0ECEAE4E1F4F9F5F7FDF6EAE3E1F4ECEAE4F6EAE3E128
S109097EFFFFF5EAE0E3CF
S11F099EFFFFE4EBFDF6E4ECE2E3E4ECE4E3E5EBFFFBFCE2E5EBF8EEF6EAF8EC2B
S10B09BEFFFFE0E0F6EAF8ECAB
S10B09DEFFFFE0E0F6EAF8EC8B
S12109FEFFFFE1EDF9E3E8ECF0E3E4EBFDF6E5ECE1E3E4ECE4E3E4ECE0E3F5EAFFE445
S1170A1EFFFFE2EDF9E3E4EBFDF6F1F1F4ECF8E3F5EAF9E7F9
S1210A3EFFFFE4EBFDF6F0ECF8E3E1F4F4ECF8E3F4F5F5EBF9E7EFEDF9E3F6EAFDE071
S10F0A5EFFFFE2EDF9E3E0F9F6EAF8EC42
S10B0A7EFFFFE0E0F6EAF8ECEA
S10B0A9EFFFFE0E0F6EAF8ECCA
S10B0ABEFFFFE0E0F6EAF8ECAA
S10B0ADEFFFFE0E0F6EAF8EC8A
S10B0AFEFFFFE0E0F6EAF8EC6A
S10B0B1EFFFFE0E0F6EAF8EC49
S10B0B3EFFFFE0E0F6EAF8EC29
S10D0B5EFFFFE4EBF1E2F6EAF8EC25
S1230B7EFFFFECECFAE3E4FEEDFEEFECF0E3EBECF0E3EBFEE7ECF0E3E0EBF0EDF6EAF8EC80
S10B0B9EFFFFE0E0F6EAF8ECC9
S10B0BBEFFFFE0E0F6EAF8ECA9
S10D0BDEFFFFE6EBF9EBF6EAF8EC92
S1210BFEFFFFECEDF9E3E8ECF0E3E4ECFBE3E1EDFAE3E5ECE0E3E4ECE4E3F6EAF8EC33
S11D0C1EFFFFECEDF9E3E4ECFBE3E2EDFAE3E5ECE0E3E8ECE0E3F6EAF8ECBC
S11D0C3EFFFFE4EDF9E3E5ECE0E3E8ECE0E3E4ECE6E3E1EDE5E4F6EAF8ECCE
S11D0C5EFFFFE8ECE2E3E8ECE3E3E8ECE4E3E4EBFBE6E0F9E0F9F6EAF8EC86
S10B0C7EFFFFE0E0F6EAF8ECE8
S10B0C9EFFFFE0E0F6EAF8ECC8
S10B0CBEFFFFE0E0F6EAF8ECA8
S10B0CDEFFFFE0E0F6EAF8EC88
S10B0CFEFFFFE0E0F6EAF8EC68
S10B0D1EFFFFE0E0F6EAF8EC47
S10B0D3EFFFFE0E0F6EAF8EC27
S10B0D5EFFFFE0E0F6EAF8EC07
S10B0D7EFFFFE0E0F6EAF8ECE7
S10B0D9EFFFFE0E0F6EAF8ECC7
S10B0DBEFFFFE0E0F6EAF8ECA7
S1210DDEFFFFEBEDF9E3E4EBFDF6E4ECFBE3E5ECE0E3E4ECE1E3E4ECFEE2F6EAF8EC35
S10F0DFEFFFFE5F3F1F1F7F7F6EAF8EC7B
S10D0E1EFFFFE6EBF9EBF6EAF8EC4F
S10D0E3EFFFFE6EBF9EBF6EAF8EC2F
S10D0E5EFFFFE6EBF9EBF6EAF8EC0F
S1150E7EFFFFE5EDF9E3E8ECE6E3E8ECE5E4F5EAFDE6B6
S1230E9EFFFFE6E9E0E4FBFAE8ECE8E4E9ECEFE3E4ECE4E3F6EAE5E9E2EDF9E3F6EAF1E1C1
S1190EBEFFFFE8ECFCE2E0EDF5E4E4ECFBE3ECEDF9E3F6EAF8EC9D
S11D0EDEFFFFE3E9EEE4F4EBE6EFE7EDEEE4E4ECFDE2E4ECFCE2F6EAF8ECDF
S10B0EFEFFFFE0E0F6EAF8EC66
S10D0F1EFFFFE6EBF9EBF6EAF8EC4E
S1130F3EFFFFE4EBFDF0FFF5E6EBF9EBF6EAF8EC78
S10D0F5EFFFFE6EBF9EBF6EAF8EC0E
S11D0F7EFFFFEDECFAE3F5EBEEE5EEECFAE3F6EBFAE9E6EBF9EBF6EAF8ECFA
S11D0F9EFFFFF0ECEDE4F4ECF9E3E4EBFDF6E4ECF0E3E4EBE3EBF6EAF8EC08
S11D0FBEFFFFF0ECEDE4F4ECF9E3E4EBFDF6E4ECF0E3E4EBE3EBF6EAF8ECE8
S10D0FDEFFFFE6EBF9EBF6EAF8EC8E
S10D0FFEFFFFF1F1F7F7F6EAF8EC53
S10D101EFFFFE6EBF9EBF6EAF8EC4D
S10D103EFFFFE6EBF9EBF6EAF8EC2D
S10D105EFFFFE6EBF9EBF6EAF8EC0D
S10D107EFFFFE6EBF9EBF6EAF8ECED
S10D109EFFFFE6EBF9EBF6EAF8ECCD
```

MediMonitor program for Hitachi 4bit Microcontroller HD4074808 in Hex Format
Copyright ©1989, 1990 Current Designs Corporation, New York, NY
Medi-Monitor Corporation, New York, NY                                    page 3

```
S10910BEFFFFF6EAEFEB70
S11F10DEFFFFE7E9EEE4F9FBE3EDEEE4E8ECFDE2E8ECFCE2E0EDFEE3F6EAF8ECE5
S10B10FEFFFFE0E0F6EAF8EC64
S11D111EFFFFF0ECFFE3E1F4F9F5F6FCF8FCF4ECFFE3E6EBF9EEF6EAF8EC10
S10D113EFFFFE6EBF9EBF6EAF8EC2C
S10B115EFFFFE0E0F6EAF8EC03
S10B117EFFFFE0E0F6EAF8ECE3
S11D119EFFFFF0ECEDE4F4ECF9E3E4EBFDF6E4ECF0E3E4EBE3EBF6EAF8EC06
S11D11BEFFFFF0ECEDE4F4ECF9E3E4EBFDF6E4ECF0E3E4EBE3EBF6EAF8ECE6
S10D11DEFFFFE6EBF9EBF6EAF8EC8C
S1212000F7F3E1F4F7F7EAECE1E0F2F2E4E8F7E4E4EBF5EFECECE7E2F1F8E0E9F1E315
S123201EE4EBECEDECECF0E3E8FAE4EBF8E3F1F3E1F4FFF8F1F7EEECF0E3E4EBEDEBF1E002
S123203EF1F1F1F7FCE9FCE3EDF9F0ECFCE3E1F4F4ECFCE3FBF5EDF9E6EBF9EBF0F3E1F478
S123205EF2F9F0F7F1E0F8F1F0F7E4EBF1E8E0E9E5E2FAF9FDF9E5E9E5E2E3FAE6ECF0E3B3
S121207EE0E9FFE3E4EBFDE7ECECF0E3E4EBE3EBF1E0ECECF6E2EEFAE4ECF6E2F6F89B
S123209CE8ECF6E2F6F8F4F0E2E0FCF0F0ECEAE4E0E3E9F4F4E6F6F7E2E0EFF0E0E0E4E3BB
S12320BCE7F7E0E0E0E0F6F3EFF4E2FBE0E7FDFAE4E7E7F3EFE6E1FBE2E0FFE6FAFAE7F76C
S12320DCF0E0F6F0EFF0EFF4F1FBEFE6F1FBFFE6F0FBF0E0E0E9FBE3E4EBF6E6E0E9E5E437
S12320FCE4EBFFF5E0E9E6E4E4EBE2E5E0E9E7E4E4EBF5E4E0E9E8E4E4EBEFE5E0E9E9E4CA
S121211CE4EBFCE5E0E9F5E4E4EBE9E6F0E0EDECE7E4FDFCE5ECE7E4E8ECEBE3F0E036
S121213AE9ECE7E4E4ECEBE3F0E0EDECE6E4EAFDE5ECE6E4E9ECEEE3F0E0E9ECE6E43B
S1232158E5ECEEE3F0E0EDECE8E4F7FDE5ECE8E4E8ECEFE3F0E0E9ECE8E4E4ECEFE3F0E032
S1232178EDECE9E4E4FEE5ECE9E4E9ECEFE3F0E0E9ECE9E4E5ECEFE3F0E0EDECF5E4F1FEF0
S1232198E5ECF5E4E8ECFCE2F0E0E9ECF5E4E4ECFCE2F0E0EDECFBE3F9FFE5ECFBE3F0E796
S12321B8EEF1F0F0FBF1FCF7F0E2FBF1FDF7F0E2FBF1FEF7F0E2FBF1FFF7F0E2E0EBF0EDD2
S12121D8F0ECE0E7FCF7F0ECE1E7FDF7F0ECE2E7FEF7F0ECE3E7FFF7F0E0E9ECFBE3FE
S12321F6F0EAF0EDF0ECEFE4E1F4E4F8F4ECEFE4F0E0E4EDEFE4F0ECFFE3EFF4F4ECFFE324
S1232216F0F5EEF8F0E0E8ECEEE3F0E0F5F3E1F4F9F5F5F7FDF9E0EDE5E2F4F3E1F4F5F5CD
S1212236F4F7FDF9E0EDE4E2F3F3E1F4F3F7E4E9E3E2F5F9F2F3F1F5FDF9E0EDE2E29B
S1232254E0EDE3E2EDECF0E3F2F9E5ECF0E3F0E0E9ECF0E3F0E0F3F3F9F5FDF9E0EDE3E2F5
S1232274F2F3E1F4F2F7F0E0FFF3E5F4F9F5FFF7E2FBE0EDEFE2FEF3E1F4F5F5FEF7E2FB27
S1232294E0EDEEE2FDF3E1F4FDF7E4E9EDE2FAFAFCF3F1F5E2FBE0EDECE2E0EDEDE2F0E087
S12322B4FDF3F9F5E2FBE0EDEDE2FCF3E1F4FCF7F0E0F2F3FCF7F3F3FDF7F4F3FEF7F5F3B2
S12322D4FFF7F0EAF0EDEAECF0E3F0ECFDCE3E1F4F1F5FEFBF4ECFDE3FCF5FEFBE0EDFDE3C9
S12122F4E5ECFEE2E5ECEEE4E1EDFFE1E5F3E9EDF2E0E4EBECFAE8ECFDE4ECF5EDFC12
S1212312E4ECFDE4E4ECE7E3E8EDF2E0E5F7F0F1F4E4E0EDFFE1E0E1F7FCF0E0F0E41D
S1212330EDECF0E3FFFCFCECF6E4FFFCF0E0ECE8F1E3F4ECF1E3E1EDFDE3E1EDFEE39E
S123234EE0EDF2E3E0EDF3E3F0E0EAE9F9E3F0FDF0E0E7E9F9E3F4FDE7FEEDE9F9E3F8FDC1
S123236EFBFDEEE9F9E3FFFDE3E9EEE4FFFDE7FEE6EBF9EBE7EDF9E3E4ECEEE4EAECEEE476
S121238EEDECEEE4FFFEE0E9FEE3E6EBFEF0ECECF1E3E4EBE7F2EDECF1E3E4EBE5F374
S12323ACEEECF1E3E4EBE3F4EFECF1E3E4EBE1F5F0E0ECECF0E3E3FFEAFEE5ECFEE2EAFE87
S12123CCE7E9EEE4F6EBF8ECE0EDF1E3E0EDFDE3E0EDEEE4FFF5E6EBF9EBF6EAF8EC2E
S12323EAF4ECF7E4FEF5FAFFF0E0E8E6F8E6E0EAE8E2F4ECF8E4E7E9F9E3EAF9FCECF1E311
S123240AF4ECF9E4EFE5FCECF1E3F4ECF1E3F7F8E0EDF9E3E9ECFEE2E3EDFCE3E0EDFDE304
S123242AE0EDEEE4E0E9F9E4E1F9E4EBF1E2F0E0F0ECF8E4F4ECF9E4EBECFAE1EDFFE125
S121244AF0ECF9E4ECE0F4E4F0E0EAEDF9E3E8ECF0E3E4EBFDF6E5ECEBE3ECECF8E4D4
S1232468E4EBEDF2EDECF8E4E4EBEBF3EEECF8E4E4EBE9F4EFECF8E4E4EBE7F5E3EDFCE3CD
S1212488E4EBF1E2F0E0F2F0E4EBF3F6FBE9F9E3FBFAE9ECE2E3E9ECE3E3E9ECE4E3A0
S12124A6EDECE5E4FBFAE1E9F4E3FCFAE5ECE2E3F0E0E2E9F4E3E2FBE5ECE2E3F0E09A
S12124C4E5ECE4E3F0E0F1F0E4EBF3F6FBE9F9E3FBFAE9ECE6E3E9ECE5E3E8ECE5E369
S12124E2EDECE5E4F9FBE1E9F5E3FAFBE5ECE6E3F0E0E2E9F5E3E0FCE5ECE5E3F0E059
S1212500E4ECE5E3F0E0F0F0E4EBF3F6FBE9F9E3FBFAE9ECE9E3E8ECE9E3E9ECEAE321
S121251EEDECE5E4F7FCE1E9F6E3F8FCE5ECE9E3F0E0F6E3FEFCE4ECE9E3F0E0F8
S121253CE5ECEAE3F0E0F3F0E4EBF3F6FBE9F9E3FBFAE9ECECE3E9ECEDE3E8ECEDE3D2
S121255AEDECE5E4F5FDE1E9F7E3F6FDE5ECECE3F0E0E2E9F7E3FCFDE5ECEDE3F0E0B5
S1212578E4ECEDE3F0E0EDECE5E4E5FEE5ECE5E4E7FEE9ECE5E4E1E9F8E3EBFEEDFABA
S1232596E2E9F8E3EFFEEBFBE3E9F8E3E7FDE9FCF0F1EFF0E4E3EFE6F6FEE1F4FBFEF6FE26
S12325B6E4E7F0E0F0E7E1F0F5F1E8E7F0F0E4EBF1FFECECFDE4EEFFE0E9FFE3EBFFF0E05F
S12325D6E4ECEEE3F0E0E4ECE7E3E7FFF5F3E8E6EFE6E8E2F5F7F4EBFCF8E9EDE5E2F4F358
S12325F6E8E6EFE6E8E2F4F7FCF8E5EDE4E2F3F3E8E26EFE6E8E2F3F7FCF8E9EDE3E2F2F32C
```

MediMonitor program for Hitachi 4bit Microcontroller HD4074808 in Hex Format
Copyright ©1989, 1990 Current Designs Corporation, New York, NY
Medi-Monitor Corporation, New York, NY

```
S1212616E8E6EFE6E8E2F2F7FCF8E2EDE2E2E3EDE3E2EDECF0E3FAF8E5ECF0E3F0E01E
S1232634E9ECF0E3F0E0FFF3EEF4F0F1FFF7FEF9F5F1FFF7FEF3E8E6EFE6E8E2FEF7FEF942
S1232654E5EDEEE2FDF3E8E6EFE6E8E2FDF7FEF9E9EDEDE2FCF3E8E6EFE6E8E2FCF7FEF98D
S1212674E2EDECE2E3EDEDE2F0E0E1F0FFE6E3FAE7FAEAF4E6FAE0FAECE2E8E7E8E2C5
S1232692F0E8E0E0F0E0F2F3F8E6F3F3E1F0FFE6F3FAF7FAEAF4F6FAF0FAECE2E8E7E8E260
S12326B2F0E8E0E0F4F3EFE7F5E9E5E2E1FBECE7E1E5F8E6F0E0E0E8E0E0F1F5E1E0E8E3ED
S12326D2E1E0FFFBE6F4F9F5E1EDECE2F3FBE2EDECE2E6F4FDF7EFE5ECE7E0E5FEF7EFE339
S12126F2E5EDEFE2FEFBE0EDEFE2F0E0E0EDECE2F9F5F3FBE1EDECE2F2FBE5ECE1E02A
S1232710E5ECE2E0E7ECE2E0E5ECE3E0E4EDE4E0EAEDE8E0E5EDECE0E8EDF2E0E7EDF3E0C9
S1232730E2EDF4E0EFEDFBE1EFEDFCE1F0E7E8F0F7F1E8E7F1F0FFE6E4EBF1FFEBEDF0E3DB
S1232750EFEDE0E2EEEDE1E2E0EDE2E2E5EDE3E2E5EDE4E2E4EDE5E2E0EDE8E2E8EDE9E29A
S1232770E0EDEAE2E0EDEBE2E5EDEAE4E1EDF4E3E1EDF5E3E1EDF6E3E1EDF7E3E0EDFFE12B
S1232790F1E7EFF0F0F1E8E7F0F0FFF5E4EBF1FFF2E7E9F0F0F1E8E7F0F0FFF5E4EBF1FF36
S12327B0EEE9FCE3F8FFE6EBF9EBFFF5E6EBEAEFE3EDF0E3EAECE1E0EBECE1E0EAECE0E09D
S12327D0EBECE0E0E4ECE0E0E0EDEAE0E0F4EAEDFFF0F4F1FFE1F4E8E7EFE6F1FFF0E090
S12327F0EEEDFCE3E1EDFFE1E8FEE7ECE0E0F0F2FEF5EFF8F1F2F8E6F0ECF9E3E8E6F0F100
S1232810FEE3EBF8F4E5FDE3F6EBF8ECF3E5F8E6F0ECF9E3E8E6F0F1FEE3F7F8F6E5FDE3BA
S1212830FAF8F5E5FBE3FDF8F8E5F7E3F6EBF8ECF7E5F2F1F7F7ECECFAE3E4EBF1F752
S123284EEDECFAE3E4EBFDF8EEECFAE3E4EBFDF8ECECFAE3E4EBE3EBEDECFAE3E0EBF0EDC1
S123286EEEECFAE3E0EBF0EDE0EDFBE3E4ECE0E0E0E0E0E8ECE0E0E3EDFCE3E1EDFBE33D
S123288EF1F2F8E6FDE3F6EBF4EEF7F3F8E6F4E3F2FAF5F1FBFAF7E3F6FAF8F1FBFAF9F5C6
S12128AEFBF9FFE3FBFAFBF1F7F7E4EBEFE3F5EAE3E1F2F1F7F7ECECFAE3E4EBF1E8F1
S12328CCEDECFAE3E4EBFEE9EEECFAE3E4EBFEE9ECECFAE3E4EBE3EBEDECFAE3E0EBF0ED5F
S12328BCEEECFAE3E0EBF0EDE0EDFBE3E4ECE0E0E0E0E0E8ECE0E0E3EDFCE3E1EDFBE3BF
S123290CF1F2F8E6FEE3F6EBF4EEF7F3F8E6F4E3F1FCF5F1FAFCF7E3F5FCF8F1FAFCF9F542
S123292CFAFBFFE3FAFCFBF1F7F7E4EBEFE3F5EAE2E3F8F3FCF7F9F3FDF7FAF3FEF7BF30D
S123294CFFF7E8ECFBE3FFF5E0EBF0EDF6EAF8ECFCF3F8F7DF3F9F7FEF3FAF7FFF3FBF7DB
S123296CE1EDF8E3F0ECE1E4F4ECE0E4F5F5E6EBFAE1E2EDF8E3F0ECE2E4F4ECE0E4F5F5E9
S121298CE6EBFAE1E3EDF8E3F0ECE3E4F4ECE0E4F5F5E6EBFAE1E4EDF8E3F0ECE4E4A5
S12329AAF4ECE0E4F5F5E6EBFAE1FFF5F1EAE0E8E4EBFBE6E9ECEEE3E8ECEBE3E8ECE2E3A7
S12329CAE8ECE4E3E8ECEFE3E8ECFCF2E0EDFBE3E0EDE6E4E0EDE7E4E0EDE8E4E0EDF5E4DD
S12129EAF0ECE0E4F5EAF9E8F8E6E4ECE0E3E4ECFFE2E5ECEFE3F1E3E7F8E4EBEDF245
S1232A08F0ECE1E4F9F8F2E3EEF8E4EBEBF3F0ECE2E4F9F8F3E5F8E4EBE9F4F0ECE3E40B
S1232A28F9F8E4EBE7F5F0ECE4E4F8E6F4ECE0E4F0E3F9E5ECEEE3E5E9F9E3F6EBF8EC03
S1232A48E1EDE6E4F6EAF8ECF5E3F4F9E4ECEBE3F1F1E5E9F9E3F4FAE1EDE7E4F5EAF4EADB
S1212A68F6E3F4FAE4ECEFE3E5E9F9E3FFF9E1EDE8E4F6EAF8ECE3EDF9E3E4EBECFA82
S1232A86E5EBF2FBF0E7E9F1F0ECF8E3F6E6F0E4F4ECF0E4F9F5F4FAE6F4FFF7E1EDEEE257
S1232AA6F7FAFFF7EBEDEEE2EBEDEDE2EBEDECE2E0EBF0EDE5E9F9E3F6EBF8ECE1EDFBE36D
S1232AC6F6EAF8ECE8ECF0E3E4EBFDF6E4ECE3E4ECE4E3E0EDF8E3E0EDFAE4E0EDFBE493
S1232AE6E4EBECFAE5EBF8F5EAE9EEE2F9FFE5EBF2FBE5EBEAFCE0E9FAE4EFFDE5ECFEE208
S1232B06ECECFCE4E4EBEDF2EDECFCE4E4EBEBF3EEECFCE4E4EBE9F4EFECFCE4EBE7F513
S1212B26E4EBE4FBFFF5E0EBF0EDF0E0E5EBFFFBE0E9FAE4E0FDFFE6FFF5E5EBF8F58F
S1232B44EAE9EEE2F9FFE5EBF2FBE5EBE2FDF1F5F9FFE0F9FAE4EFFDE1FCECE4E4EBEDF29A
S1212B64EDE4E4EBEBF3EEE4E4EBE9F4EFE4E4EBE7F5E4EBE4FBFFF5E0EBF0EDF0E0BB
S1212B82E4EBFDF6E4ECE2E3E4ECE4E3E8ECF0E3E0EDF8E3E4EBECFAFCE2E5EBFDF0A4
S1212BA0EAE9EEE2F9FFE5EBF2FBE5EBEAFCE3FFE5EBFDF0EAE9EEE2F9FFE5EBF2FB0E
S1232BBEE5EBE2FDF1F5F9FFECECE6E2E4EBEDF2EDECE6E2E4EBEBF3EEECE6E2E4EBE9F47C
S1232BDEEFECE6E2E4EBE7F5E4EBE4FBFFF5E0EBF0EDF0E0F0ECEDE4F4ECF9E3E4EBFDF640
S1232BFEE4ECF0E3E4EBE3EBF0E0E5EBFFFBFFE6FFF5E5EBF5F5F5EAF1F0E5EBFFFBFCE2DE
S1232C1EE5EBFDF0EAE9EEE2FCF8E5EBF2FBFFF5E4EBE4FBFFF5E0EBF0EDF0E0E0EDFFE1C6
S1232C3EE2EDEDE2E3EDEEE2E0EDEFE2E0E9E0E0F1F5EAF9F7FAF1E7E1E0E8E3E1E0E8E661
S1232C5EE0EAFFF5E5EBEAF3FEF3E1F4FEF7F5F5E9FAF0E0F1E7E2EDEFE2EFF0F0F1E8E788
S1232C7EF1F0FFE6E5EBEAF3FEF3E1F4FEF7F5F5E9FAF0E0F2E7E8F0F0F1E8E7F1F0FFE640
S1232C9EE5EBEAF3FEF3E1F4FEF7F5F5F9F9F0E0F2E7E1E0E8E3E1E0E8F4E8E6E0EAE8F488
S1212CBEE5EBEAF3FEF3E1F4FEF7F5F5F9F9F0E0E9EDEEE2F0E0E0E9F8E3EEFBFEFCE3
S1232CDCE1E9F8E3F2FBFAFBE2E9F8E3F6FBE3FCE3E9F8E3F5FCECFCECE4E7FBFCE2FAFBD2
S1232CFCE1F4E8E7EFE6FAFBF0E0EDE4E7FBFCE2E3FCE1F4E8E7EFE6E3FCF0E0EEE4E7FB2A
S1232D1CFCE2ECFCE1F4E8E7EFE6ECFCF0E0EFE4E7FBFCE2F5FCE1F4E8E7EFE6F5FCF0E0DE
S1232D3CE0E1E7FDFCE2FEFCE1F4E8E7EFE6FEFCF0E0F6F7FFF3FCE8F0E3FCECEDE2F0E492
S1232D5CF1FDFCECF6E4F6F7E7FBF5EAE0F5E0EDFFE1FAFDE1EDFFE1E3EDEEE2E2EDEDE290
```

MediMonitor program for Hitachi 4bit Microcontroller HD4074808 in Hex Format
Copyright ©1989, 1990 Current Designs Corporation, New York, NY
Medi-Monitor Corporation, New York, NY                    page 5

```
S1232D7CE0EDEFE2E1E0E8E3FFE3EDFEEFF4EDFEE4EDEEE2E0E8E0E0F1F5F2FFE6FFE8E7BA
S1232D9CE8E6E0E8E0E0F1F5F4FEFDFEF1E7E5EBE3F8FEF3E1F4FEF7F5F5E6FFF0E0F2E728
S1232DBCE5EBE3F8FEF3E1F4FEF7F5F5E6FFF0E0F1E7EFF0EFF1FCF0E5EBE3F8FEF3E1F4FA
S1232DDCFEF7F5F5F2FFF0E0F2E7E2EDEFE2E7F0E7F1FCF0E5EBE3F8FEF3E1F4FEF7F5F5CF
S1232DFCE6FFF0E0E9EDEEE2F0E0E0E9F8E3E7F8F7F9E1E9F8E3EBF8F3F8E2E9F8E3EFF815
S1232E1CFCF8E3E9F8E3EEF9E5F9ECE4E0F8FFE6F3F8EFE6E8E2E8E7F3F8F0E0EDE4E0F8E8
S1232E3CFFE6FCF8EFE6E8E2E8E7FCF8F0E0EEE4E0F8FFE6E5F9EFE6E8E2E8E7E5F9F0E0DE
S1232E5CEFE4E0F8FFE6EEF9EFE6E8E2E8E7E6FAF9EFE6E8E2E8E7FAF9E1EDFFE1E0E1E9FAC6
S1232E7CE0EDFFE1E0E1F2FAFFE6FAF9EFE6E8E2E8E7FAF9F0E0F0ECFBE4ECE0F4ECFBE489
S1232E9CE5EDFAE4F5EAE0F8F0ECFBE4FCE4FCE0F4ECFCE4FFF3FCE8F0E3FCECEDE2E4FB35
S1232EBCF0ECFCE4FCECF6E4F4ECFCE4F0ECFBE4FCE0FCECFBE4F4ECFBE4E0EDFAE4F0F10B
S1232EDCECE8FCE4E0F8E2FAE0E8E0E0F4ECE5E7E1E0E8E3E1E0F4ECE6E7EFE5F4ECE7E7BA
S1232EFCF0E0F0ECE5E7F0E8E0E0F0ECE6E7E8E7F0ECE7E7F8E6F0E0E0E8E0E0F4ECE8E79B
S1232F1CE1E0E8E3E1E0F4ECE9E7EFE5F4ECEAE7F0E0F0ECE8E7F0E8E0E0F0ECE9E7E8E781
S1232F3CF0ECEAE7F8E6F0E0F0ECE5E7E4E8E8E7F3FDF0ECE6E7E4E8E9E7F3FDF0ECE7E704
S1212F5CE4E8EAE7F3FDF0F1F0E0FFF1F0E0F1F1E8E8F4E3F3F5FBFDF1F1F4ECF4E353
S1232F7AE4EBEDF2F6EAF8ECF1F1E8E8F5E3F3F5E7FEF1F1F4ECF5E3E4EBEBF3F6EAF8EC5F
S1232F9AF1F1E8E8F6E3F3F5F3FEF1F1F4ECF6E3E4EBE9F4F6EAF8ECF1F1E8E8F7E3F3F530
S1212FBAFFFEF1F1F4ECF7E3E4EBE7F5F6EAF8ECF2F1EFE7F8ECF4E3EBFFF2F1E1F4D7
S1232FD8F4ECF4E3FFF5E4EBEDF2F6EAF8ECF2F1EFE7F8ECF5E3F9FFF2F1E1F4F4ECF5E3DB
S1212FF8FFF5E4EBEBF3F6EAF8ECF2F1EFE7F8ECF6E3E7F8F2F1E1F4F4ECF6E3FFF598
S1233016E4EBE9F4F6EAF8ECF2F1EFE7F8ECF7E3F5F8F2F1E1F4F4ECF7E3FFF5E4EBE7F5B1
S1213036F6EAF8ECE4ECFEE2E4ECE1E3E4ECE0E3F0ECEAE4FEF7EBEDEFE2EBEDEDE2EE
S1233054EBEDECE2FFF5E0EBF0EDF6EAF8ECE9ECE0E3E4ECE0E3FFF5E6EBFAE1F5EAFDE6C5
S1233074F0E7E8F1F0ECF8E3F8E6F0ECE0E4F4E4E6EBF4E6E0E9E0E4E8FAF0E0F8F3F8E6C8
S1233094F9F3E4EBFFF9FAF3EFE7E0E9EBE2F3FAECE7E1E5F8E6E6EBE3E6E1E9E0E4FBFA8B
S12330B4F0E0E5E9E0E4F3FBF0ECF8E3F8E6F1E3E6FBE8ECF6E4F0E0F2E3EBFBE9ECF6E476
S12330D4F0E0F3E3F0FBEAECF6E4F0E0EBECF6E4F0E0E2E9E0E4F1FCE0E8E0E0F1F5E1E09B
S12330F4FCFBFFFBE8E3FBF5E7FCF1E7E8E3E4F4E8E7FFF5E6EBE3E6F0E0ECF4E8E7EDFCE9
S1213114E6EBE3E6F0E0F2E7E6EBE3E6F0E0E3E9E0E4F9FCE6EBE0E5E6EBE0E5F0E06B
S1233132E6EBF5E5E6EBF5E5E6EBF5E5F0E0E1E0E0E8E0E0F1F5EEFDE8E3F1F5EEFDEEF410
S1233152E8E7F1E7E6EBE3E6F0E0E8E3E6F4E8E7EDFCE6EBE3E6F0E0E1E0E0E8E0E0F1F552
S1213172FFFDE8E3F3F5FFFDECF4E9FDE8E3E4F4F6EAF0E5E1E9F8E3E8FEE4E4F0E04F
S1233190E2E9F8E3EDFEE5E4F0E0E3E9F8E3F2FEE6E4F0E0E7E4F0E0E0EDFFE1F1E7EFF0C1
S12131B0F0F1E8E7F1F0FFE6E6EBE7E7F2E7E8F0F0F1E8E7F1F0FFE6E6EBE7E7F0E052
S12331CEE1E9F8E3EFFFE6EBE5E8E4ECF6E4F0E0E2E9F8E3F7FFE6EBEDE8E5ECF6E4F0E075
S12331EEE3E9F8E3F6EBE0E8E6EBF5E8E6ECF6E4F0E0E6EBFDE8E7ECF6E4F0E0E8E4FCE266
S123320EE5F8E1F4E8E7EFE6E5F8F0E0E9E4FCE2EDF8E1F4E8E7EFE6EDF8F0E0EAE4FCE22F
S123322EF5F8E1F4E8E7EFE6F5F8F0E0EBE4FCE2FDF8E1F4E8E7EFE6FDF8F0E0E4ECFBE3CB
S121324EECEDF9E3E4EDFAE3F8F3FCF7F9F3FDF7FAF3FEF7FBF3FFF7FFF5E0EBF0EDDB
S123326CE0EDF0E4F6EAF8ECF0E7E9F1F0F0F0E4E1F4EFFBF4E4F0ECF8E3F8E6F0ECF0E498
S123328CF4E4F1F5EAFAF4FAF0E7E8F1F0ECF8E3F8E6F0ECE0E4F4E4E6EBF4E6FCF3F8E659
S12132ACFDF3E4EBFFF9FEF3EFE7E0E9EFE2FFFAECE7E1E5F8E6E6EBE3E6E6EDF9E32F
S12332CAE4ECE2E3E4ECFCE2E1EDF5E4E8ECFBE3F6EAF8ECE2EDF9E3E9ECE0E3E4ECE0E3AA
S12332EAE5ECEFE3F5EAFDE6FFF5E4EBFDF6FFF5E4EBE3EBE4ECF0E3E0EDF9E3E0EDFAE31E
S123330AF6F1F7F7E0EDFBE3E0EDE5E4E0EDE6E4E0EDE7E4E0EDE8E4E0EDE9E4E0EDF8E37F
S123332AF0E0E4EBF1E2E4ECE0E0E0E0E0E8ECE0E0E3EDFCE3E0E9F9E3EEFEF7F3F8E661
S121334AF4E3EEFEE1F4F7F0F2F8E6F7E3F2FDE0EDFFE3E8ECEEE3EEFEFBE3EEFE48
S1233368F0ECFFE3E1F4F9F5FAFDFEFDF4ECFFE3E3EDEFE4E9EDF9E3E8ECF0E3E5ECE0E37C
S1233388E4ECE1E3E5ECFFE2E4ECE4E3E4ECEAE3E6EBF9EEF0F2FEF5F8FCF1F2FEF5F8FC5C
S12333A8EBECE0E0EAECE0E0F1E0FBF1FCF7FBF1FDF7FBF1FEF7E8ECEEE3F0ECFFE3F0F51B
S12333C8E7FFE4ECEEE3FFF7F0EAF0EDE4EBFDF6E3EDFBE2E5ECFCE2E5ECFDE2E4ECF9E234
S12333E8E4ECF8E2E3EDF7E2E5ECF0E2E5ECF5E2F0F2FEF5F6EBE1F0F0E0F0ECE0E7E1F454
S1233408F4ECE0E7EAF8E4EBEFE3E1F8FBF1FCF7F2F1FDF7F0F1FEF7F7F1FFF7E0EBF0ED8B
S1233428F0ECE0E7E1F4F4ECE0E7F6EBEAEFE4EBEFE3F4F8F0ECFEE3E1F4F4ECFEE3F1F9DD
S1233448E4E9F2E3F0F9E0E9FFE3F0F9E4EBF1E2E4EBEFE3E4EBF1E2F0E0E1F4F4ECFEE3F6
S11D3468F0ECF2E3E1F4F4ECF2E3F0ECF3E3E9F4F0F9F4ECF3E3F6EAE7F125
S9030000FC
```

APPENDIX B

Source code for the microcontroller

Title:

ELECTRONIC MEDICATION MONITORING AND DISPENSING METHOD

Inventors:

Bruce A. KEHR
Richard D. DEMENUS
David LERNER
Michael J. EDL

© Media-Monitor Corp.

MediMonitor assembly language program for Hitachi 4bit Microcontroller HD4074808, page 1
©1989, 1990 Current Designs Corporation, New York, NY, Medi-Monitor Corporation

```
            Title   'Medi-Monitor - Main, February 26, 1990'

*           Annunciators
iAM         Equ 0,$68
iPM         Equ 1,$68
iNOBELL     Equ 0,$6E          Crossed out bell
iCOLON      Equ 0,$56
iSET        Equ 1,$60
iSPCIAL     Equ 0,$6F          SPECIAL
iFIRST      Equ 1,$61          FIRST DOSE
iSCHED      Equ 0,$5F          SCHEDULE
iNEXT       Equ 0,$62
iLAST       Equ 0,$63
iTIME       Equ 0,$64
iBEEP       Equ 0,$61
iOFF        Equ 1,$5F
iMISSED     Equ 1,$5E
iVOLUME     Equ 0,$5E
iHOWMNY     Equ 0,$66          HOW MANY PILLS?
iTIPRDY     Equ 1,$6F          TIMES PER DAY
iEVYODY     Equ 0,$6B          EVERY OTHER DAY
iHOURS      Equ 0,$6A
iASNEED     Equ 1,$6E          AS NEEDED
iUNSKPL     Equ 1,$6B          UNSCHEDULED PILL?
iCHCKNG     Equ 0,$60          CHECKING
iOK         Equ 0,$5D
iQUERY      Equ 0,$5C          ?
iLOWBAT     Equ 0,$67          CHANGE BATTERY
*                              1,2,3 for each compartment
iONE1       Equ 1,$62          Compartment 1
iONE2       Equ 1,$63
iONE3       Equ 1,$64
iTWO1       Equ 1,$66          Compartment 2
iTWO2       Equ 1,$65
iTWO3       Equ 0,$65
iTWE1       Equ 1,$69          Compartment 3
iTWE2       Equ 0,$69
iTWE3       Equ 1,$6A
iFOUR1      Equ 1,$6C          Compartment 4
iFOUR2      Equ 1,$6D
iFOUR3      Equ 0,$6D

*           "Memory Register" addresses (variables)
Tx8         Equ $0             Tick count minutes/eight
Tx15        Equ $1             Tick count units
THour       Equ $2             Tens hours
UHour       Equ $3             Units hours
TMin        Equ $4             Tens mins
UMin        Equ $5             Units mins
GPreg       Equ $6             General Purpose register
DownT       Equ $7             Down time for buttons
WTHour      Equ $8             Tens hours (wake up)
WUHour      Equ $9             Units hours (wake up)
WTMin       Equ $A             Tens mins (wake up)
WUMin       Equ $B             Units mins (wake up)
*           $C, $D, $E, & $F are used for temporary time storage

*           Regular memory addresses (variables)
TxReg       Equ $70            bit 0 is show-time allowed flag
*                              bit 1 is odd/even day flag
```

Medi-Monitor Corporation - Confidential

MediMonitor assembly language program for Hitachi 4bit Microcontroller HD4074808, page 2
©1989, 1990 Current Designs Corporation, New York, NY, Medi-Monitor Corporation

```
*                          bit 2 is check alarms now flag
*                          bit 3 is 12/24 hour; 1=24 hour
Al Reg    Equ $71          Holds alarm active flags
Al2Reg    Equ $72          Alarm beeping timer
Al3Reg    Equ $73          Other Alarm beeping timer
HMP1      Equ $74          How many pills
HMP2      Equ $75          How many pills
HMP3      Equ $76          How many pills
HMP4      Equ $77          How many pills
which     Equ $78          Which compartment we're checking/setting
State     Equ $79          Tells which state we're in
City      Equ $7A          Tells which set-time mode we're in
*                          bit 0 is setting time of day
*                          bit 1 is setting wake-up time
*                          bit 2 is setting special schedule
*                          bit 3 is
Blink     Equ $7B          bit 0 is blinking time flag
*                          bit 1 is time-blanked flag
Timeout   Equ $7C          User inactivity timer
AlmTmr    Equ $7D          Alarm timer - turns on missed pill @ 1 hr.
MayIbep   Equ $7E          Beep timer (0=No beep)
BepOfTm   Equ $7F          Beep off time, hours (0 to 9)
*                  don't move the next 5 equ's
TypeT     Equ $80          Temp schedule type
*                          0=as needed, 5=every other day, 6=special
TypeS1    Equ $81          Compartment 1 schedule type
TypeS2    Equ $82          Compartment 2 schedule type
TypeS3    Equ $83          Compartment 3 schedule type
TypeS4    Equ $84          Compartment 4 schedule type
FlashPQ   Equ $85          Flash pill quantity flag
FlashAN   Equ $86          Flash AS NEEDED
FlashEO   Equ $87          Flash EVERY OTHER DAY
FlashSP   Equ $88          Flash SPECIAL
FlashTD   Equ $89          Flash TIMES PER DAY
BeepVol   Equ $8A          Beep Volume
SatThr    Equ $8B          Don't move - ShwATim private
SatUhr    Equ $8C          Don't move - ShwATim private
Return    Equ $8D          Holds previous state for NEXT/LAST
AlrMode   Equ $8E          1 (bit 0)     = Alarm
*                          3 (bit 0 & 1) = Alarm, Missed Pill
*                          7 (bit 0,1,2) = Alarm, Missed Pill, OK
BepOfST   Equ $8F          Beep off Sub Timer
*                  don't move the next 5 equ's
SpeciaT   Equ $90          Temp special schedule How Many Times
Special   Equ $91          Special schedule How Many Times
Specia2   Equ $92          Special schedule How Many Times
Specia3   Equ $93          Special schedule How Many Times
Specia4   Equ $94          Special schedule How Many Times
FlashQY   Equ $95          Flash ?
EODay     Equ $96          Every other day schedule indicator
DoorJam   Equ $97          Holds doors status
DorStop   Equ $98          Holds doors open
Stomach   Equ $99          Holds pills just taken
Skdlst    Equ $9A          Check Schedule first?
StoreLP   Equ $9B          Temporary Last Pill store
StoreMP   Equ $9C          Temporary Missed Pill store
FlagLB    Equ $9D          Low battery flag (Bit 0=1=low battery)
AfterM    Equ $9E          After midnight flag Xstack    Equ $E           Extra stack X part ($E0-$FF)
```

Medi-Monitor Corporation - Confidential

MediMonitor assembly language program for Hitachi 4bit Microcontroller HD4074808, page 3
©1989, 1990 Current Designs Corporation, New York, NY, Medi-Monitor Corporation

```
Ystack   Equ  $0           Extra stack Y part
Zstack   Equ  $E0          Extra stack both parts

*              ----------- This is the jump table ----------
         Org   $00         Forever
         JMPL  Reset       Reset - power up
         JMPL  Int0        Interrupt 0 - button inputs
         JMPL  Reset       Interrupt 1 - not used
         JMPL  TimerA      Timer A - every 1/2 second
         JMPL  Reset       Timer B - not used
         JMPL  Reset       Timer C - not used
         JMPL  Reset       Serial  - not used
         JMPL  Reset       Spare
*                          >>> end of jump table <<<

*        These subroutines must be located below $1000
ShwATim  Equ  $1B0         uses 2 pages of rom to show a time
*                          not in this module (assembled separately)
BtBrTbl  Equ  3            uses 6 pages of rom (1 for each button)
         Org  $300         if you change this, also change BtBrTbl

*              ------------- Button branch table -------------
*        This module contains the branch table for
*        the six buttons: Last, Next, Check, Set, Yes, No
*              Page 1 ( LAST button ) follows

*                          code for State 0 LAST - Last
         Lamd State
         Lmad Return       save state
         Lmid 14,State     switch to LAST
         Call LastA
         Jmpl ButWait
$0F      DC $3FF           code for State 1 LAST - Check Wake-up-Time
         nop
         Jmpl ButWait
$1F      DC $3FF           code for State 2 LAST - Check Schedule
         nop
         Jmpl ButWait
$2F      DC $3FF           code for State 3 LAST - Check Special Schedule
         Remd iTIPRDY
         Remd iNEXT
         Semd iLAST
         Semd iTIME
         Call GetLstA      get last alarm time
         Jmpl ButWait
$3F      DC $3FF           code for State 4 LAST - Set Pill Quantity
         Inemd 1,which
         Br Last41
         Jmpl SPQ1d        if which=1 Set Pill Quantity 1 down
Last41   Inemd 2,which
         Br Last42
         Jmpl SPQ2d        if which=2 Set Pill Quantity 2 down
Last42   Inemd 3,which
         Brs SPQ4d
         Jmpl SPQ3d
*4F                        code for State 5 LAST - Set Times per Day
         Lamd TypeT
         Lba
         Db
         Lab
```

Medi-Monitor Corporation - Confidential

MediMonitor assembly language program for Hitachi 4bit Microcontroller HD4074808, page 4
©1989, 1990 Current Designs Corporation, New York, NY, Medi-Monitor Corporation

```
        Br Last52       if type is in range
        Lai 6
Last52  Lmad TypeT
        Jmpl ShowTPD    show times per day
$5F     DC $3FF         code for State 6 LAST - Set Special Schedule
        nop
        Jmpl ButWait
$6F     DC $3FF         code for State 7 LAST - Alarm
        Inemd 3,AlrMode
        Brs ButWait     if not missed pill
        Lamd State
        Lmad Return     save state
        Lmid 14,State   switch to Last
        Call LastA      Last alarm time
        Jmpl ButWait
$7F     DC $3FF         Up to 12 byrds of code for State 8
        nop
        Jmpl ButWait
$8F     DC $3FF         code for State 9 LAST - Beep off Time
        Lamd BepOfTm
        Lba
        Db
        Br Last92       if => 0
        Br Last93
Last92  Lab
        Lmad BepOfTm    inc. beep off time
Last93  Call ShwBpOf
        Jmpl ButWait
$9F     DC $3FF         code for State 10 LAST - Unscheduled Pill
        nop
        Jmpl ButWait
$AF     DC $3FF         code for State 11 LAST - Set Beep Volume
        Lamd BeepVol
        Ai 15           subtract 1
        Alei 0
        Brs AdjVol      if = 0
        Lmad BeepVol
        Jmpl AdjVol
$BF     DC $3FF         code for State 12 LAST - Set Time
        Jmpl LAStime
$CF     DC $3FF         code for State 13 LAST - Next
        nop
        Jmpl ButWait
$DF     DC $3FF         code for State 14 LAST - Last
        Call Clear
        Semd iLAST
        Semd iTIME
        Call LastA5
        Jmpl ButWait
$EF     DC $3FF         code for State 15 LAST - Check Beep Volume
        nop
        Jmpl ButWait

*               Page 2 ( NEXT button ) follows $FF     DC $3FF         code for State 0 NEXT - Time of Day
        Lamd State
        Lmad Return     save state
        Lmid 13,State   switch to Next
        Call NextA      Next alarm time
```

Medi-Monitor Corporation — Confidential

MediMonitor assembly language program for Hitachi 4bit Microcontroller HD4074808, page 5
©1989, 1990 Current Designs Corporation, New York, NY, Medi-Monitor Corporation

```
            Jmpl ButWait
  $0F       DC $3FF         code for State 1 NEXT - Check Wake-up-Time
            nop
            Jmpl ButWait
  $1F       DC $3FF         code for State 2 NEXT - Check Schedule
            nop
            Jmpl ButWait
  $2F       DC $3FF         code for State 3 NEXT - Check Special Schedule
            Remd iTIPRDY
            Remd iLAST
            Semd iNEXT
            Semd iTIME
            Call GetNxtA
            Jmpl ButWait
  $3F       DC $3FF         code for State 4 NEXT - Set Pill Quantity
            Inemd 1,which
            Br NextB41
            Jmpl SPQ1u      if which=1 Set Pill Quantity 1 up
  NextB41   Inemd 2,which
            Br NextB42
            Jmpl SPQ2u      if which=2 Set Pill Quantity 2 up
  NextB42   Inemd 3,which
            Brs SPQ4u
            Jmpl SPQ3u
  *4F                       code for State 5 NEXT - Set Times per Day
            Lamd TypeT
            Ai 1
            Alei 6
            Br NextB52      if type is in range
            Lai 0
  NextB52   Lmad TypeT
            Jmpl ShowTPD    show times per day
  $5F       DC $3FF         code for State 6 NEXT - Set Special Schedule
            nop
            Jmpl ButWait
  $6F       DC $3FF         code for State 7 NEXT - Alarm
            Inemd 3,AlrMode
            Brs ButWait     if not missed pill
            Lamd State
            Lmad Return     save state
            Lmid 13,State   switch to Next
            Call NextA      Next alarm time
            Jmpl ButWait
  $7F       DC $3FF         Up to 12 byrds of code for State 8
            nop
            Jmpl ButWait
  $8F       DC $3FF         code for State 9 NEXT - Beep off Time
            Lamd BepOfTm
            Ai 1
            Alei 9
            Br Next92
            Br Next93       if > 9
  Next92    Lmad BepOfTm    inc. beep off time
  Next93    Call ShwBpOf
            Jmpl ButWait
  $9F       DC $3FF         code for State 10 NEXT - Unscheduled Pill
            nop
            Jmpl ButWait
  $AF       DC $3FF         code for State 11 NEXT - Set Beep Volume
            Lamd BeepVol
```

Medi-Monitor Corporation - Confidential

MediMonitor assembly language program for Hitachi 4bit Microcontroller HD4074808, page 6
©1989, 1990 Current Designs Corporation, New York, NY, Medi-Monitor Corporation

```
          Ai 1
          Alei 9
          Br NextBB2
          Jmpl AdjVol
NextBB2   Lmad BeepVol
          Jmpl AdjVol
$BF       DC $3FF        code for State 12 NEXT - Set Time
          Jmpl NXtime
$CF       DC $3FF        code for State 13 NEXT - Next
          Call Clear
          Semd iNEXT
          Semd iTIME
          Call PopWXY    this gets the present alarm address
          Iy
          Call NextA5
          Jmpl ButWait
$DF       DC $3FF        code for State 14 NEXT - Last
          nop
          Jmpl ButWait
$EF       DC $3FF        code for State 15 NEXT - Check Beep Volume
          nop
          Jmpl ButWait

*              Page 3 ( CHECK button ) follows $FF       DC $3FF        code for State 0 CHECK - Time-of-Day
StChkWU   Lmid 1,State   switch to check wake-up time
          Remd 0,TxReg   disallow show-time
          Call Clear
          Semd iFIRST
          Semd iTIME
          Semd iCHCKNG
          Jmpl ChkWU
$0F       DC $3FF        code for State 1 CHECK - Check Wake-up-Time
          Lmid 2,State   switch to check schedule
          Call Clear
          Lai 1
          Lmad which
          Jmpl ChkSkd
$1F       DC $3FF        code for State 2 CHECK - Check Schedule
          Call Clear
          Lamd which
          Ai 1
          Lmad which
          Alei 4
          Brs ChkSkd     if compartment <= 4
          Lmid 15,State  switch to check beep volume
          Jmpl ChkBeep
$2F       DC $3FF        code for State 3 CHECK - Check Special Schedule
          Lmid 2,State
          Br $20         trust me
          Jmpl ButWait
$3F       DC $3FF        code for State 4 CHECK - Set Pill Quantity
          nop
          Jmpl ButWait
$4F       DC $3FF        code for State 5 CHECK - Set Times per Day
          nop
          Jmpl ButWait
$5F       DC $3FF        code for State 6 CHECK - Set Special Schedule
          nop
```

MediMonitor assembly language program for Hitachi 4bit Microcontroller HD4074808, page 7
©1989, 1990 Current Designs Corporation, New York, NY, Medi-Monitor Corporation

```
            Jmpl ButWait
$6F         DC $3FF         code for State 7 CHECK - Alarm
            nop
            Jmpl ButWait
$7F         DC $3FF         Up to 12 byrds of code for State 8
            nop
            Jmpl ButWait
$8F         DC $3FF         code for State 9 CHECK - Beep off Time
            nop
            Jmpl ButWait
$9F         DC $3FF         code for State 10 CHECK - Unscheduled Pill
            nop
            Jmpl ButWait
$AF         DC $3FF         code for State 11 CHECK - Set Beep Volume
            Call Beep
            Jmpl ButWait
$BF         DC $3FF         code for State 12 CHECK - Set Time
            Tmd 0,City
            Br CheckC2      if setting time-of-day
            Br CheckC5
CheckC2     Tmd 3,TxReg
            Remd 3,TxReg
            Br CheckC3      if 24 hour, switch to 12 hour
            Semd 3,TxReg    and vice versa
CheckC3     Call ShwATim
CheckC5     Jmpl ButWait
$CF         DC $3FF         code for State 13 CHECK - Next
            nop
            Jmpl ButWait
$DF         DC $3FF         code for State 14 CHECK - Last
            nop
            Jmpl ButWait
$EF         DC $3FF         code for State 15 CHECK - Check Beep Volume
            Call BackTOD    back to time of day
            Jmpl ButWait

*                   Page 4 ( SET button ) follows $FF         DC $3FF         code for State 0 SET - Time-of-Day
            Lmid 12,State   set time
            Remd 0,TxReg    disallow show-time
            Semd 0,Blink    blinking the time display flag
            Lmid 1,City     setting time of day flag
            Semd iSET       turn on SET
            Semd iTIME      turn on TIME
            Jmpl ButWait
$0F         DC $3FF         code for State 1 SET - Check Wake-up-Time
            Lmid 12,State   set time
            Semd 0,Blink    blinking the time display flag
            Lmid 2,City     setting Wake-up-Time
            Semd iSET       turn on SET
            Remd iCHCKNG    turn off CHECKING
            Jmpl ButWait
$1F         DC $3FF         code for State 2 SET - Check Schedule
            Lmid 4,State    set pill quantity
            Semd iSET       turn on SET
            Remd iCHCKNG    turn off CHECKING
            Semd iHOWMNY    turn on HOW MANY?
            Lmid 1,FlashPQ  flash pill quantity
            Jmpl ButWait
```

Medi-Monitor Corporation - Confidential

MediMonitor assembly language program for Hitachi 4bit Microcontroller HD4074808, page 8
©1989, 1990 Current Designs Corporation, New York, NY, Medi-Monitor Corporation

```
$2F     DC $3FF         code for State 3 SET - Check Special Schedule
        Remd iNEXT
        Remd iLAST
        Remd iTIME
        Call ClrTime
        Br $20
        Br $20
        Jmpl ButWait
$3F     DC $3FF         code for State 4 SET - Set Pill Quantity
        nop
        Jmpl ButWait
$4F     DC $3FF         code for State 5 SET - Set Times per Day
        nop
        Jmpl ButWait
$5F     DC $3FF         code for State 6 SET - Set Special Schedule
        nop
        Jmpl ButWait
$6F     DC $3FF         code for State 7 SET - Alarm
        nop
        Jmpl ButWait
$7F     DC $3FF         Up to 12 byrds of code for State 8
        nop
        Jmpl ButWait
$8F     DC $3FF         code for State 9 SET - Beep off Time
        nop
        Jmpl ButWait
$9F     DC $3FF         code for State 10 SET - Unscheduled Pill
        nop
        Jmpl ButWait
$AF     DC $3FF         code for State 11 SET - Set Beep Volume
        nop
        Jmpl ButWait
$BF     DC $3FF         code for State 12 SET - Set Time
        nop
        Jmpl ButWait
$CF     DC $3FF         code for State 13 SET - Next
        nop
        Jmpl ButWait
$DF     DC $3FF         code for State 14 SET - Last
        nop
        Jmpl ButWait
$EF     DC $3FF         code for State 15 SET - Check Beep Volume
        Lmid 11,State   set beep volume
        Call Clear
        Semd 0,Blink    blinking the time display flag
        Semd iSET       turn on SET
        Semd iBEEP
        Semd iVOLUME
        Jmpl ButWait

*               Page 5 ( YES button ) follows $FF     DC $3FF         code for State 0 YES - Time of Day
        Redd 5          power up comparator bridge (for testing)
        Lai 1
        Xmra DownT      start timing button press
        Jmpl ButWait
$0F     DC $3FF         code for State 1 YES - Check Wake-up Time
        Call BackTOD    back to time of day
        Jmpl ButWait
```

Medi-Monitor Corporation - Confidential

MediMonitor assembly language program for Hitachi 4bit Microcontroller HD4074808, page 9
©1989, 1990 Current Designs Corporation, New York, NY, Medi-Monitor Corporation

```
$1F     DC $3FF         code for State 2 YES - Check Schedule
        Call BackTOD    back to time of day
        Jmpl ButWait
$2F     DC $3FF         code for State 3 YES - Check Special Schedule
        Call BackTOD    back to time of day
        Jmpl ButWait
$3F     DC $3FF         code for State 4 YES - Set Pill Quantity
        Lmid 5,State    set times per day
        Remd iHOWMNY    turn off HOW MANY?
        Remd 0,FlashPQ  pill quantity on steady
        Jmpl ShowTPD    show times per day
$4F     DC $3FF         code for State 5 YES - Set Times per Day
* 1. find out if special
* 2. if special, switch to set special
* 3. if regular, set type, install schedule & switch to check schedule
        Inemd 6,TypeT
        Br Set52        if not special
        Remd 0,FlashSP  set special on steady
        Remd iTIPRDY    turn off TIMES PER DAY
        Semd iTIME      turn on TIME
        Jmpl Spcl00     continue...
Set52   Lmid 2,State    check schedule
        Jmpl InstalS    install schedule
$5F     DC $3FF         code for State 6 YES - Set Special Schedule
        Remd iQUERY     turn off ?
        Lmid 0,FlashQY  stop flash ?
        Semd 0,Blink
        Lmid 12,State   switch to Set Time
        Jmpl ButWait
$6F     DC $3FF         code for State 7 YES - Alarm
        Inemd 3,AlrMode
        Brs MisPOK      if not missed pill, continue check
        Lmid 7,AlrMode  change Alarm mode to Missed Pill OK?
        Semd iOK
        Semd iQUERY
        Jmpl ButWait
$7F     DC $3FF         Up to 12 byrds of code for State 8
        nop
        Jmpl ButWait
$8F     DC $3FF         code for State 9 YES - Beep off Time
        Call BackTOD    back to time of day
        Jmpl ButWait
$9F     DC $3FF         code for State 10 YES - Unscheduled Pill
        Call RemPill    remember pills taken
        Alei 15         make ST=1
        Call BackTOD    back to time of day
        Jmpl ButWait
$AF     DC $3FF         code for State 11 YES - Set Beep Volume
        Call BackTOD    back to time of day
        Jmpl ButWait
$BF     DC $3FF         code for State 12 YES - Set Time
        Tmd 1,City
        Brs InWake      if setting wake-up time, install new
        Tmd 2,City
        Brs SpclIn      if setting special, install
        Call BackTOD    back to time of day
        Jmpl ButWait
$CF     DC $3FF         code for State 13 YES - Next
        Lamd Return     restore state
        Lmad State
```

Medi-Monitor Corporation — Confidential

MediMonitor assembly language program for Hitachi 4bit Microcontroller HD4074808, page 10
©1989, 1990 Current Designs Corporation, New York, NY, Medi-Monitor Corporation

```
            Call Clear
            Semd 0,TxReg    allow show-time
            Call ShowTim
            Jmpl ButWait
$DF         DC $3FF         code for State 14 YES - Last
            Lamd Return     restore state
            Lmad State
            Call Clear
            Semd 0,TxReg    allow show-time
            Call ShowTim
            Jmpl ButWait
$EF         DC $3FF         code for State 15 YES - Check Beep Volume
            Call BackTOD    back to time of day
            Jmpl ButWait

*                   Page 6 ( NO button ) follows $FF         DC $3FF         code for State 0 NO - Time of Day
            Lai 1
            Xmra DownT      start timing button press
            Jmpl ButWait
$0F         DC $3FF         code for State 1 NO - Check Wake-up Time
            Call BackTOD    back to time of day
            Jmpl ButWait
$1F         DC $3FF         code for State 2 NO - Check Schedule
            Call BackTOD    back to time of day
            Jmpl ButWait
$2F         DC $3FF         code for State 3 NO - Check Special Schedule
            Call BackTOD    back to time of day
            Jmpl ButWait
$3F         DC $3FF         code for State 4 NO - set pill quantity
            Call BackTOD    back to time of day
            Jmpl ButWait
$4F         DC $3FF         code for State 5 NO - Set Times per Day
            Call BackTOD    back to time of day
            Jmpl ButWait
$5F         DC $3FF         code for State 6 NO - Set Special Schedule
            Jmpl SpclEnf    this switches back to Check Schedule
$6F         DC $3FF         code for State 7 NO - Alarm
            Inemd 7,AlrMode
            Br No72         if not Missed Pill OK?
            Lmid 3,AlrMode  switch back to Missed Pill
            Remd iOK
            Remd iQUERY
No72        Lmid 0,MayIbep  stop beeping
            Jmpl ButWait
$7F         DC $3FF         Up to 12 byrds of code for State 8
            nop
            Jmpl ButWait
$8F         DC $3FF         code for State 9 NO - Beep off Time
            Lamd BepOfTm
            Ai 1
            Alei 9
            Br No92
            Br No93         if > 9
No92        Lmad BepOfTm    inc. beep off time
No93        Call ShwBpOf
            Jmpl ButWait
$9F         DC $3FF         code for State 10 NO - Unscheduled Pill
            Call BackTOD    back to time of day
```

Medi-Monitor Corporation — Confidential

MediMonitor assembly language program for Hitachi 4bit Microcontroller HD4074808, page 11
©1989, 1990 Current Designs Corporation, New York, NY, Medi-Monitor Corporation

```
              Jmpl ButWait
$AF           DC $3FF         code for State 11 NO - Set Beep Volume
              nop
              Jmpl ButWait
$BF           DC $3FF         code for State 12 NO - Set Time
              nop
              Jmpl ButWait
$CF           DC $3FF         code for State 13 NO - Next
              Lamd Return     restore state
              Lmad State
              Call Clear
              Semd 0,TxReg    allow show-time
              Call ShowTim
              Jmpl ButWait
$DF           DC $3FF         code for State 14 NO - Last
              Lamd Return     restore state
              Lmad State
              Call Clear
              Semd 0,TxReg    allow show-time
              Call ShowTim
              Jmpl ButWait
$EF           DC $3FF         code for State 15 NO - Check Beep Volume
              Call BackTOD    back to time of day
              Jmpl ButWait
*                             >>> end of Button Branch Table <<<

Org $1000       start of Reset/Main
*             ---------- Timer A interrupt - every 1/2 second ---------
TimerA        Lamr DownT
              Ai 1            increment downtime
              Xmra DownT
              Remd 2,$1       reset timer A interrupt flag
              Lar 2           get door switches into A
              Anemd DoorJam
              Call Doors      if changed
              Tmd 0,DownT+$40
              Brs Timer9      every second
              Inemd 0,AlReg   alarms reg
              Call SndAlrm    if active alarm
Timer9        Tmd 0,TxReg
              Brs DoColon     if show-time is allowed
              Call Flasher    if show-time is not allowed
Timer11       Lamr Tx15
              Ai 1            add 1 to Tx15
              Brs Timer2      overflow, so do stage 2
              Xmra Tx15
              Tmd 2,TxReg     check-alarms flag
              Call ChkAlrm    every 5 min.
              Rtni
Timer2        Lai 1           we get here every 7.5 sec.
              Xmra Tx15       make Tx15=1
              Ilemd 12,Timeout
              Brs Timer10     if Timeout > 11, it's not timing out
              Lamd Timeout
              Ai 1            inc. Timeout
              Lmad Timeout
              Alei 11
              Brs Timer10     if not timed out yet
              Call BackTOD    if no button push for 1 min.
Timer10       Lamr Tx8        add 1 to Tx8
```

Medi-Monitor Corporation — Confidential

MediMonitor assembly language program for Hitachi 4bit Microcontroller HD4074808, page 12
©1989, 1990 Current Designs Corporation, New York, NY, Medi-Monitor Corporation

```
         Ai 1
         Brs Timer5      overflow, so do stage 3
         Xmra Tx8
         Rtni
Timer5   Lai 8           we get here once a min.
         Xmra Tx8        make Tx8=8
         Call NextMin
         Inemd 0,UMin+$40
         Brs Timer6      if unit min not 0
         Brs Timer7
Timer6   Inemd 5,UMin+$40
         Brs Timer8      if unit min not 0 or 5, don't check alarms
Timer7   Semd 2,TxReg    set check-alarms flag every 5 min.
         Inemd 0,BepOfTm
         Call DecBpTm    decrement beep-off timer if running
Timer8   Tmd 0,TxReg
         Call ShowTim    if show-time is allowed
         Rtni
DoColon  Tmd iCOLON      test colon
         Brs Timer4      if colon is on
         Semd iCOLON
         Brs Timer11
Timer4   Remd iCOLON     turn it off
         Brs Timer11     >>> end of Timer A interrupt <<<

Beep     Lyi 4           about 4500-1800 Hz for 43-68 ms
         Xspy
         Lyi 12
         Lamd BeepVol
         Nega
         Ai 9
         Syy             outer loop number
         Xmra GPreg
Beep4    Xspy            now Y=port#
         Lbi 15          middle loop number
         nop             minimum middle loop=288, 1=352, 3=480
Beep3    Red             5=608, 7=736, 9=864
         Sedd 7
         nop             time killers
         nop
Beep1    Lamr GPreg      sets frequency
Beep2    Ai 15
         Brs Beep2       if not done
         Td
         Brs Beep3       if set, reset
         Sed
         Redd 7
         Db
         Brs Beep1       not done yet
         Xspy
         Dy
         Brs Beep4       still not done
         Sedd 7
         Rtn             status=1 on return Wait     Lyi 6           about 33 ms.
Wait4    Lbi 15
Wait2    Ai 15
         Brs Wait2       inner loop
         Db
```

MediMonitor assembly language program for Hitachi 4bit Microcontroller HD4074808, page 13
©1989, 1990 Current Designs Corporation, New York, NY, Medi-Monitor Corporation

```
        Brs Wait2       middle loop
        Dy
        Brs Wait4       outer loop
        Rtn             status=1 on return Flasher Inemd 0,Blink   blink time flags
        Call BlinkIt    if blinking
        Inemd 0,FlashPQ
        Call FlshPQ     Flash pill quantity
        Inemd 0,FlashAN
        Call FlshAN     Flash AS NEEDED
        Inemd 0,FlashEO
        Call FlshEO     Flash EVERY OTHER DAY
        Inemd 0,FlashSP
        Call FlshSP     Flash SPECIAL
        Inemd 0,FlashTD
        Call FlshTD     Flash TIMES PER DAY
        Inemd 0,FlashQY
        Call FlshQY     Flash ?
        Rtn FlshEO  Tmd 1,FlashEO
        Brs FlshEO2     if display is off, un-blank it
        Semd 1,FlashEO
        Remd iEVYODY    if on, blank it
        Rtn
FlshEO2 Remd 1,FlashEO
        Semd iEVYODY
        Rtn FlshAN  Tmd 1,FlashAN
        Brs FlshAN2
        Semd 1,FlashAN
        Remd iASNEED
        Rtn
FlshAN2 Remd 1,FlashAN
        Semd iASNEED
        Rtn FlshSP  Tmd 1,FlashSP
        Brs FlshSP2
        Semd 1,FlashSP
        Remd iSPCIAL
        Rtn
FlshSP2 Remd 1,FlashSP
        Semd iSPCIAL
        Rtn FlshTD  Tmd 1,FlashTD
        Brs FlshTD2
        Semd 1,FlashTD
        Remd iTIPRDY
        Rtn
FlshTD2 Remd 1,FlashTD
        Semd iTIPRDY
        Rtn FlshQY  Tmd 1,FlashQY
        Brs FlshQY2
        Semd 1,FlashQY
```

Medi-Monitor Corporation - Confidential

MediMonitor assembly language program for hitachi 4bit Microcontroller HD4074808, page 14
©1989, 1990 Current Designs Corporation, New York, NY, Medi-Monitor Corporation

```
        Remd iQUERY
        Rtn
FlshQY2 Remd 1,FlashQY
        Semd iQUERY
        Rtn

*       0,Blink is the blinking-active flag and is used
*       to attract the program here. Bits 2 & 3 are not used.
BlinkIt Tmd 1,Blink      display-blanked flag
        Brs Blink2       if display is off, un-blank it
        Semd 1,Blink
ClrTime Lwi 0
        Lxi Xstack
        Lyi Ystack
        Lai 11
        Xmra $C          put 11 in MR's $CDEF
        Lmaiy            and put original $CDEF on private stack
        Lai 11
        Xmra $D
        Lmaiy
        Lai 11
        Xmra $E
        Lmaiy
        Lai 11
        Xmra $F
        Lmaiy
        Call ShwATim     blank time display
        Lamd Zstack
        Xmra $C
        Lamd Zstack+$1
        Xmra $D
        Lamd Zstack+$2
        Xmra $E
        Lamd Zstack+$3
        Xmra $F          restore $CDEF from private stack
        Rtn
Blink2  Remd 1,Blink
Blink3  Jmpl ShwATim     you better have the right time in $CDEF DecBpTm Lamd BepOfST     ----- Decrement Beep Off Timer -----
        Ai 1
        Brs DecBpT2      if an hour
        Lmad BepOfST     inc sub timer (12 per hour)
        Rtn
DecBpT2 Lmid 4,BepOfST   re-start sub timer
        Lamd BepOfTm
        Ai 15            subtract 1
        Lmad BepOfTm
        Alei 0
        Brs DecBpT3      if timed out
        Rtn
DecBpT3 Remd iNOBELL
        Rtn

*       --------------- Next minute ---------------
NextMin Lamr UMin
        Ai 1             add 1 to units mins
        Alei 9           status gets set if A <= 9
        Xmra UMin        save
        Brs Next5        if units mins < 10
```

Medi-Monitor Corporation — Confidential

MediMonitor assembly language program for Hitachi 4bit Microcontroller HD4074808, page 15
©1989, 1990 Current Designs Corporation, New York, NY, Medi-Monitor Corporation

```
        Lmid 0,UMin+$40   zero > UMin
        Lamr TMin
        Ai 1              inc. tens mins
        Alei 5
        Xmra TMin
        Brs Next5         if tens min < 6
        Lmid 0,TMin+$40   zero > TMin
        Lamr UHour
        Ai 1              inc. units hours
        Xmra UHour
        Inemd 4,UHour+$40
        Brs Next3         if UHour not 4
        Lamr THour
        Alei 1
        Brs Next5         if tens hours < 2
        Lmid 0,THour+$40  zero > THour
        Lmid 0,UHour+$40  zero > UHour
        Tmd 1,TxReg
        Brs Next2         if it's an odd day
        Semd 1,TxReg      otherwise make it an odd day
        Rtn
Next2   Remd 1,TxReg      make it an even day
        Rtn               we just started a new day
Next3   Lamr UHour
        Alei 9
        Brs Next5         if units hours < 10
        Lmid 0,UHour+$40  zero > UHour
        Lamr THour
        Ai 1              inc. tens hours
        Xmra THour
Next5   Rtn Nxt5Min Lamr $F
        Ai 5              add 5 to units mins
        Alei 9            status gets set if A <= 9
        Xmra $F           save
        Brs Next55        if units mins < 10
        Lmid 0,$4F        zero > UMin
        Lamr $E
        Ai 1              inc. tens mins
        Alei 5
        Xmra $E
        Brs Next55        if tens min < 6
        Lmid 0,$4E        zero > TMin
        Lamr $D
        Ai 1              inc. units hours
        Xmra $D
        Inemd 4,$4D
        Brs Next35        if UHour not 4
        Lamr $C
        Alei 1
        Brs Next55        if tens hours < 2
        Lmid 0,$4C        zero > THour
        Lmid 0,$4D        zero > UHour
        Rtn
Next35  Lamr $D
        Alei 9
        Brs Next55        if units hours < 10
        Lmid 0,$4D        zero > UHour
        Lamr $C
```

Medi-Monitor Corporation – Confidential

MediMonitor assembly language program for Hitachi 4bit Microcontroller HD4074808, page 16
©1989, 1990 Current Designs Corporation, New York, NY, Medi-Monitor Corporation

```
              Ai 1              inc. tens hours
              Xmra $C
     Next55   Rtn ShowTim  Lamr THour        Tens hours
              Xmra $C
              Lamr UHour        Units hours
              Xmra $D
              Lamr TMin         Tens mins
              Xmra $E
              Lamr UMin         Units mins
              Xmra $F
              Jmpl ShwATim

*        --------------- Check Alarms (every 5 min.) -------------
     ChkAlrm  Remd 2,TxReg      reset check-alarms flag
              Lamd AlmTmr
              Ai 1              inc. alarm timer
              Alei 1
              Brs ChkA5         if alarm timer not running (0)
              Lmad AlmTmr
              Alei 12
              Brs ChkA5         if < 1 hour
              Lmid 0,AlmTmr     reset alarm timer
              Semd iMISSED      turn on MISSED PILL
              Semd 1,AlrMode    Alarm mode = missed pill
     ChkA5    Lmid 1,$3F        bank select=1 (permanent record)
              Redd 5            power up comparator bridge
              Lmid %1001,$12    PMRB - switch D12 to analog mode
              Call Ct2AA        now WXY has alarm address
              Remd 0,FlagLB
              Tdd 12            test comparator output
              Brs ChkA7         if battery > ref.
              Semd 0,FlagLB     Low battery flag
              Semd iLOWBAT
     ChkA7    Lmid %1000,$12    PMRB - switch D12 to digital mode
              Sedd 5            power down comparator bridge
              Lai 0
              Lma               clear this permanent record
              Lmid 0,$3F        bank select=0 (pill schedule)
              Inem 0
              Brs ChkA2         if there is an alarm
              Rtn
     ChkA2    Lam               find out if this is an E.O.D. pill
              Tmd 1,TxReg       odd/even day flag
              Brs ChkA3         if it's pill day
              Anmd EODay        (AND) daily bit=1; E.O.D. bit=0
              Brs ChkA3         if we still have an alarm
              Rtn
     ChkA3    Ormd AlReg        OR new alarm with old alarm
              Lmad AlReg        and save it
              Lmid 1,AlmTmr     start alarm timer
              Lmid 1,MayIbep    start beep timers
              Lmid 0,Al2Reg
              Lmid 0,Al3Reg
              Rtn

*        ------------------ Sound Alarm -------------------
     *        This gets called 60 times a min. if there is an alarm.
     *        AlReg holds the alarm flags for the 4 compartments.
```

Medi-Monitor Corporation - Confidential

MediMonitor assembly language program for Hitachi 4bit Microcontroller HD4074808, page 17
©1989, 1990 Current Designs Corporation, New York, NY, Medi-Monitor Corporation

```
*           If set, the alarm is active, but not necessarily
*           beeping or flashing.
SndAlrm   Inemd 10,State
          Brs SndAlr2      if not Unscheduled Pill
          Rtn
SndAlr2   Inemd 7,State
          Brs SndAlr4      if not Alarm
          Brs SndAlr5      if it's 7, alarm
SndAlr4   Inemd 13,State
          Brs SndAlr3      if not Next
          Brs SndAlr8      if Next
SndAlr3   Inemd 14,State
          Brs SndAlr7      if not Last
SndAlr8   Inemd 3,AlrMode
          Brs SndAlr7      if not Alarm missed pill & NEXT/LAST
          Brs SndAlr5
SndAlr7   Call BackTOD     clear out crap
          Lmid 7,State     switch to alarm
          Semd 0,AlrMode   Alarm mode = Alarm
          Remd 2,AlrMode   reset Missed Pill OK
SndAlr5   Tmd 1,AlrMode
          Brs SndAlr6      if missed pill
SndAlr9   Inemd 0,MayIbep
          Call BeepTw      beep twice (only for alarm)
          Tmd 0,AlReg
          Call S1HMP       if alarm, flash LED for 6 ms. & turn on HMP
          Tmd 1,AlReg      HMP= How Many Pills
          Call S2HMP
          Tmd 2,AlReg
          Call S3HMP
          Tmd 3,AlReg
          Call S4HMP
          Rtn
SndAlr6   Tmd 0,TxReg
          Brs SndAlrG      if show-time is allowed
          Brs SndAlr9
SndAlrG   Semd iMISSED     turn on MISSED PILL
          Brs SndAlr9

MisPOK    Inemd 7,AlrMode  -------> Missed Pill OK? --------
          Brs ButWait      if some other Alarm mode
          Lmid 0,AlReg     reset (cancel) alarms
          Lmid 0,AlmTmr    reset (cancel) alarm timer
          Lmid 0,AlrMode   reset alarm mode
          Alei 15          make ST=1
          Call BackTOD
          Jmpl ButWait

*          ------------ Find out which door is open -----------
*          This subroutine gets called from Timer A
*          if there is a change in the number of open doors.
Doors     Lmad DoorJam     jam in the latest status
          Alei 14
          Brs Doors2       if any door is open
          Rtn
Doors2    Lba
          Lya              temp. hold door status
          Comb             now B has inverted door status (open=1)
          Lab
          Lmad DorStop
```

Medi-Monitor Corporation - Confidential

MediMonitor assembly language program for Hitachi 4bit Microcontroller HD4074808, page 18
©1989, 1990 Current Designs Corporation, New York, NY, Medi-Monitor Corporation

```
          Inemd 7,State    Alarm
          Brs Doors5       if not
          Anmd AlReg       alarm AND door open = gulp
          Lmad Stomach     save
          Lay
          Anmd AlReg       if alarm AND door closed, alarm continues
          Lmad AlReg
          Brs Doors4       if more alarms
          Lmid 0,State     no alarms, so return to Time-of-Day
          Remd iMISSED     turn off MISSED PILL
          Lmid 3,Timeout   turn off HMP in 1 min
          Lmid 0,AlmTmr    reset (cancel) alarm timer
          Lmid 0,AlrMode   reset alarm mode
Doors4    Inemd 0,Stomach
          Brs Doors6       if pills taken
          Call Beep
          Rtn
*         ------ add pills taken to your permanent record ------
RemPill   Lamd DorStop
          Lmad Stomach
Doors6    Call Ct2AA
          Lmid 1,$3F       bank select=1 (permanent record)
          Lamd Stomach     holds pills just in
          Orm
          Lma
          Rtn
Doors5    Lmid 10,State    switch to Unscheduled Pill
          Remd 0,TxReg     disallow show-time
          Call Clear
          Semd iUNSKPL
          Tmd 0,DorStop
          Call S1HMPn      show how many pills
          Tmd 1,DorStop
          Call S2HMPn
          Tmd 2,DorStop
          Call S3HMPn
          Tmd 3,DorStop
          Call S4HMPn
          Lmid 3,Timeout   reset Timeout
          Call Beep
          Rtn S1HMP     Lyi 2
          Call FlashL
          Ilemd 11,State
          Brs S1HMP5       if state is LAST or NEXT, return
S1HMPn    Remd iONE1       ------ Show how many pills 1 ------
          Remd iONE2       turn off 1 2 & 3
          Remd iONE3
          Tmd 1,FlashPQ    1=on
          Brs S1HMP5       if display is on, blank it
          Inemd 1,HMP1
          Brs S1HMP2       if not 1 pill
          Semd iONE1       light up 1 over compartment 1
S1HMP5    Rtn
S1HMP2    Inemd 2,HMP1
          Brs S1HMP3       if not 2 pills
          Semd iONE2       light up 2 over compartment 1
          Rtn
S1HMP3    Semd iONE3       light up 3 over compartment 1
```

Medi-Monitor Corporation – Confidential

MediMonitor assembly language program for Hitachi 4bit Microcontroller HD4074808, page 19
©1989, 1990 Current Designs Corporation, New York, NY, Medi-Monitor Corporation

```
        Rtn             ST=1 on rtn

S2HMP   Lyi 1
        Call FlashL     flash LED
        Ilemd 11,State
        Brs S1HMP5      if state is LAST or NEXT, return
S2HMPn  Remd iTWO1
        Remd iTWO2      turn off 1 2 & 3
        Remd iTWO3
        Tmd 1,FlashPQ   1=on
        Brs S2HMP5      if display is on, blank it
        Inemd 1,HMP2
        Brs S2HMP2      if not 1 pill
        Semd iTWO1      light up 1 over compartment 2
S2HMP5  Rtn
S2HMP2  Inemd 2,HMP2
        Brs S2HMP3      if not 2 pills
        Semd iTWO2      light up 2 over compartment 2
        Rtn
S2HMP3  Semd iTWO3      light up 3 over compartment 2
        Rtn S3HMP   Lyi 0
        Call FlashL
        Ilemd 11,State
        Brs S1HMP5      if state is LAST or NEXT, return
S3HMPn  Remd iTWE1
        Remd iTWE2      turn off 1 2 & 3
        Remd iTWE3
        Tmd 1,FlashPQ   1=on
        Brs S3HMP5      if display is on, blank it
        Inemd 1,HMP3
        Brs S3HMP2      if not 1 pill
        Semd iTWE1      light up 1 over compartment 3
S3HMP5  Rtn
S3HMP2  Inemd 2,HMP3
        Brs S3HMP3      if not 2 pills
        Semd iTWE2      light up 2 over compartment 3
        Rtn
S3HMP3  Semd iTWE3      light up 3 over compartment 3
        Rtn S4HMP   Lyi 3
        Call FlashL
        Ilemd 11,State
        Brs S1HMP5      if state is LAST or NEXT, return
S4HMPn  Remd iFOUR1
        Remd iFOUR2     turn off 1 2 & 3
        Remd iFOUR3
        Tmd 1,FlashPQ   1=on
        Brs S4HMP5      if display is on, blank it
        Inemd 1,HMP4
        Brs S4HMP2      if not 1 pill
        Semd iFOUR1     light up 1 over compartment 4
S4HMP5  Rtn
S4HMP2  Inemd 2,HMP4
        Brs S4HMP3      if not 2 pills
        Semd iFOUR2     light up 2 over compartment 4
        Rtn
S4HMP3  Semd iFOUR3     light up 3 over compartment 4
```

Medi-Monitor Corporation — Confidential

MediMonitor assembly language program for Hitachi 4bit Microcontroller HD4074808, page 20
©1989, 1990 Current Designs Corporation, New York, NY, Medi-Monitor Corporation

```
        Rtn

*       ----- Flash Pill Quantity for Compartment(which) -----
FlshPQ  Tmd 1,FlashPQ   1=off
        Brs FlshPQ5     if display is off, un-blank it
        Semd 1,FlashPQ  and vice-versa
        Brs FlshPQ6
FlshPQ5 Remd 1,FlashPQ
FlshPQ6 Inemd 1,which
        Brs FlshPQ2
        Brs S1HMPn
FlshPQ2 Inemd 2,which
        Brs FlshPQ3
        Brs S2HMPn
FlshPQ3 Inemd 3,which
        Brs S4HMPn
        Brs S3HMPn FlashL  Lai 0
        Lbi 15
        Red             LED on
FlashL1 Db
        Brs FlashL1     wait 6 ms.
        Ai 1
        Brs FlashL2     if done
        Brs FlashL1
FlashL2 Sed             LED off
        Rtn Clear   Lwi 0           MS 2 bits
        Lbi 1           loop counter
        Lai 5           middle 4 bits
        Lxa             middle 4 bits
        Lyi 0           LS 4 bits
        Call Reset2     clear display memory $50 - $6F
        Tmd 0,FlagLB    Low battery flag
        Brs Clear3      if low
Clear4  Inemd 0,BepOfTm
        Brs Clear2      if beep off time > 0
        Rtn
Clear2  Semd iNOBELL
        Rtn
Clear3  Semd iLOWBAT
        Brs Clear4

*       --------------- Last minute ----------------
LastMin Lamr UMin
        Lba
        Db              decrement units mins
        Lab
        Xmra UMin       save
        Brs Last5       if units mins =>0
        Lmid 9,UMin+$40 9 > UMin
        Lamr TMin
        Lba
        Db              decrement tens mins
        Lab
        Xmra TMin
        Brs Last5       if tens min =>0
        Lmid 5,TMin+$40 5 > TMin
```

Medi-Monitor Corporation — Confidential

MediMonitor assembly language program for Hitachi 4bit Microcontroller HD4074808, page 21
©1989, 1990 Current Designs Corporation, New York, NY, Medi-Monitor Corporation

```
           Lamr UHour
           Lba
           Db                decrement units hours
           Lab
           Xmra UHour
           Brs Last5         if units hours =>0
           Lmid 9,UHour+$40  9 > UHour
           Lamr THour
           Lba
           Db                decrement tens hours
           Lab
           Xmra THour
           Brs Last5         if tens hours =>0
           Lmid 2,THour+$40  2 > THour
           Lmid 3,UHour+$40  3 > UHour
           Tmd 1,TxReg
           Brs Last2         if odd
           Semd 1,TxReg      make it odd
           Rtn
Last2      Remd 1,TxReg      make it even
Last5      Rtn Las5min    Lamr $F           units mins
           Ai 14
           Lai 0
           Xmra $F           save as 0
           Brs Las52         if ovf, it was 5 and we're done
           Lai 5
           Xmra $F           save
           Lamr $E
           Lba
           Db                decrement tens mins
           Lab
           Xmra $E
           Brs Las52         if tens min =>0
           Lmid 5,$E+$40     5 > TMin
           Lamr $D
           Lba
           Db                decrement units hours
           Lab
           Xmra $D
           Brs Las52         if units hours =>0
           Lmid 9,$D+$40     9 > UHour
           Lamr $C
           Lba
           Db                decrement tens hours
           Lab
           Xmra $C
           Brs Las52         if tens hours =>0
           Lmid 2,$C+$40     2 > THour
           Lmid 3,$D+$40     3 > UHour
Las52      Rtn

*          -------------- Clock time to Alarm time -------------
*          Calling parameters: Tens hours in Y, Units hours in A
*          Returns MSB of alarm address in WX
Ct2At      Lbi 1
Ct2At2     Dy
           Brs Ct2At3        if Y >= 0
           Brs Ct2At5        if Y < 0
```

Medi-Monitor Corporation — Confidential

MediMonitor assembly language program for Hitachi 4bit Microcontroller HD4074808, page 22
©1989, 1990 Current Designs Corporation, New York, NY, Medi-Monitor Corporation

```
Ct2At3    Ai 10
          Brs Ct2At4      if units hours > 15
          Brs Ct2At2
Ct2At4    Ib
Ct2At5    Lxa
          Lab
          Lwa
          Rtn

*         ----------- Clock time to Alarm address ----------
Ct2AA     Lamr THour
          Lya
          Lamr UHour
          Lbi 1
Ct2Aa2    Dy
          Brs Ct2Aa3      if THour >= 0
          Brs Ct2Aa5      if < 0
Ct2Aa3    Ai 10
          Brs Ct2Aa4      if units hours > 15
          Brs Ct2Aa2
Ct2Aa4    Ib
Ct2Aa5    Lxa
          Lab
          Lwa
          Lamr TMin
          Sec
          Ilemd 5,UMin+$40
          Brs Ct2Aa6      if 5 <= unit min.
          Rec
Ct2Aa6    Rotl            convert tens min to alarm min
          Lya             now alarm address is in WXY
          Rtn             ST=1 on rtn WXY2CT    Law     ------- Alarm address to clock time -------
          Alei 1
          Xspx            .
          Laspx           .
          Xspx            X > A
          Brs WXY2c2      if before 16:00
          Ai 6
          Alei 9
          Lmid 1,$4C      Thour
          Brs WXY2c3      if before 20:00
          Lmid 2,$4C      Thour
WXY2c4    Ai 6
WXY2c3    Xmra $D         Uhour
          Lay             do minutes
          Rec
          Rotr
          Xmra $E         Tmin
          Tc
          Lmid 5,$4F      Umin
          Brs WXY2c5      if odd (5 min)
          Lmid 0,$4F      Umin
WXY2c5    Rtn
WXY2c2    Lmid 0,$4C      Thour
          Alei 9
          Brs WXY2c3      if before 10:00
          Lmid 1,$4C      Thour
          Brs WXY2c4
```

Medi-Monitor Corporation — Confidential

MediMonitor assembly language program for Hitachi 4bit Microcontroller HD4074808, page 23
©1989, 1990 Current Designs Corporation, New York, NY, Medi-Monitor Corporation

```
*               --------------- Reset and Main ---------------
Reset   Semd 1,$1        Mask int 1
        Semd 1,$2        Mask timer B
        Semd 3,$2        Mask timer C
        Semd 1,$3        Mask serial
        Lmid %0100,$4    PMRA port mode reg A
        Lmid %1010,$8    TMA timer mode A=32kHz clock, 1/2 s interrupt
        Lmid %0101,$C    MIS register  31 ms.
        Lmid %1000,$12   PMRB port mode reg B
        Lmid %0111,$13   LCR LCD control
        Lmid %0010,$14   LMR LCD clock control
        Lmid %1111,$3B   DCRB - discreet ports 0-3
*       DCR is the port control register, 1=out, 2=in
        Lmid %1111,$3C   DCRC - discreet ports 4-7
        Lwi 0            MS 2 bits
        Lbi 8            loop counter
        Lai 7            middle 4 bits
        Lxa              middle 4 bits
        Lyi 1            LS 4 bits
        Dy               to set status
        Call Reset2      clear memory $70-$FF
        Lmid 11,TxReg    Time control reg
        Lmid 15,Tx8+$40  Tick count min/eight
        Lmid 14,Tx15+$40 Tick count units
        Lmid 0,THour+$40
        Lmid 5,UHour+$40
        Lmid 5,TMin+$40
        Lmid 4,UMin+$40
        Lmid 0,WTHour+$40
        Lmid 8,WUHour+$40
        Lmid 0,WTMin+$40
        Lmid 0,WUMin+$40
        Lmid 5,BeepVol
        Lmid 1,HMP1
        Lmid 1,HMP2
        Lmid 1,HMP3
        Lmid 1,HMP4
        Lmid 0,$3F       bank select=0
Reset3  Lwi 1            MS 2 bits
        Lbi 15           loop counter
        Lai 0            middle 4 bits
        Lxa              middle 4 bits
        Lyi 0            LS 4 bits
        Alei 15          make ST=1
        Call Reset2      clear alarm memory 100-1FF
        Lwi 2
        Lbi 9            loop counter
        Lai 0            middle 4 bits
        Lxa              middle 4 bits
        Lyi 0            LS 4 bits
        Alei 15          make ST=1
        Call Reset2      clear alarm memory 200-29F
        Inemd 14,Timeout
        Brs Reset4       do it again on bank 1
        Call BackTOD     clear display etc.
        Alei 15
        Call Egoedl
        Lmid 3,TxReg     Time control reg
        Remd 2,$1        reset timer A flag
```

Medi-Monitor Corporation — Confidential

MediMonitor assembly language program for Hitachi 4bit Microcontroller HD4074808, page 24
©1989, 1990 Current Designs Corporation, New York, NY, Medi-Monitor Corporation

```
            Remd 3,$1          un-mask timer A
            Remd 2,$0          reset int 0 flag
            Remd 3,$0          un-mask int 0
            Semd 0,$0          enable interrupts
            nop                >>> this is the end of Reset <<<
Main        Stop               This is the main loop
            nop
            Jmpl Main Reset2      Lmiiy 0            clears up to 256 nibbles of ram
            Brs Reset2         go around until Y=0
            Ai 1
            Lxa
            Db                 you get 1 more than starting #
            Brs Reset2         if => 0
            Rtn                ST=1 on rtn
Reset4      Lmid 14,Timeout
            Lmid 1,$3F         bank select=1
            Brs Reset3

*           --------- This is the button interrupt routine ---------
Int0        Semd 3,$0          mask int 0
            Lar 0              get buttons 1,2,3,4 into A
            Alei 14            Last, Next, Check, Set
            Brs But00          14 or less means it's 1,2,3, or 4
*               The button branch tables are arranged in
*               this order: Last, Next, Check, Set, Yes, No
*               Each uses 256 byrds (1 page) of ROM
            Lar 1              get buttons 5,6,7,8 into A
            Lya                ----- check buttons 5,6 -----
            Lamd State
            Lba                get state into B
            Lai 0
            Ynei 14            button 5
            Brs But05
            Tbr BtBrTbl+1      ------------- Next -------------
But05       Ynei 13            button 6
            Brs ButWait        if not 5 or 6
            Tbr BtBrTbl        ------------- Last -------------

But00       Lya                ----- check buttons 1,2,3,4 ------
            Lamd State
            Lba                get state into B
            Lai 0
            Ynei 14            button 1
            Brs But01
            Tbr BtBrTbl+3      ------------- Set -------------
But01       Ynei 13            button 2
            Brs But02
            Tbr BtBrTbl+2      ------------- Check -------------
But02       Ynei 11            button 3
            Brs But03
            Tbr BtBrTbl+5      ------------- No ---------------
But03       Ynei 7             button 4
            Brs ButWait
            Tbr BtBrTbl+4      ------------- Yes --------------

*                              -----> set time; decrement minute -----
LAStime     Lai 2
            Xmra DownT         make downtime=2
```

Medi-Monitor Corporation - Confidential

MediMonitor assembly language program for Hitachi 4bit Microcontroller HD4074808, page 25
©1989, 1990 Current Designs Corporation, New York, NY, Medi-Monitor Corporation

```
          But12a   Tmd 0,City
                   Call LastMin      if setting clock
                   Tmd 1,City
                   Call Las5min      if setting wake-up time
                   Tmd 2,City
                   Call Las5min      if setting Special Schedule time
                   Tmd 0,City
                   Call ShowTim      if setting clock
                   Tmd 1,City
                   Call ShwATim      if setting wake-up time
                   Tmd 2,City
                   Call ShwATim      if setting Special Schedule time
          But12b   Lmid 0,Blink      stop blinking the time
                   Semd 0,$0         enable interrupts
                   nop
                   nop
                   Remd 0,$0         disable interrupts
                   Lmid 3,Timeout    restart Timeout
                   Lmid 1,Blink      resume blinking the time
                   Lar 1
                   Lya
                   Ynei 13           if LAST button not down
                   Brs ButUp         done
                   Lamr DownT
                   Lya
                   Ynei 4
                   Brs But12c        if not 4
                   Lai 5
                   Brs But12e
          But12c   Ynei 7
                   Brs But12d        if not 7
                   Lai 8
                   Brs But12e
          But12d   Alei 9
                   Brs But12b        if < 10
                   Ynei 15
                   Brs But12e        if not 15
                   Lai 11
          But12e   Xmra DownT
                   Call Wait         33 ms. delay
                   Jmpl But12a

*                          -----> set time; increment minute -----
          NXtime   Lai 2
                   Xmra DownT        make downtime=2
          But11a   Tmd 0,City
                   Call NextMin      if setting clock
                   Tmd 1,City
                   Call Nxt5min      if setting wake-up time
                   Tmd 2,City
                   Call Nxt5min      if setting Special Schedule time
                   Tmd 0,City
                   Call ShowTim      if setting clock
                   Tmd 1,City
                   Call ShwATim      if setting wake-up time
                   Tmd 2,City
                   Call ShwATim      if setting Special Schedule time
          But11b   Lmid 0,Blink      stop blinking the time
                   Semd 0,$0         enable interrupts
                   nop
```

Medi-Monitor Corporation – Confidential

MediMonitor assembly language program for Hitachi 4bit Microcontroller HD4074808, page 26
©1989, 1990 Current Designs Corporation, New York, NY, Medi-Monitor Corporation

```
                nop
                Remd 0,$0         disable interrupts
                Lmid 3,Timeout    restart Timeout
                Lmid 1,Blink      resume blinking the time
                Lar 1
                Lya
                Ynei 14           if NEXT button not down
                Brs ButUp         done
                Lamr DownT
                Lya
                Ynei 4
                Brs But11c        if not 4
                Lai 5
                Brs But11e
        But11c  Ynei 7
                Brs But11d        if not 7
                Lai 8
                Brs But11e
        But11d  Alei 9
                Brs But11b        if < 10
                Ynei 15
                Brs But11e        if not 15
                Lai 11
        But11e  Xmra DownT
                Call Wait         33 ms. delay
                Jmpl But11a ChkWU   Lamr WTHour       ------> Check wake-up-time ------
                Xmra $C
                Lamr WUHour       Units hours
                Xmra $D
                Lamr WTMin        Tens mins
                Xmra $E
                Lamr WUMin        Units mins
                Xmra $F
                Remd 0,Blink      stop blinking
                Alei 15           make ST=1
                Call ShwATim      display wake-up-time
                Jmpl ButWait InWake  Lamr $C           ------> Install new wake-up-time ------
                Xmra WTHour
                Lamr $D           Units hours
                Xmra WUHour
                Lamr $E           Tens mins
                Xmra WTMin
                Lamr $F           Units mins
                Xmra WUMin
        *                 now clear out all standard schedules & re-install them
                Lmid 1,which
                Lamd TypeS1
                Lmad TypeT
                Alei 5
                Call Install      if not special, install it
                Lmid 2,which
                Lamd TypeS2
                Lmad TypeT
                Alei 5
                Call Install      if not special, install it
                Lmid 3,which
```

Medi-Monitor Corporation - Confidential

MediMonitor assembly language program for Hitachi 4bit Microcontroller HD4074808, page 27
©1989, 1990 Current Designs Corporation, New York, NY, Medi-Monitor Corporation

```
        Lamd TypeS3
        Lmad TypeT
        Alei 5
        Call Install    if not special, install it
        Lmid 4,which
        Lamd TypeS4
        Lmad TypeT
        Alei 5
        Call Install    if not special, install it
        Alei 15         make ST=1
        Jmpl StChkWU    go back to check wake-up-time ShowTPD Call ClrTime    clear time display
        Remd iASNEED    clear AS NEEDED
        Remd iEVYODY    clear EVERY OTHER DAY
        Remd iNEXT      clear NEXT
        Remd iTIME      clear TIME
        Remd iSPCIAL    clear SPECIAL
        Remd iQUERY     clear ?
        Lmid 0,Blink    stop blinking
        Lmid 0,FlashAN  stop flashing
        Lmid 0,FlashEO
        Lmid 0,FlashSP
        Lmid 0,FlashQY
        Lamd TypeT
        Jmpl ChkSkd5

ChkSkd  Lya             ---------> Check Schedule ---------
        Semd iCHCKNG
        Semd iSCHED
        Semd iTIPRDY
        Ynei 1          Y holds which
        Brs ChkSkd2     if which isn't 1
        Call S1HMPn     turn on HMP
        Lamd TypeS1
        Brs ChkSkd5
ChkSkd2 Ynei 2
        Brs ChkSkd3
        Call S2HMPn
        Lamd TypeS2
        Brs ChkSkd5
ChkSkd3 Ynei 3
        Brs ChkSkd4
        Call S3HMPn
        Lamd TypeS3
        Brs ChkSkd5
ChkSkd4 Call S4HMPn
        Lamd TypeS4     what type of schedule
ChkSkd5 Lya             ---> Set Times per Day jumps in here
        Lmad TypeT      type > temp schedule type
        Ynei 0          Y now holds schedule type
        Brs ChkSkd6
        Semd iASNEED    type 0 = as needed
        Inemd 5,State
        Brs ButWait     if not Setting Times per Day
        Lmid 1,FlashAN  if setting, flash
        Jmpl ButWait
ChkSkd6 Ynei 5
        Brs ChkSkd7
        Semd iEVYODY    type 5 = every other day
```

Medi-Monitor Corporation – Confidential liMonitor assembly language program for Hitachi 4bit Microcontroller HD4074808, page 28
©1989, 1990 Current Designs Corporation, New York, NY, Medi-Monitor Corporation

```
            Lai 1
            Inemd 5,State
            Brs ChkSkd8      if not Setting Times per Day
            Lmid 1,FlashEO   if setting, flash
            Jmpl ChkSkd8
ChkSkd7     Ynei 6
            Brs ChkSkd8
            Semd iSPCIAL     type 6 = special
            Inemd 5,State
            Brs ChkSkd9      if not Setting Times per Day
            Lmid 1,FlashSP   if setting, flash
            Jmpl ButWait
ChkSkd9     Lmid 3,State     check special schedule
            Call CT2AA       clock time to alarm address
            Call PushWXY     save
            Lwi 0
            Lxi 9
            Lamd which       which compartment
            Lya              now WXY points to Special,2,3, or 4
            Lam
            Lmad SpeciaT     store How Many Times in temp
            Alei 9
            Brs ChkSkd8      if < 10, show it
            Ai 6             same as -10
            Xmra $F
            Lmid 1,$4E       add tens digit
            Brs ChkSk10      then show it
ChkSkd8     Xmra $F          schedule type > Umin
            Lmid 11,$4E      blank others
ChkSk10     Lmid 11,$4D
            Lmid 11,$4C
            Call ShwATim     display schedule type
            Inemd 5,State
            Brs ButWait      if not Setting Times per Day
            Lmid 1,Blink     if setting, blink
            Jmpl ButWait

*           ----- Get Last Pill-Taken Time (all compartments) -----
*           The first push of the LAST button brings us here.
LastA       Remd 0,TxReg     disallow show-time
            Call Clear
            Semd iLAST
            Semd iTIME
            Lmid 0,which     which=0 causes GetLP to check all
            Lmid 0,Skdlst    schedule first? (0=no)
            Lmid 0,StoreLP   Temporary Last pill store
            Lmid 0,AfterM    clear After midnight flag
            Call CT2AA       clock time to alarm address
            Call GetLP       get last pill taken
            Inemd 10,$4E
            Brs NextA2       if none found
            Call PushWXY
            Call SaveWXY     keep the first found time here
            Inemd 0,Skdlst   schedule first?
            Brs LastA3       if we found a last, show HMP & time
LastA6      Semd iMISSED     otherwise, we found a missed pill
            Tmd 0,StoreMP
            Call S1HMPn      turn on HMP
            Tmd 1,StoreMP
            Call S2HMPn      turn on HMP
```

Medi-Monitor Corporation – Confidential

MediMonitor assembly language program for Hitachi 4bit Microcontroller HD4074808, page 29
©1989, 1990 Current Designs Corporation, New York, NY, Medi-Monitor Corporation

```
            Tmd 2,StoreMP
            Call S3HMPn        turn on HMP
            Tmd 3,StoreMP
            Call S4HMPn        turn on HMP
            Call WXY2CT        alarm address to clock time
            Alei 15            make ST=1
            Call ShwATim
            Rtn

*           --------- Get Last Pill-Taken Time continued ---------
*           All subsequent pushes of the LAST button bring us here.
LastA5      Call PopWXY        this gets the present address
            Inemd 0,Skdlst     schedule first?
            Brs LastA7         if schedule first
            Dy                 if record first, don't check the same one
            Alei 15            make ST=1
LastA7      Call GetLP         get last pill taken
            Inemd 10,$4E
            Brs NextA2         if none found
            Call PushWXY
            Call PshESav       see if push=save. Returns 0 in A if equal
            Alei 1
            Brs NextA2         if equal, we're done
            Inemd 0,Skdlst     schedule first?
            Brs LastA3         if we found a last, show HMP & time
            Brs LastA6         otherwise, we found a missed pill
LastA3      Tm 0               ----- show HMP & time -----
            Call S1HMPn        turn on HMP
            Tm 1
            Call S2HMPn        turn on HMP
            Tm 2
            Call S3HMPn        turn on HMP
            Tm 3
            Call S4HMPn        turn on HMP
            Call WXY2CT        alarm address to clock time
            Alei 15            make ST=1
            Call ShwATim
            Rtn

*           ------ Get Next Alarm Time (all compartments) ------
NextA       Call Clear
            Semd iNEXT
            Semd iTIME
            Remd 0,TxReg       disallow show-time
            Lmid 0,which       which=0 causes GetAM to check all
            Call CT2AA         clock time to alarm address
            Iy
            Lmid 0,AfterM      clear After midnight flag
            Call GetAM         find next alarm in Compartment(which)
            Ilemd 9,$4E
            Brs NextA13
            Brs NextA2         if no alarms found
NextA13     Call PushWXY
            Call SaveWXY       keep the first found alarm here
            Inemd 13,$4E
            Brs NextA3         if found in 1st or 2nd segment
            XspXY              hold XY
            Call CT2AA
            Xspx               .because there is no Lax
            Laspx              .X > A
```

Medi-Monitor Corporation — Confidential

MediMonitor assembly language program for Hitachi 4bit Microcontroller HD4074808, page 30
©1989, 1990 Current Designs Corporation, New York, NY, Medi-Monitor Corporation

```
          Xspx
          Anemd Zstack+$6  alarm time X
          Brs NextA11      if clock time X <> alarm time X
          Lay
          Alemd Zstack+$7  alarm time Y
          Brs NextA2       if clock time <= alarm time
*                          we're done because the search went past 24 hours
          Brs NextA12      if we found a real alarm
NextA11   Alemd Zstack+$6  alarm time X
          Brs NextA2       if clock time <= alarm time
NextA12   XspXY            restore XY
          Jmpl NextA3
NextA5    Call GetAM       -- get next alarm in Compartment(which) --
          Ilemd 9,$4E
          Brs NextA14
          Brs NextA2       if no alarms found
NextA14   Call PushWXY
          Call PshESav     see if push=save. Returns 0 in A if equal
          Alei 1
          Brs NextA2       if equal, we're done
NextA3    Tmd 0,GPreg+$40  ----- show HMP & time -----
          Call S1HMPn      turn on HMP
          Tmd 1,GPreg+$40
          Call S2HMPn      turn on HMP
          Tmd 2,GPreg+$40
          Call S3HMPn      turn on HMP
          Tmd 3,GPreg+$40
          Call S4HMPn      turn on HMP
          Call WXY2CT      alarm address to clock time
          Alei 15          make ST=1
          Call ShwATim
          Rtn
NextA2    Lamd Return      -----> Last jumps in here -----
          Lmad State       restore state
          Call Clear
          Semd 0,TxReg     allow show-time
          Call ShowTim
          Rtn
*                ------ Get Next/Last Special Alarm Time ------
*                which=compartment, TypeT=6=special
GetLst    Call PopWXY      this gets the present alarm address
          Dy
          Alei 15          make ST=1
          Call GetLAlm     get last alarm
          Jmpl GetNxt3
GetNxtA   Call PopWXY      this gets the present alarm address
          Iy
          Call GetAM       find alarm in Compartment(which)
GetNxt3   Ilemd 9,$4E
          Brs GetNxt2      if alarm found
          Rtn
GetNxt2   Call PushWXY
          Alei 15          make ST=1
          Call WXY2CT      alarm address to clock time
          Alei 15          make ST=1
          Call ShwATim
          Rtn
*         ------- Search Alarm Schedule in Compartment(which) ------
```

Medi-Monitor Corporation - Confidential

MediMonitor assembly language program for Hitachi 4bit Microcontroller HD4074808, page 31
©1989, 1990 Current Designs Corporation, New York, NY, Medi-Monitor Corporation

```
*                  if which=0, search all compartments
*                  Search starts at address in WXY
*                  Returns found alarm address in WXY. ST=1 on rtn
*                  If none found, $4E=6. If found, $4E>9.
*                  If search goes past midnight, AfterM > 0
        GetAM    Lmid 0,$3F      bank select=0 (pill schedule)
                 Lmid 2,$4D      bit 1 set
                 Lmid 3,$4E      counts searches
                 Law
                 Alei 1
                 Brs GetAM9      if W=1
                 Brs GetAM10     if W=2
        GetAM9   Lwi 1           ----- search from WXY to 1FF -----
                 Xspx            .
                 Laspx           .
                 Xspx            X > A
                 Lba             loop counter
                 Comb
                 Alei 15         make ST=1
                 Call GetAM8
                 Lamr $E
                 Ai 1
                 Xmra $E
                 Alei 4
                 Brs GetAM7      if not found, check out 200-27F
                 Rtn GetAM12  Lwi 1           ----- search from 100 to 1FF -----
                 Lmid 2,AfterM   set after midnight flag
                 Lbi 15          loop counter
                 Lai 0           middle 4 bits
                 Lxa             middle 4 bits
                 Lyi 1           LS 4 bits
                 Dy              to set status
                 Call GetAM8
                 Lamr $E
                 Ai 1
                 Xmra $E
                 Alei 4
                 Brs GetAM7      if not found, check out 200-27F
                 Rtn GetAM7   Lwi 2           ----- search from 200 to 27F -----
                 Lbi 8           loop counter
                 Lai 0           middle 4 bits
                 Lxa             middle 4 bits
                 Lyi 1           LS 4 bits
                 Dy              to set status
                 Call GetAM8
                 Lamr $E
                 Ai 1
                 Xmra $E
                 Alei 4
                 Brs GetAM12     if not found, check out 100-1FF
                 Rtn GetAM10  Lwi 2           ----- search from WXY to 27F -----
                 Xspx            .
                 Laspx           .
                 Xspx            X > A
```

Medi-Monitor Corporation — Confidential

MediMonitor assembly language program for Hitachi 4bit Microcontroller HD4074808, page 32
©1989, 1990 Current Designs Corporation, New York, NY, Medi-Monitor Corporation

```
            Ai 8              so B will have complement-8
            Lba               loop counter
            Comb
            Ai 8              restore A to equal X
            Alei 15           make ST=1
            Call GetAM8
            Lamr $E
            Ai 1
            Xmra $E
            Alei 4
            Brs GetAM12       if not found, check out 100-1FF
            Rtn Found1      Lamr $E
            Ai 7
            Xmra $E
            Rtn               from GetAM8 call GetAM8      Inemd 0,which
            Brs GetAM13
            Brs GetAM15       search all if which=0
GetAM13     Inemd 1,which
            Brs GetAM5
            Brs GetAM1
GetAM5      Inemd 2,which
            Brs GetAM6
            Brs GetAM2
GetAM6      Inemd 3,which
            Brs GetAM4
            Brs GetAM3
GetAM1      Tm 0              searches compartment 1 alarms
            Brs Found1        if found
            Iy
            Brs GetAM1        go around until Y=0
            Ai 1
            Lxa
            Db                you get 1 more than starting #
            Brs GetAM1        if => 0
            Rtn
GetAM2      Tm 1              searches compartment 2 alarms
            Brs Found1        if found
            Iy
            Brs GetAM2        go around until Y=0
            Ai 1
            Lxa
            Db                you get 1 more than starting #
            Brs GetAM2        if => 0
            Rtn
GetAM3      Tm 2              searches compartment 3 alarms
            Brs Found1        if found
            Iy
            Brs GetAM3        go around until Y=0
            Ai 1
            Lxa
            Db                you get 1 more than starting #
            Brs GetAM3        if => 0
            Rtn
GetAM4      Tm 3              searches compartment 4 alarms
            Brs Found1        if found
            Iy
```

Medi-Monitor Corporation — Confidential

MediMonitor assembly language program for Hitachi 4bit Microcontroller HD4074808, page 33
©1989, 1990 Current Designs Corporation, New York, NY, Medi-Monitor Corporation

```
          Brs GetAM4      go around until Y=0
          Ai 1
          Lxa
          Db               you get 1 more than starting #
          Brs GetAM4       if => 0
          Rtn
GetAM15   Inem 0           searches all compartments
          Brs EODtest      if we found something
GetAM16   Iy
          Brs GetAM15      go around until Y=0
          Ai 1
          Lxa
          Db               you get 1 more than starting #
          Brs GetAM15      if => 0
          Rtn

*         Determine if found alarm is an Every-Other-Day type
*         and if it is, did we find it in a pill day, or in a
*         no-pill day.  If it's in a no-pill day, mask it out
*         so it doesn't get displayed.
EODtest   Xmra GPreg       store A
          Lamd AfterM      after midnight flag is bit 1
          Eormd TxReg      pill day flag is bit 1
          Anmd $4D         bit 1 set
          Lam
          Brs EODtes2      if it's pill day, we found it!
*         if not, then find out if this is an E.O.D. pill
          Anmd EODay       daily bit=1; E.O.D. bit=0 (EOD mask)
EODtes2   Xmra GPreg       store alarm in GPreg & restore A
          Brs Found1       if we found an alarm
          Jmpl GetAM16     if not

*         ----- Search Last Pill Record in Compartment(which) -----
*         If which=0, search all compartments (Last function).
*         Search starts at address in WXY and works back.
*         If starting Y=15, begin search at previous WX address.
*         Returns found address in WXY. ST=1 on rtn.
*         If none found, $4E=6. If found, $4E=10.
*              If search goes past midnight, $AfterM > 0
GetLAlm   Lmid 0,$3F       bank select=0 (pill schedule)
          Brs GetLAL2
GetLP     Lmid 1,$3F       bank select=1 (permanent record)
GetLAL2   Lmid 3,$4E       counts searches
          Lmid 2,$4D       bit 1 set
          Xspx             .
          Laspx            X > A
          Ynei 15
          Brs GetLP25      standard
          Ai 15            decrement
          Brs GetLP25      if it was > 0, standard
          Lmid 4,$4E       now we only need 2 searches
          Law
          Alei 1
          Brs GetLP7       if W=1
          Brs GetLP12      if W=2
GetLP25   Lxa
          Lba              X > B
          Law
          Alei 1
          Brs GetLP9       if W=1
```

Medi-Monitor Corporation – Confidential

MediMonitor assembly language program for Hitachi 4bit Microcontroller HD4074808, page 34
©1989, 1990 Current Designs Corporation, New York, NY, Medi-Monitor Corporation

```
        Brs GetLP10     if W=2
GetLP9  Lwi 1           ----- search from WXY to 100 -----
        Call GetLP8
        Lamr $E
        Ai 1
        Xmra $E
        Alei 4
        Brs GetLP7      if not found, check out 27C-200
        Rtn
GetLP10 Lwi 2           ----- search from WXY to 200 -----
        Call GetLP8
        Lamr $E
        Ai 1
        Xmra $E
        Alei 4
        Brs GetLP12     if not found, check out 1FC-100
        Rtn GetLP12 Lwi 1           ----- search from 1FC to 100 -----
        Lbi 15          X
        Lxi 15          X
        Lyi 12          LS 4 bits
        Call GetLP8
        Lamr $E
        Ai 1
        Xmra $E
        Alei 4
        Brs GetLP7      if not found, check out 27C-200
        Rtn
GetLP7  Lwi 2           ----- search from 27C to 200 -----
        Lmid 2,AfterM   set after midnight flag
        Lbi 7           X
        Lxi 7           X
        Lyi 12          LS 4 bits
        Call GetLP8
        Lamr $E
        Ai 1
        Xmra $E
        Alei 4
        Brs GetLP12     if not found, check out 1FC-100
        Rtn Found2  Lmid 9,$4E
        Rtn GetLP8  Inemd 0,which
        Brs GetLP13
        Brs GetLP14     search all if which=0
GetLP13 Inemd 1,which
        Brs GetLP5
        Brs GetLP1
GetLP5  Inemd 2,which
        Brs GetLP6
        Brs GetLP2
GetLP6  Inemd 3,which
        Brs GetLP4
        Brs GetLP3

GetLP1  Tm 0            searches compartment 1 alarms
        Brs Found2      if found
```

Medi-Monitor Corporation -- Confidential

MediMonitor assembly language program for Hitachi 4bit Microcontroller HD4074808, page 35
©1989, 1990 Current Designs Corporation, New York, NY, Medi-Monitor Corporation

```
        Dy
        Brs GetLP1      go around until Y < 0
        Db
        Lab
        Lxa
        Brs GetLP1      if => 0
        Rtn
GetLP2  Tm 1            searches compartment 2 alarms
        Brs Found2      if found
        Dy
        Brs GetLP2      go around until Y < 0
        Db
        Lab
        Lxa
        Brs GetLP2      if => 0
        Rtn
GetLP3  Tm 2            searches compartment 3 alarms
        Brs Found2      if found
        Dy
        Brs GetLP3      go around until Y < 0
        Db
        Lab
        Lxa
        Brs GetLP3      if => 0
        Rtn
GetLP4  Tm 3            searches compartment 4 alarms
        Brs Found2      if found
        Dy
        Brs GetLP4      go around until Y < 0
        Db
        Lab
        Lxa
        Brs GetLP4      if => 0
        Rtn GetLP14 Inemd 0,Skd1st  schedule first?
        Brs GetLP16     if yes
GetLP15 Lmid 1,$3F      bank select=1 (permanent RECORD)
        Inem 0          searches all compartments
        Brs FoundTP     if taken pill found
GetLP16 Lmid 0,$3F      bank select=0 (pill SCHEDULE)
        Inem 0          searches all compartments
        Brs FoundSP     if schedule found
GetLP17 Dy
        Brs GetLP15     go around until Y < 0
        Db
        Lab
        Lxa
        Brs GetLP15     if => 0
        Rtn
FoundTP Lamd StoreLP    -----> taken pill found
        Orm
        Lmad StoreLP    keep pills taken in StoreLP
        Lmid 5,Skd1st   upon return, continue with SCHEDULE
        Jmpl Found2     return FoundSP Lamd StoreLP    -----> schedule found
        Anm             mask out other compartments
        Eorm            mask out taken pills
        Lmad StoreMP    keep missed pills in StoreMP
```

Medi-Monitor Corporation - Confidential

MediMonitor assembly language program for Hitachi 4bit Microcontroller HD4074808, page 36
©1989, 1990 Current Designs Corporation, New York, NY, Medi-Monitor Corporation

```
            Lamd AfterM     after midnight flag is bit 1
            Eormd TxReg     pill day flag is bit 1
            Anmd $4D        bit 1 set
            Brs FoundS2     if it's pill day
            Lamd StoreMP
            Anmd EODay      daily bit=1; E.O.D.bit=0 (EOD mask)
            Lmad StoreMP
    FoundS2 Lamd StoreLP
            Eorm
            Anmd StoreLP    mask out taken pills
            Lmad StoreLP    update StoreLP
            Lmid 0,Skdlst   upon return, continue with RECORD
            Lai 0
            Ormd StoreMP
            Brs Found2      if any 1's, they are the missed pills
            Brs GetLP17     if no missed pills, continue PushWXY Law
            Lmad Zstack+$5  W
            Xspx            .because there is no Lax
            Laspx           .X > A
            Xspx            .
            Lmad Zstack+$6  X
            Lay
            Lmad Zstack+$7  Y
            Rtn
    PopWXY  Lamd Zstack+$5
            Lwa
            Lamd Zstack+$6
            Lxa
            Lamd Zstack+$7
            Lya
            Rtn SaveWXY Law
            Lmad Zstack+$8
            Xspx            .because there is no Lax
            Laspx           .X > A
            Xspx            .
            Lmad Zstack+$9
            Lay
            Lmad Zstack+$A
            Rtn
    LoadWXY Lamd Zstack+$8
            Lwa
            Lamd Zstack+$9
            Lxa
            Lamd Zstack+$A
            Lya
            Rtn PshESav Lamd Zstack+$5
            Anemd Zstack+$8
            Brs PshESa2     if not equal
            Lamd Zstack+$6
            Anemd Zstack+$9
            Brs PshESa2
            Lamd Zstack+$7
            Anemd Zstack+$A
            Brs PshESa2
```

Medi-Monitor Corporation − Confidential

MediMonitor assembly language program for Hitachi 4bit Microcontroller HD4074808, page 37
©1989, 1990 Current Designs Corporation, New York, NY, Medi-Monitor Corporation

```
                Lai 0           if equal
                Rtn
      PshESa2   Lai 15          if not equal
                Rtn SPQ1u     Lai 1           ------> Set Pill Quantity 1 up ------
                Amd HMP1        add 1 to how many pills
                Alei 3
                Brs SPQ1u5      if 3 or less
                Lai 1           make it 1
      SPQ1u5    Lmad HMP1       store
                Call S1HMPn     show
                Jmpl ButWait SPQ2u     Lai 1           ------> Set Pill Quantity 2 up ------
                Amd HMP2        add 1 to how many pills
                Alei 3
                Brs SPQ2u5      if 3 or less
                Lai 1           make it 1
      SPQ2u5    Lmad HMP2       store
                Call S2HMPn     show
                Jmpl ButWait SPQ3u     Lai 1           ------> Set Pill Quantity 3 up ------
                Amd HMP3        add 1 to how many pills
                Alei 3
                Brs SPQ3u5      if 3 or less
                Lai 1           make it 1
      SPQ3u5    Lmad HMP3       store
                Call S3HMPn     show
                Jmpl ButWait SPQ4u     Lai 1           ------> Set Pill Quantity 4 up ------
                Amd HMP4        add 1 to how many pills
                Alei 3
                Brs SPQ4u5      if 3 or less
                Lai 1           make it 1
      SPQ4u5    Lmad HMP4       store
                Call S4HMPn     show
                Jmpl ButWait SPQ1d     Lai 2           ------> Set Pill Quantity 1 down ------
                Sec
                Smcd HMP1       subtract 2 from how many pills
                Brs SPQ1d6      if => 0
                Lai 2
      SPQ1d6    Ai 1            add 1 back
                Lmad HMP1       store
                Alei 15         make ST=1
                Call S1HMPn     show
                Jmpl ButWait SPQ2d     Lai 2           ------> Set Pill Quantity 2 down ------
                Sec
                Smcd HMP2       subtract 2 from how many pills
                Brs SPQ2d6      if => 0
                Lai 2
      SPQ2d6    Ai 1            add 1 back
                Lmad HMP2       store
                Alei 15         make ST=1
```

Medi-Monitor Corporation - Confidential diMonitor assembly language program for Hitachi 4bit Microcontroller HD404828, page 38
©1989, 1990 Current Designs Corporation, New York, NY, Medi-Monitor Corporation

```
            Call S2HMPn     show
            Jmpl ButWait
                            ------> Set Pill Quantity 3 down ------
    SPQ3d   Lai 2
            Sec
            Smcd HMP3       subtract 2 from how many pills
            Brs SPQ3d6      if => 0
            Lai 2
    SPQ3d6  Ai 1            add 1 back
            Lmad HMP3       store
            Alei 15         make ST=1
            Call S3HMPn     show
            Jmpl ButWait
                            ------> Set Pill Quantity 4 down ------
    SPQ4d   Lai 2
            Sec
            Smcd HMP4       subtract 2 from how many pills
            Brs SPQ4d6      if => 0
            Lai 2
    SPQ4d6  Ai 1            add 1 back
            Lmad HMP4       store
            Alei 15         make ST=1
            Call S4HMPn     show
            Jmpl ButWait ChkBeep Semd iVOLUME    ------> Check Beep Volume ------
            Semd iBEEP
            Semd iCHCKNG    turn on CHECKING
    AdjVol  Lamd BeepVol
            Xmra $E         volume > Tmin
            Lmid 11,$4F     blank others
            Lmid 11,$4D
            Lmid 11,$4C
            Alei 15         make ST=1
            Call ShwATim    display volume
            Jmpl ButWait

*       ------> Install Schedule (not special) ------
    InstalS Remd iSET       clear SET
            Semd iCHCKNG    turn on CHECKING
            Alei 15         make ST=1
            Call Install
            Jmpl ShowTPD
    Install Lwi 0           ---- Install Schedule (not special) ----
            Lxi 8
            Lamd which      which compartment
            Lya
            Lamd TypeT
            Lma             store type of schedule
            Call ClrAM      clear old alarms
            Inemd 0,TypeT
            Brs Instal3
            Rtn             if type 0 (as needed) we're done
    Instal3 Lamr WTHour
            Lya
            Lamr WUHour
            Call Ct2At      clock time to alarm time (hours)
            Lamr WTMin
            Sec
            Inemd 0,WUMin+$40
```

Medi-Monitor Corporation - Confidential

MediMonitor assembly language program for Hitachi 4bit Microcontroller HD4074808, page 39
©1989, 1990 Current Designs Corporation, New York, NY, Medi-Monitor Corporation

```
          Brs Instal2     if unit min not 0
          Rec
Instal2   Rotl            convert tens min to alarm min
          Lya             now alarm (wake-up) address is in WXY
          Call InstalA    install An alarm
          Inemd 1,TypeT
          Brs Instal4
          Rtn             if type 1, we're done
Instal4   Inemd 5,TypeT
          Brs Instal5
          Lamd which      if type 5 (every other day)
          Lya
          Ynei 1
          Brs Insta51     if not compartment 1
          Remd 0,EODay    reset every other day bit
          Rtn
Insta51   Ynei 2
          Brs Insta52
          Remd 1,EODay
          Rtn
Insta52   Ynei 3
          Brs Insta53
          Remd 2,EODay
          Rtn
Insta53   Remd 3,EODay
          Rtn
Instal5   Inemd 2,TypeT
          Brs Instal6
          Law             if type 2, install 2nd alarm
          Alei 1
          Xspx
          Brs Inst21      if before 16:00
          Brs Inst24
Inst21    Laspx
          Alei 11
          Brs Inst22      if before 12:00
Inst24    Lwi 1           morning hours
          Laspx           2 instructions just to get X into A
          Ai 4            add 12 (with overflow)
          Lxa             set X
          Alei 15         make ST=1
          Call InstalA    install An alarm
          Rtn
Inst22    Ai 12           add 12 hours
          Lxa             set X
          Brs Inst23      if now after 16:00
          Call InstalA    install An alarm
          Rtn
Inst23    Lwi 2           evening hours
          Call InstalA    install An alarm
          Rtn Instal6   Inemd 3,TypeT
          Brs Instal7
          Call Add6Hrs    if type 3, install 2nd
          Call Add6Hrs    & 3rd alarm
          Rtn Instal7   Call Add4Hrs    if type 4, install 2nd
          Call Add4Hrs    3rd
```

Medi-Monitor Corporation - Confidential

MediMonitor assembly language program for Hitachi 4bit Microcontroller HD4074808, page 40
©1989, 1990 Current Designs Corporation, New York, NY, Medi-Monitor Corporation

```
         Call Add4Hrs    & 4th alarms
         Rtn

Add6Hrs  Xspx
         Law
         Alei 1
         Brs Add6Hr2     if before 16:00
         Laspx
         Alei 1
         Brs Add6Hr2     if before 18:00
         Ai 14           add 6 hours (with overflow)
Add6Hr4  Lxa
         Lwi 1           morning hours
         Call InstalA    install An alarm
         Rtn
Add6Hr2  Laspx
         Ai 6            add 6 hours
Add6Hr3  Lxa
         Brs Inst23      if now after 16:00
         Call InstalA    install An alarm
         Rtn Add4Hrs  Xspx
         Law
         Alei 1
         Brs Add4Hr2     if before 16:00
         Laspx
         Alei 3
         Brs Add4Hr2     if before 20:00
         Ai 12           add 4 hours (with overflow)
         Brs Add6Hr4
Add4Hr2  Laspx
         Ai 4
         Jmpl Add6Hr3    done

*        ---------- Install Alarm for Compartment(which) ---------
InstalA  Inemd 1,which
         Brs InstA1
         Sem 0           install alarm for compartment 1
         Rtn
InstA1   Inemd 2,which
         Brs InstA2
         Sem 1           install alarm for compartment 2
         Rtn
InstA2   Inemd 3,which
         Brs InstA3
         Sem 2           install alarm for compartment 3
         Rtn
InstA3   Sem 3           install alarm for compartment 4
         Rtn

*        ---------- Clear Alarms for Compartment(which) ---------
ClrAM    Lmid 0,$3F      bank select=0
         Lwi 1           MS 2 bits
         Lbi 15          loop counter
         Lai 0           middle 4 bits
         Lxa             middle 4 bits
         Lyi 1           LS 4 bits
         Dy              to set status
         Call ClrAM8     clear alarm memory 100-1FF
```

Medi-Monitor Corporation – Confidential

MediMonitor assembly language program for Hitachi 4bit Microcontroller HD4074808, page 41
©1989, 1990 Current Designs Corporation, New York, NY, Medi-Monitor Corporation

```
        Lwi 2
        Lbi 8           loop counter
        Lai 0           middle 4 bits
        Lxa             middle 4 bits
        Lyi 1           LS 4 bits
        Dy              to set status
        Call ClrAM8     clear alarm memory 200-28F
        Rtn
ClrAM8  Inemd 1,which
        Brs ClrAM5
        Call ClrAM1
        Semd 0,EODay    set every other day bit
        Rtn
ClrAM5  Inemd 2,which
        Brs ClrAM6
        Call ClrAM2
        Semd 1,EODay
        Rtn
ClrAM6  Inemd 3,which
        Brs ClrAM7
        Call ClrAM3
        Semd 2,EODay
        Rtn
ClrAM7  Call ClrAM4
        Semd 3,EODay
        Rtn
ClrAM1  Rem 0           clears compartment 1 alarms
        Iy
        Brs ClrAM1      go around until Y=0
        Ai 1
        Lxa
        Db              you get 1 more than starting #
        Brs ClrAM1      if => 0
        Rtn
ClrAM2  Rem 1           clears compartment 2 alarms
        Iy
        Brs ClrAM2      go around until Y=0
        Ai 1
        Lxa
        Db              you get 1 more than starting #
        Brs ClrAM2      if => 0
        Rtn
ClrAM3  Rem 2           clears compartment 3 alarms
        Iy
        Brs ClrAM3      go around until Y=0
        Ai 1
        Lxa
        Db              you get 1 more than starting #
        Brs ClrAM3      if => 0
        Rtn
ClrAM4  Rem 3           clears compartment 4 alarms
        Iy
        Brs ClrAM4      go around until Y=0
        Ai 1
        Lxa
        Db              you get 1 more than starting #
        Brs ClrAM4      if => 0
        Rtn Spcl00  Semd 0,Blink    ------> Start Set Special Schedule ------
```

Medi-Monitor Corporation — Confidential

I claim:
1. A device for alerting a person when it is time to take medication, comprising,
   (a) a casing having at least one face,
   (b) a display on said face,
   (c) a memory,
   (d) timing means,
   (e) a plurality of medication compartments that open and close, associated with said casing,
   (f) control means for providing a plurality of bits of information relating to the taking of medication, said control means including the timing means, said information including information as to the quantity of medication to be taken and also including other information,
   (g) selecting means for selecting at least one of said bits and at least one time of day, for each compartment,
   (h) means for entering the selected bits and said selected time or times in said memory,
   (i) said control means including means responsive to both said selected time or times and said selected bits stored in said memory, for, a particular one of said compartments, (a) giving a take-medication signal at each of said time or times that was selected for that compartment, and (b) displaying on said display the information that was based on the bit or bits selected for that compartment,
   (j) said display having first and second portions the first of which is closer to said compartments than the second portion, said control means including means for displaying said information as to the quantity of medication to be taken on said first portion and said other information on said second portion, and
   (k) means operable following a take-medication signal to store a missed medication signal in said memory, if a compartment is not opened or closed,
   said control means including means for displaying, on said display, the missed medication signal.

2. A device according to claim 1 in which said control means includes means for displaying a plurality of past times that medication was to be taken from a given compartment together with any missed medication signal applicable to such compartment.

3. A device according to claim 2 in which the time at which the missed medication was scheduled to be taken is displayed on said display along with the missed medication signal.

4. A device for alerting a person when it is time to take medication, comprising,
   (a) a casing having at least one face,
   (b) a display on said face,
   (c) a memory,
   (d) timing means,
   (e) a plurality of medication compartments that open and close, associated with said casing,
   (f) control means for providing a plurality of bits of information relating to the taking of medication, said control means including the timing means, said information including information as to the quantity of medication to be taken and also including other information,
   (g) selecting means for selecting at least one of said bits and at least one time of day, for each compartment,
   (h) means for entering the selected bits and said selected time or times in said memory,
   (i) said control means including means responsive to both said selected time or times and said selected bits stored in said memory, for, a particular one of said compartments, (a) giving a take-medication signal at each of said time or times that was selected for that compartment, and (b) displaying on said display the information that was based on the bit or bits selected for that compartment,
   (j) said display having first and second portions the first of which is closer to said compartments than the second portion, said control means including means for displaying said information as to the quantity of medication to be taken on said first portion and said other information on said second portion,
   (k) wherein if one of said compartments is opened at an unscheduled time, said device gives a signal and the display displays a query as to whether the patient wishes to take medication from such one compartment.

5. A device as defined in claim 4, having manually operable means for answering said query.

6. A device as defined in claim 5 wherein the answer to said query is stored in said memory available for display by said display at a later time.

* * * * *